(12) United States Patent
Finke et al.

(10) Patent No.: US 6,479,518 B2
(45) Date of Patent: Nov. 12, 2002

(54) ZWITTERIONIC TACHYKININ RECEPTOR ANTAGONISTS

(75) Inventors: Paul E. Finke, Milltown, NJ (US); Laura C. Meurer, Scotch Plains, NJ (US); Sander G. Mills, Scotch Plains, NJ (US); Malcolm MacCoss, Freehold, NJ (US); Hongbo Qi, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 9 days.

(21) Appl. No.: 09/957,965

(22) Filed: Sep. 21, 2001

(65) Prior Publication Data

US 2002/0042431 A1 Apr. 11, 2002

Related U.S. Application Data

(60) Provisional application No. 60/234,490, filed on Sep. 22, 2000.

(51) Int. Cl.[7] .................. A61K 31/445; C07D 211/06
(52) U.S. Cl. .............. 514/330; 546/239; 546/210; 544/172; 544/399; 548/252; 548/254; 548/572; 562/512; 564/163; 564/164; 514/237.5; 514/255; 514/381; 514/423; 514/561; 514/613
(58) Field of Search ................ 514/330, 237.5, 514/255, 326, 381, 423, 557, 581, 613; 546/239, 210; 548/252, 254, 572; 544/172, 399; 562/512; 564/163, 164

(56) References Cited

U.S. PATENT DOCUMENTS

| 5,387,595 | A | | 2/1995 | Merck |
| 5,719,147 | A | | 2/1998 | Merck |
| 5,750,549 | A | * | 5/1998 | Caldwell et al. ............ 514/364 |

FOREIGN PATENT DOCUMENTS

| WO | WO 00/56727 | 9/2000 |

OTHER PUBLICATIONS

Mills, et al., *Bioorg. & Med. Chem. Lett.*, 5(13),1345(1995).
Kramer, et al., *Science*, 281, 1640–1645 (1998).
Rupniak, et al., *TIPS*, 20, 485–490 (1999).

* cited by examiner

*Primary Examiner*—Charanjit S. Aulakh
(74) *Attorney, Agent, or Firm*—J. Eric Thies; Melvin Winokur

(57) ABSTRACT

The present invention is directed to certain novel compounds represented by structural formula I:

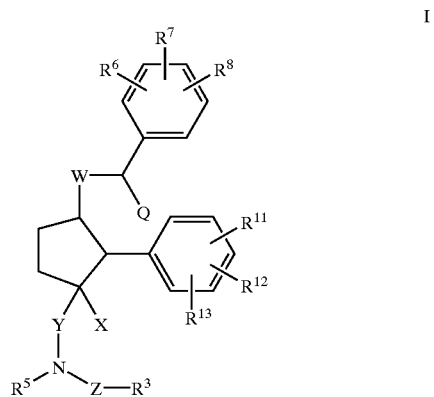

or a pharmaceutically acceptable salt thereof, wherein $R^3$, $R^5$, $R^6$, $R^7$, $R^8$, $R^{11}$, $R^{12}$, $R^{13}$, Q, W, X, Y and Z are defined herein. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of psychiatric disorders including depression and anxiety.

25 Claims, No Drawings

ZWITTERIONIC TACHYKININ RECEPTOR ANTAGONISTS

CROSS REFERENCE TO RELATED APPLICATIONS

This application claims priority under 35 U.S.C. §119(e) from Ser. No. 60/234,490, filed Sep. 22, 2000.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to SP the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Evidence has been reviewed for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia.

It has furthermore been suggested that tachykinin receptor antagonists have utility in the following disorders: anxiety, depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus, ophthalmic diseases such as conjunctivitis, vernal conjunctivitis, and the like, and cutaneous diseases such as contact dermatitis, atopic dermatitis, urticaria, and other eczematoid dermatitis.

Attempts have been made to provide antagonists for the receptors of substance P and other tachykinin peptides in order to more effectively treat the various disorders and diseases mentioned above. For example, U.S. Pat. Nos. 5,387,595, 5,750,549 and *Bioorg. & Med. Chem. Lett.*, 1345 (1995) disclose certain alicyclic compounds as tachykinin receptor antagonists.

SUMMARY OF THE INVENTION

This invention is concerned with novel compounds represented by structural formula I:

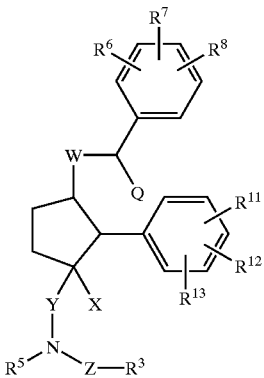

or a pharmaceutically acceptable salt thereof, wherein $R^3$, $R^5$, $R^6$, $R^7$, $R^8$, $R^{11}$, $R^{12}$, $R^{13}$, Q, W, X, Y and Z are defined herein. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of psychiatric disorders including depression and anxiety.

DESCRIPTION OF THE INVENTION

The present invention is directed to compounds of the structural formula I:

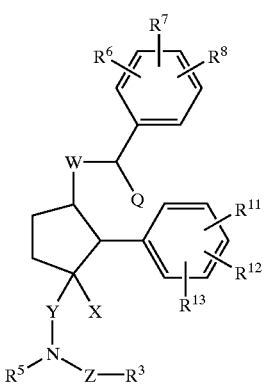

or a pharmaceutically acceptable salt thereof, wherein:
Q is selected from the group consisting of:
 (1) hydrogen,
 (2) $C_{1-6}$ alkyl,
 (3) $C_{1-6}$ alkyl-OH, and
 (4) $C_{1-6}$ alkyl-O—$C_{1-6}$ alkyl;
W is selected from the group consisting of:
 (2) —NH—, and
 (3) —N($C_{1-6}$ alkyl)-;
X is selected from the group consisting of:
 (1) hydrogen, and
 (2) $C_{1-6}$ alkyl, and
 (3) $C_{1-6}$ alkyl-OH;
Y is selected from the group consisting of:
 (1) a single bond, and
 (2) $C_{1-6}$ alkyl, unsubstituted or substituted with one or more of the substituents selected from:

(a) hydroxy,
(b) oxo,
(c) $C_{1-6}$ alkoxy,
(d) phenyl-$C_{1-3}$ alkoxy,
(e) phenyl,
(f) —CN,
(g) halo, wherein halo is fluoro, chloro, bromo or iodo,
(h) —NR$^9$R$^{10}$, wherein R$^9$ and R$^{10}$ are independently selected from:
  (I) hydrogen,
  (II) $C_{1-6}$ alkyl,
  (III) phenyl,
  (IV) ($C_{1-6}$ alkyl)-phenyl,
  (V) ($C_{1-6}$ alkyl)-hydroxy, and
  (VI) ($C_{1-6}$ alkyl)-($C_{1-4}$ alkoxy),
(i) —NR$^9$—COR$^{10}$,
(j) —NR$^9$—CO$_2$R$^{10}$,
(k) —CO—NR$^9$R$^{10}$,
(l) —COR$^9$, and
(m) —CO$_2$R$^9$;

Z is selected from the group consisting of:
$C_{1-6}$ alkyl, $C_{3-6}$ cycloalkyl and $C_{1-6}$ alkyl($C_{3-6}$ cycloalkyl), which is unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —NR$^9$R$^{10}$,
(i) —NR$^9$—COR$^{10}$,
(j) —NR$^9$—CO$_2$R$^{10}$,
(k) —CO—NR$^9$R$^{10}$,
(l) —COR$^9$, and
(m) —CO$_2$R$^9$;

R$^3$ is selected from the group consisting of:
(1) —CO$_2$H,
(2) -tetrazolyl, and
(3) —CO—NH—SO$_2$—CH$_3$;

R$^5$ is selected from the group consisting of:
(1) hydrogen,
(2) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —NR$^9$R$^{10}$,
  (i) —NR$^9$—COR$^{10}$,
  (j) —NR$^9$—CO$_2$R$^{10}$,
  (k) —CO—NR$^9$R$^{10}$,
  (l) —COR$^9$, and
  (m) —CO$_2$R$^9$, or R$^5$ and Z may be joined together to form a pyrrolidinyl, piperidinyl, piperazinyl or morpholinyl ring which is substituted with R$^3$ and further substituted with one or more of the substituents selected from:
(a) $C_{1-6}$ alkyl,
(b) ($C_{1-6}$ alkyl)-phenyl,
(c) ($C_{1-6}$ alkyl)-hydroxy,
(d) ($C_{1-6}$ alkyl)-($C_{1-4}$ alkoxy),
(e) hydroxy,
(f) oxo,
(g) $C_{1-6}$ alkoxy,
(h) phenyl-$C_{1-3}$ alkoxy,
(i) phenyl,
(j) —CN,
(k) halo,
(l) —NR$^9$R$^{10}$,
(m) —NR$^9$—COR$^{10}$,
(n) —NR$^9$—CO$_2$R$^{10}$,
(o) —CO—NR$^9$R$^{10}$,
(p) —COR$^9$, and
(q) —CO$_2$R$^9$, R$^6$, R$^7$ and R$^8$ are independently selected from the group consisting of:
(1) hydrogen,
(2) $C_{1-6}$alkoxy,
(3) halo,
(4) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —NR$^9$R$^{10}$,
  (i) —NR$^9$—COR$^{10}$,
  (j) —NR$^9$—CO$_2$R$^{10}$,
  (k) —CO—NR$^9$R$^{10}$,
  (l) —COR$^9$,
  (m) —CO$_2$R$^9$,
  (n) heterocycle, wherein heterocycle is selected from the group consisting of:
    (A) benzimidazolyl,
    (B) benzofuranyl,
    (C) benzothiophenyl,
    (D) benzoxazolyl,
    (E) furanyl,
    (F) imidazolyl,
    (G) indolyl,
    (H) isooxazolyl,
    (I) isothiazolyl,
    (J) oxadiazolyl,
    (K) oxazolyl,
    (L) pyrazinyl,
    (M) pyrazolyl,
    (N) pyridyl,
    (O) pyrimidyl,
    (P) pyrrolyl,
    (Q) quinolyl,
    (R) tetrazolyl,
    (S) thiadiazolyl,
    (T) thiazolyl,
    (U) thienyl,
    (V) triazolyl,
    (W) azetidinyl,
    (X) 1,4-dioxanyl,
    (Y) hexahydroazepinyl,
    (Z) piperazinyl,
    (AA) piperidinyl,
    (AB) pyrrolidinyl,
    (AC) morpholinyl,
    (AC) thiomorpholinyl,
    (AD) dihydrobenzimidazolyl,
    (AE) dihydrobenzofuranyl, (AF) dihydrobenzothiophenyl,
(AG) dihydrobenzoxazolyl,
(AH) dihydrofuranyl
(AI) dihydroimidazolyl,
(AJ) dihydroindolyl,
(AK) dihydroisooxazolyl,
(AL) dihydroisothiazolyl,
(AM) dihydrooxadiazolyl,
(AN) dihydrooxazolyl,
(AO) dihydropyrazinyl,
(AP) dihydropyrazolyl,
(AQ) dihydropyridinyl,
(AR) dihydropyrimidinyl,
(AS) dihydropyrrolyl,
(AT) dihydroquinolinyl,
(AU) dihydrotetrazolyl,
(AV) dihydrothiadiazolyl,
(AW) dihydrothiazolyl,
(AX) dihydrothienyl,
(AY) dihydrotriazolyl,
(AZ) dihydroazetidinyl,
(BA) dihydro-1,4-dioxanyl,
(BB) tetrahydrofuranyl, and
(BC) tetrahydrothienyl,
and wherein the heterocycle is unsubstituted or substituted with one or more substituent(s) selected from:
(i) $C_{1-6}$ alkyl, unsubstituted or substituted with halo, —$CF_3$—$OCH_3$, or phenyl,
(ii) $C_{1-6}$ alkoxy,
(iii) oxo,
(iv) hydroxy,
(v) thioxo,
(vi) —$SR^9$,
(vii) halo,
(viii) cyano,
(ix) phenyl,
(x) trifluoromethyl,
(xi) —$(CH_2)_m$—$NR^9R^{10}$,
(xii) —$NR^9COR^{10}$,
(xiii) —$CONR^9R^{10}$,
(xiv) —$CO_2R^9$, and
(xv) —$(CH_2)_m$—$OR^9$,
(5) hydroxy,
(6) —CN,
(7) —$CF_3$,
(8) —$NO_2$,
(9) —$SR_{14}$, wherein $R^{14}$ is hydrogen or $C_{1-6}$alkyl,
(10) —$SOR^{14}$,
(11) —$SO_2R_{14}$,
(12) —$NR^9$—$COR^{10}$,
(13) —CO—$NR^9$—$COR^{10}$,
(14) —$NR^9R^{10}$,
(15) —$NR^9$—$CO_2R^{10}$,
(16) —$COR^9$,
(17) —$CO_2R^9$,
(18) heterocycle, wherein heterocycle is as defined above,
(19) —($C_{1-6}$alkyl)-heterocycle, wherein heterocycle is as defined above,
(20) —N(heterocycle)—$SO_2R^{14}$, wherein heterocycle is as defined above;
$R^{11}$, $R^{12}$ and $R^{13}$ are independently selected from:
(1) hydrogen,
(2) $C_{1-6}$ alkyl, unsubstituted or substituted with one or more of the substituents selected from:

(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9$—$COR^{10}$,
(j) —$NR^9$—$CO_2R^{10}$,
(k) —CO—$NR^9R^{10}$,
(l) —$COR^9$,
(m) —$CO_2R^9$;
(3) halo,
(4) —CN,
(5) —$CF_3$,
(6) —$NO_2$,
(7) hydroxy,
(8) $C_{1-6}$alkoxy,
(9) —$COR^9$, and
(10) —$CO_2R^9$;
and pharmaceutically acceptable salts and individual diasteromers thereof.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

In addition compounds with carbon-carbon double bonds may occur in Z- and E-forms with all isomeric forms of the compounds being included in the present invention.

When any variable (e.g., alkyl, aryl, Q, W, X, Y, Z, $R^3$, $R^5$, $R^6$, $R^7$, $R^8$, $R^9$, $R^{10}$, $R^{11}$, $R^{12}$, $R^{13}$, $R^{14}$, $R^{15}$, m, n, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

In the compounds of the present invention, if Y is a single bond, then —N($R^5$)—Z—$R^3$ is attached directly to the cyclopentyl ring.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

One embodiment of the present invention is directed to the compounds of structural formula I, or a pharmaceutically acceptable salt thereof, in which W is —O— of the formula:

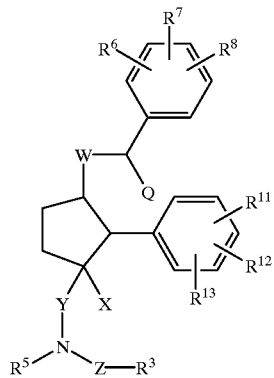

or a pharmaceutically acceptable salt thereof, wherein $R^3$, $R^5$, $R^6$, $R^7$, $R^8$, $R^{11}$, $R^{12}$, $R^{13}$, Q, W, X, Y and Z are defined herein.

One group within the embodiment of the compounds of the invention where W is —O— is that wherein Q is $C_{1-6}$ alkyl.

One group within the embodiment of the compounds of the invention where W is —O— is that wherein Q is $C_{1-6}$ alkyl-OH.

One group within the embodiment of the compounds of the invention where W is —O— is that wherein Q is hydrogen.

In the compounds of the present invention where W is —O—, it is preferred that Q is hydrogen, —CH$_3$ or —CH$_2$—OH.

An embodiment of the present invention includes those compounds of structural formula I, or a pharmaceutically acceptable salt thereof, wherein:

Q is selected from the group consisting of:
(1) hydrogen,
(2) —CH$_3$, and
(3) —CH$_2$—OH;

W is —O—;

X is hydrogen;

Y is selected from the group consisting of:
(1) a single bond,
(2) —CH$_2$—, and
(3) —CH$_2$—OH;

Z is selected from the group consisting of: $C_{1-6}$ alkyl, $C_{3-6}$ cycloalkyl and $C_{1-6}$ alkyl($C_{3-6}$ cycloalkyl);

$R^3$ is —CO$_2$H;

$R^5$ is selected from the group consisting of:
(1) hydrogen, and
(2) $C_{1-6}$ alkyl,
or $R^5$ and Z are joined together to form a piperidinyl ring which is substituted with $R^3$ and which is further unsubstituted or substituted with $C_{1-6}$ alkyl;

$R^6$, $R^7$ and $R^8$ are independently selected from the group consisting of:
(1) hydrogen,
(2) —CF$_3$,
(3) $C_{1-6}$alkoxy, and
(4) 1-, 2- or 5-tetrazolyl, wherein the tetrazolyl is unsubstituted or substituted with a substitutent selected from the group consisting of:
(a) $C_{1-6}$ alkyl,
(b) -cyclopropyl,
(c) CH$_2$-cyclopropyl,
(d) —S—$C_{1-4}$alkyl,
(e) —SO—$C_{1-4}$alkyl,
(f) SO$_2$—$C_{1-4}$alkyl,
(g) phenyl,
(h) —NR$^9$R$^{10}$,
(i) —CH$_2$—CO—CF$_3$, and
(j) —CF$_3$;

$R^{11}$, $R^{12}$ and $R^{13}$ are independently selected from:
(1) hydrogen, and
(2) fluoro;

and pharmaceutically acceptable salts and individual diasteromers thereof.

An embodiment of the present invention includes those compounds wherein Q is selected from the group consisting of:
(1) hydrogen,
(2) —CH$_3$, and
(3) —CH$_2$—OH.

An embodiment of the present invention includes those compounds wherein Q is —CH$_3$.

An embodiment of the present invention includes those compounds wherein W is —O—.

An embodiment of the present invention includes those compounds wherein Y is selected from the group consisting of:
(1) a single bond,
(2) —CH$_2$—, and
(3) —CH$_2$—OH.

An embodiment of the present invention includes those compounds wherein Y is —CH$_2$—.

An embodiment of the present invention includes those compounds wherein $R^3$ is —CO$_2$H.

An embodiment of the present invention includes those compounds wherein $R^5$ is selected from the group consisting of:
(1) hydrogen, and
(2) methyl.

An embodiment of the present invention includes those compounds wherein Z is selected from the group consisting of:
(1) —CH$_2$—,
(2) —CH$_2$CH$_2$—,
(3) —CH$_2$C(CH$_3$)$_2$—,
(4) —CH$_2$C(CH$_2$CH$_3$)$_2$—,
(5) —CH$_2$C(CH$_3$)(CH(CH$_3$)$_2$)—,
(6) —CH$_2$C(cyclopentyl)-, and
(7) —CH$_2$C(cyclohexyl)-.

An embodiment of the present invention includes those compounds wherein $R^5$ and Z are joined together to form a piperidinyl ring which is substituted with $R^3$ and which is further unsubstituted or substituted with methyl.

An embodiment of the present invention includes those compounds wherein $R^6$, $R^7$ and $R^8$ are independently selected from the group consisting of:
(1) hydrogen,
(2) —CF$_3$,
(3) C$_{1-4}$alkoxy, and
(4) heterocycle, wherein the heterocycle is selected from the group consisting of:
   (A) tetrazolyl,
   (B) imidazolyl,
   (C) triazolyl,
   (D) pyridyl,
and wherein the heterocycle is unsubstituted or substituted with one or more substituent(s) selected from:
   (i) C$_{1-4}$ alkyl,
   (ii) -cyclopropyl, and
   (iii) —CF$_3$.

An embodiment of the present invention includes those compounds wherein the phenyl ring bearing $R^6$, $R^7$ and $R^8$ is selected from:
3,5-bis(trifluormethyl)phenyl,
2-methoxy-5-tetrazol-1-yl-phenyl,
2-methoxy-5-(5-methyl-tetrazol-1-yl)-phenyl,
2-methoxy-5-(5-ethyl-tetrazol-1-yl)-phenyl,
2-methoxy-5-(5-propyl-tetrazol-1-yl)-phenyl,
2-methoxy-5-(5-trifluoromethyl-tetrazol-1-yl)-phenyl,
2-methoxy-5-(5-cyclopropyl-tetrazol-1-yl)-phenyl, and
2-methoxy-5-(5-methylsulfanyl-tetrazol-1-yl)-phenyl.

An embodiment of the present invention includes those compounds wherein $R^{11}$, $R^{12}$ and $R^{13}$ are independently selected from:
(1) hydrogen, and
(2) fluoro.

An embodiment of the present invention includes those compounds wherein the phenyl ring bearing $R^{11}$, $R^{12}$ and $R^{13}$ is unsubstituted phenyl or is parafluorophenyl.

Exemplifying the invention is the use of the compounds disclosed in the Examples and herein.

Specific compounds within the present invention include a compound which selected from the group consisting of the title compounds of the Examples; and pharmaceutically acceptable salts thereof and individual diastereomers thereof.

Specific compounds within the present invention include:
1-(S)-(1-(R)-(3,5-Bis(trifluoromethyl)phenyl)ethoxy)-2-(R)-(4-fluorophenyl)-3-(R)-(((R and/or S)-3-carboxylpyrrolidin-1-yl)methyl)cyclopentane;
1-(S)-(1-(R)-(3,5-Bis(trifluoromethyl)phenyl)ethoxy)-2-(R)-(4-fluorophenyl)-3-(R)-(((2-carboxylethyl)methylamino)methyl)cyclopentane;
1-(S)-(1-(R)-(3,5-Bis(trifluoromethyl)phenyl)ethoxy)-2-(S)-(4-fluorophenyl)-3-(R)-((2-carboxylethyl)methylamino)cyclopentane;
1-(S)-(1-(R)-(3,5-Bis(trifluoromethyl)phenyl)ethoxy)-2-(S)-(4-fluorophenyl)-3-(R)-((3-carboxylpropyl)methylamino)cyclopentane;
1-(S)-(1-(R)-(3,5-Bis(trifluoromethyl)phenyl)ethoxy)-2-(R)-(4-fluorophenyl)-3-(R)-((3-carboxylpropyl)methylamino)methyl)cyclopentane;
1-(S)-(1-(R)-(3,5-Bis(trifluoromethyl)phenyl)ethoxy)-2-(R)-(4-fluorophenyl)-3-(R)-((4-carboxylpiperidin-1-yl)methyl)cyclopentane;
1-(S)-(1-(R)-(3,5-Bis(trifluoromethyl)phenyl)ethoxy)-2-(R)-(4-fluorophenyl)-3-(R)-((4-carboxyl-4-methylpiperidin-1-yl)methyl)cyclopentane;
1-(S)-(1-(R)-(3,5-Bis(trifluoromethyl)phenyl)ethoxy)-2-(S)-(4-fluorophenyl)-3-(R)-((carboxylmethyl)methylamino)cyclopentane;
1-(S)-(1-(R)-(3,5-Bis(trifluoromethyl)phenyl)ethoxy)-2-(R)-(4-fluorophenyl)-3-(R)-(((R)-2-carboxylpyrrolidin-1-yl)methyl)cyclopentane;
1-(S)-(1-(R)-(3,5-Bis(trifluoromethyl)phenyl)ethoxy)-2-(R)-(4-fluorophenyl)-3-(R)-(((RS)-3-carboxylpiperidin-1-yl)methyl)cyclopentane;
1-(S)-(1-(R)-(3,5-Bis(trifluoromethyl)phenyl)ethoxy)-2-(R)-(4-fluorophenyl)-3-(R)-((3-carboxylazetidin-1-yl)methyl)cyclopentane;
1-(S)-(1-(R)-(3,5-Bis(trifluoromethyl)phenyl)ethoxy)-2-(R)-(4-fluorophenyl)-3-(R)-(((2-carboxylethyl)amino)methyl)cyclopentane;
1-(S)-(1-(R)-(3,5-Bis(trifluoromethyl)phenyl)ethoxy)-2-(R)-(4-fluorophenyl)-3-(R)-(((carboxylmethyl)amino)methyl)cyclopentane;
1-(S)-(1-(R)-(3,5-Bis(trifluoromethyl)phenyl)ethoxy)-2-(R)-(4-fluorophenyl)-3-(R)-((((S)-1-carboxylethyl)amino)methyl)cyclopentane;
1-(S)-(1-(R)-(3,5-Bis(trifluoromethyl)phenyl)ethoxy)-2-(R)-(4-fluorophenyl)-3-(R)-((((R)-1-carboxylethyl)amino)methyl)cyclopentane;
1-(S)-(1-(R)-(3,5-Bis(trifluoromethyl)phenyl)ethoxy)-2-(S)-(4-fluorophenyl)-3-(R)-(ethylamino)cyclopentane;
1-(S)-(1-(R)-(3,5-Bis(trifluoromethyl)phenyl)ethoxy)-2-(R)-(4-fluorophenyl)-3-(R)-((4-(tetrazol-5-yl)piperidin-1-yl)methyl)cyclopentane;
1-(S)-(1-(R)-(3,5-Bis(trifluoromethyl)phenyl)ethoxy)-2-(R)-(4-fluorophenyl)-3-(R)-(((2-(tetrazol-5-yl)ethyl)methylamino)methyl)cyclopentane;
1-(S)-(1-(R)-(3,5-Bis(trifluoromethyl)phenyl)ethoxy)-2-(R)-(4-fluorophenyl)-3-(S)-((4-carboxylpiperidin-1-yl)methyl)cyclopentane;
1-(S)-(1-(R)-(3-Fluoro-5-trifluoromethyl)phenyl)ethoxy)-2-(R)-(4-fluorophenyl)-3-(R)-((4-carboxylpiperidin-1-yl)methyl)cyclopentane;
1-(S)-(1-(R)-(3,5-Bis(trifluoromethyl)phenyl)ethoxy)-2-(R)-(4-fluorophenyl)-3-(R)-((4-(methylsulfonylaminocarbonyl)piperidin-1-yl) methyl)cyclopentane;
1-(S)-(1-(3,5-Bis(trifluoromethyl)phenyl)methoxy)-2-(R)-(4-fluorophenyl)-3-(R)-(carboxyl)cyclopentane;
1-(S)-(1-(3,5-Bis(trifluoromethyl)phenyl)methoxy)-2-(R)-(4-fluorophenyl)-3-(R)-(hydroxymethyl)cyclopentane;
1-(S)-(1-(3,5-Bis(trifluoromethyl)phenyl)methoxy)-2-(R)-(4-fluorophenyl)-3-(R)-((4-carboxylpiperidin-1-yl)methyl)cyclopentane;

1-(S)-(1-(3,5-Bis(trifluoromethyl)phenyl)methoxy)-2-(R)-(4-fluorophenyl)-3-(R)-(((S)-2-carboxylpyrrolidin-1-yl)methyl)cyclopentane;

1-(S)-(1-(3,5-Bis(trifluoromethyl)phenyl)methoxy)-2-(R)-(4-fluorophenyl)-3-(R)-(((R,S)-3-carboxylpyrrolidin-1-yl)methyl)cyclopentane;

1-(S)-(1-(3,5-Bis(trifluoromethyl)phenyl)methoxy)-2-(R)-(4-fluorophenyl)-3-(R)-(((2-carboxylethyl)amino)methyl)cyclopentane;

1-(S)-(1-(3,5-Bis(trifluoromethyl)phenyl)methoxy)-2-(R)-(4-fluorophenyl)-3-(R)-(((2-carboxylethyl)methylamino)methyl)cyclopentane;

1-(S)-(1-(S)-(3,5-Bis(trifluoromethyl)phenyl)-2-hydroxyethoxy)-2-(R)-(4-fluorophenyl)-3-(R)-(hydroxymethyl)cyclopentane;

1-(S)-(1-(S)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane;

1-(S)-(1-(R)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-((((2-carboxylethyl)methyl)amino)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R,S)-3-carboxylpyrrolidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-((4-carboxyl-4-methylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R and S)-3-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((RS)-3-carboxylpiperazin-1-yl)methyl)cyclopentane;

1-(S)-(1-(R)-(3,5-Bis(trifluoromethyl)phenyl)ethoxy)-2-(R)-(4-fluorophenyl)-3-(R)-(((RS)-2-carboxyl-1-methylpiperazin-4-yl)methyl)cyclopentane;

1-(S)-(1-(R)-(3,5-Bis(trifluoromethyl)phenyl)ethoxy)-2-(R)-(4-fluorophenyl)-3-(R)-(((RS)-2-carboxylmorpholin-4-yl)methyl)cyclopentane;

1-(S)-(1-(R)-(3,5-Bis(trifluoromethyl)phenyl)ethoxy)-2-(R)-(4-fluorophenyl)-3-(R)-(((R)-3-carboxyl-3-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxyl-3-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((1-carboxyl-1-methyl)ethyl)aminomethyl)cyclopentane;

1-(S)-(1-(R)-(3,5-Bis(trifluoromethyl)phenyl)ethoxy)-2-(R)-(4-fluorophenyl)-3-(R)-((((R)-1-carboxyl-1,2-dimethylprop-1-yl)amino)methyl)cyclopentane;

1-(S)-(1-(R)-(3,5-bis(trifluoromethyl)phenyl)ethoxy)-2-(R)-(4-fluorophenyl)-3-(R)-((((S)-1-carboxyl-1,2-dimethylprop-1-yl)aminomethyl)cyclopentane;

1-(S)-(1-(R)-(3,5-Bis(trifluoromethyl)phenyl)ethoxy)-2-(R)-(4-fluorophenyl)-3-(R)-(((R)-3-carboxyl-(R)-5-methylpiperidin-1-yl)methyl)cyclopentane;

1-(S)-1-(R)-(3,5-Bis(trifluoromethyl)phenyl)ethoxy)-2-(R)-(4-fluorophenyl)-3-(R)-(((S)-3-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-((((S)-1-carboxylethyl)methylamino)methyl)cyclopentane;

1-(S)-(1-(R)-(3,5-Bis(trifluoromethyl)phenyl)ethoxy)-2-(R)-(4-fluorophenyl)-3-(R)-((((R)-1-carboxylethyl)methylamino)methyl)cyclopentane;

1-(S)-(1-(R)-(3,5-Bis(trifluoromethyl)phenyl)ethoxy)-2-(R)-(4-fluorophenyl)-3-(R)-((((RS)-2-carboxylprop-1-yl)methylamino)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R)-3-carboxyl-3-methylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-(((S)-3-carboxyl-3-methylpiperidin-1-yl)methyl)cyclopentane;

1-(S)-(1-(R)-(3,5-Bis(trifluoromethyl)phenyl)ethoxy)-2-(S)-(4-fluorophenyl)-3-(R)-((2-carboxyl-2-methylprop-1-yl)methylamino)cyclopentane;

1-(S)-(1-(R)-(3,5-Bis(trifluoromethyl)phenyl)ethoxy)-2-(S)-(4-fluorophenyl)-3-(R)-((2-carboxyl-2-ethylbut-1-yl)methylamino)cyclopentane;

1-(S)-(1-(R)-(3,5-Bis(trifluoromethyl)phenyl)ethoxy)-2-(R)-(4-fluorophenyl)-3-(R)-(((1-carboxylcyclopent-1-yl)methyl)methylamino)cyclopentane;

1-(S)-(1-(R)-(3,5-Bis(trifluoromethyl)phenyl)ethoxy)-2-(R)-(4-fluorophenyl)-3-(R)-((1-carboxylcyclohex-1-ylamino)methyl)cyclopentane;

1-(S)-(1-(R)-(3,5-Bis(trifluoromethyl)phenyl)ethoxy)-2-(R)-(4-fluorophenyl)-3-(R)-((1-carboxylcyclopent-1-ylamino)methyl)cyclopentane;

1-(S)-(1-(R)-(3,5-Bis(trifluoromethyl)phenyl)ethoxy)-2-(R)-(4-fluorophenyl)-3-(R)-(((1-carboxylcyclohex-1-yl)methylamino)methyl)cyclopentane;

1-(S)-(1-(R)-(3,5-Bis(trifluoromethyl)phenyl)ethoxy)-2-(R)-(4-fluorophenyl)-3-(R)-(((1-carboxylcyclopent-1-yl)methylamino)methyl)cyclopentane;

1-(S)-(1-(R)-(3,5-Bis(trifluoromethyl)phenyl)ethoxy)-2-(R)-(4-fluorophenyl)-3-(R)-(((R)-3-carboxylpiperidin-1-yl)methyl)cyclopentane;

and pharmaceutically acceptable salts and individual diasteromers thereof.

There are several acceptable methods of naming the compounds discussed herein.

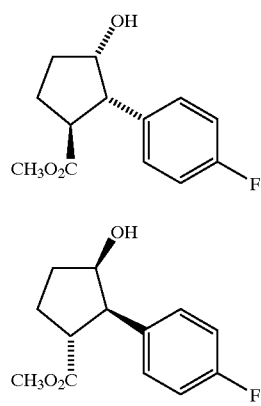

For example, the racemic mixture of A and B shown above can be named either as "(1RS,2RS,3RS)-2-(4-fluorophenyl)-3-hydroxycyclopentane-carboxylic acid methyl ester" or as "methyl 3-(SR)-hydroxy-2-(SR)-(4-fluoro)phenyl-1-(SR)-carboxylate".

Throughout the instant application, the following abbreviations are used with the following meanings:

| Reagents: | |
|---|---|
| Cbz-Cl | benzyl chloroformate |
| BOP | benzotriazol-1-yloxy tris(dimethylamino)phosphonium hexafluorophosphate |
| CDI | 1,1'-carbonyldiimidazole |
| ACE-Cl | alpha-chloroethyl chloroformate |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DIBAL | diisobutylaluminum hydride |
| iPr$_2$NEt or DIPEA | N,N-diisopropylethylamine |
| EDC | 1-(3-dimethylaminopropyl)-3-ethylcarbodiimide hydrochloride |
| DMAP | 4-dimethylaminopyridine |
| Me$_2$SO$_4$ | dimethyl sulfate |
| EDAC | 1-ethyl-3-(3-dimethylaminopropyl)carbodiimide hydrochloride |
| HOBt | 1-hydroxybenzotriazole hydrate |
| NHS | N-hydroxysuccinimide |
| LAH | lithium aluminum hydride |
| LHMDS | lithium bis(trimethylsilyl)amide |
| NMM | N-methylmorpholine |
| KHMDS | potassium bis(trimethylsilyl)amide |
| NaOEt | sodium ethoxide |
| Et$_3$N | triethylamine |
| Ph$_3$P | triphenylphosphine |
| TFA | trifluoroacetic acid |
| Solvents: | |
| AcOH | acetic acid |
| MeCN | acetonitrile |
| AmOH | n-amyl alcohol |
| DMSO | dimethylsulfoxide |
| DMF | N,N-dimethylformamide |
| EtOH | ethanol |
| MeOH | methanol |
| THF | tetrahydrofuran |
| Others: | |
| Am | n-amyl |
| Ar | aryl |
| BOC | tert-butoxycarbonyl |
| Bn | benzyl |
| Bu | butyl |
| Cbz | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| H or hr | hour(s) |
| HPLC | high pressure liquid chromatography |
| iPr | isopropyl |
| MPLC | medium pressure liquid chromatography |
| Me | methyl |
| MHz | megahertz |
| Min | minute(s) |
| MF | molecular formula |
| NMR | nuclear magnetic resonance |
| Ph | phenyl |
| PTC | phase transfer catalyst |
| prep. | prepared or preparative |
| Pr | propyl |
| rt | room temperature |
| TLC | thin layer chromatography |
| TMS | tetramethylsilane |

The preparation of compounds of Formula I of the present invention may be carried out in sequential or convergent synthetic routes. Syntheses detailing the preparation of the compounds of Formula I in a sequential manner are presented in the following reaction schemes. The skills required in carrying out the reaction and purification of the resulting reaction products are known to those in the art. Purification procedures includes crystallization, normal phase or reverse phase chromatography.

Several methods for preparing the compounds of this invention are illustrated in the following Schemes and Examples wherein the variables are as defined above or as defined herein.

SCHEME 1

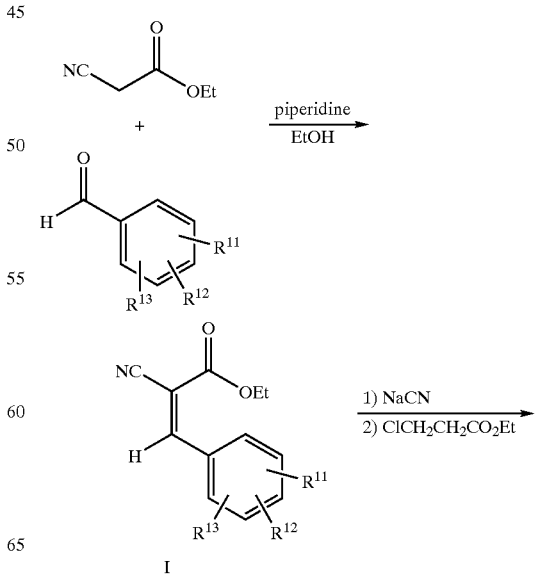

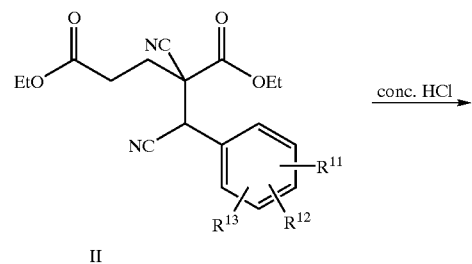

II

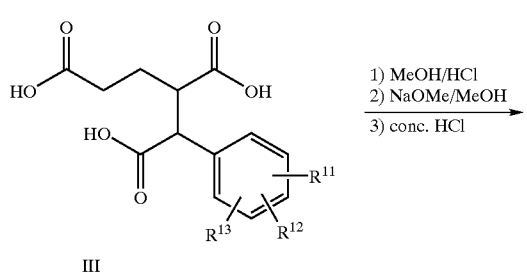

III

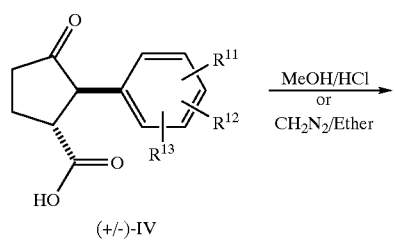

(+/-)-IV

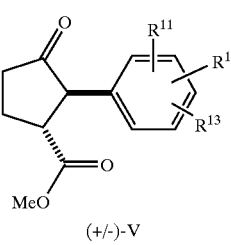

(+/-)-V

SCHEME 2

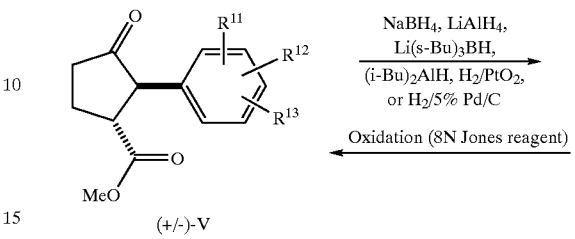

(+/-)-V

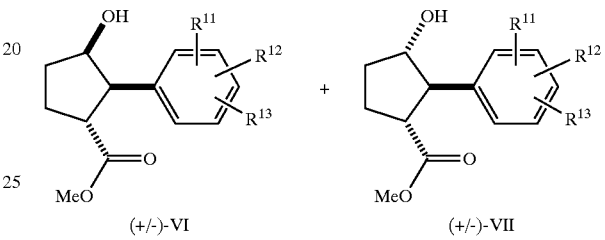

(+/-)-VI    (+/-)-VII

1) NaOH
2) HCl
3) S-(-)-α-methyl-benzylamine
4) Fractional crystallization
5) HCl 1) NaOH
2) HCl
3) R-(+)-α-methyl-benzylamine
4) Fractional crystallization
5) HCl

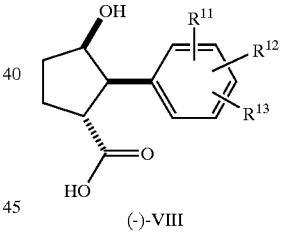 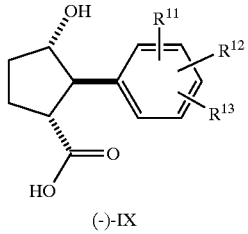

(-)-VIII    (-)-IX

Intermediates for preparation of the compounds of the present invention in which the central ring is 5-membered may be synthesized by the general route outlined in Scheme 1. Thus, according to the procedure of Baker and Leeds (*J. Chem. Soc* 1948, 974), condensation of ethyl cyanoacetate and benzaldehyde (with or without substituents) in the presence of a base such as piperidine provides the unsaturated derivative I. Exposure of this olefin to sodium cyanide followed by ethyl 3-chloropropionate gives the dicyano derivative II which after aqueous acidic hydrolysis yields triacid III. After esterification with acidic methanol, the triester may be cyclized by heating with sodium methoxide in dry methanol followed by treatment with aqueous hydrochloric acid, to provide racemic cyclopentanone IV. The methyl ester V may be formed from ketone IV by treatment with acidic methanol or diazomethane in ether.

The reduction of ester V may be accomplished with various reducing agents, for example, sodium borohydride, lithium aluminum hydride, di-isobutyl aluminum hydride, lithium tri(sec-butyl)-borohydride and the like, or with hydrogen in the presence of a suitable catalyst, such as platinum oxide or 5% palladium on carbon, which provide the corresponding cis- and trans- alcohols VI and VII, respectively (Scheme 2). The ratio of VI to VII thus obtained is dependent on the reducing agent employed. Alcohols VI and VII may be interconverted by oxidation to ketone V with chromium trioxide, pyridinium chlorochromate, DMSO/oxalyl chloride/triethylamine or similar agents followed by reduction with one of the reagents given above. Separation of the enantiomers of esters VI and VII may be carried out by hydrolysis to the corresponding acids VII and IX followed by fractional crystallization of the salts formed with R-(+)- or S-(–)-α-methylbenzylamine or other suitable chiral, non-racemic bases.

esterified with methanol to provide the separate enantiomers of esters VI and VII.

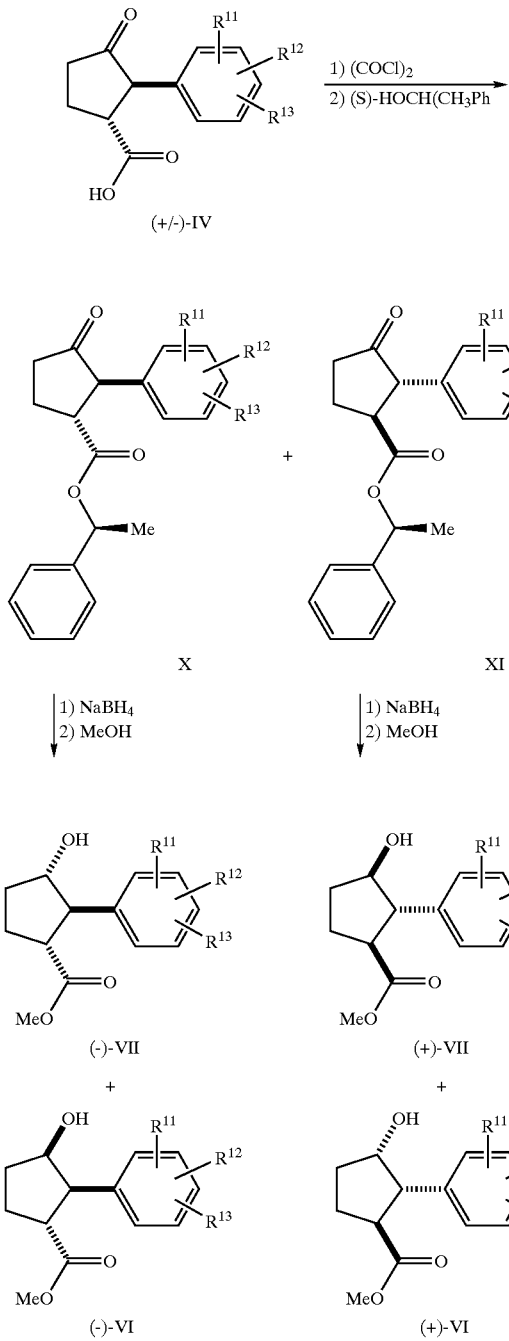

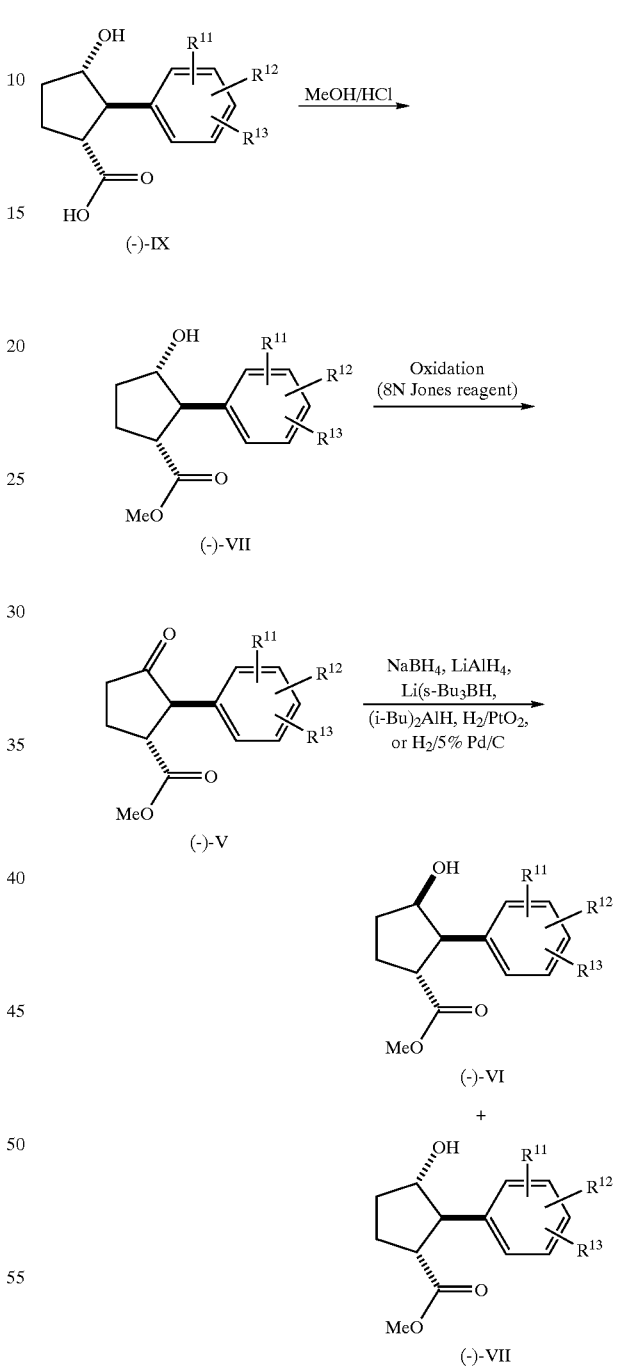

An alternative method of resolution is shown in Scheme 3. The racemic acid (+/−)-IV is activated with, for example, oxalyl chloride, DCC, EDAC/HOBt or similar condensing reagents, and then allowed to react with a chiral, non-racemic alcohol, such as (S)-alpha-methylbenzyl alcohol, to give the esters X and XI. After separating these diastereomers, they are individually treated with a suitable reducing agent, such as sodium borohydride, to give mixtures of the corresponding alcohols, which are then trans- Conversion of the free acids to the methyl esters is accomplished as shown in Scheme 4. Interconversion of the non-racemic cis and trans alcohols VI and VII may be carried out by oxidation to the non-racemic ketone V followed by reduction with an appropriate reducing agent as given above.

SCHEME 5

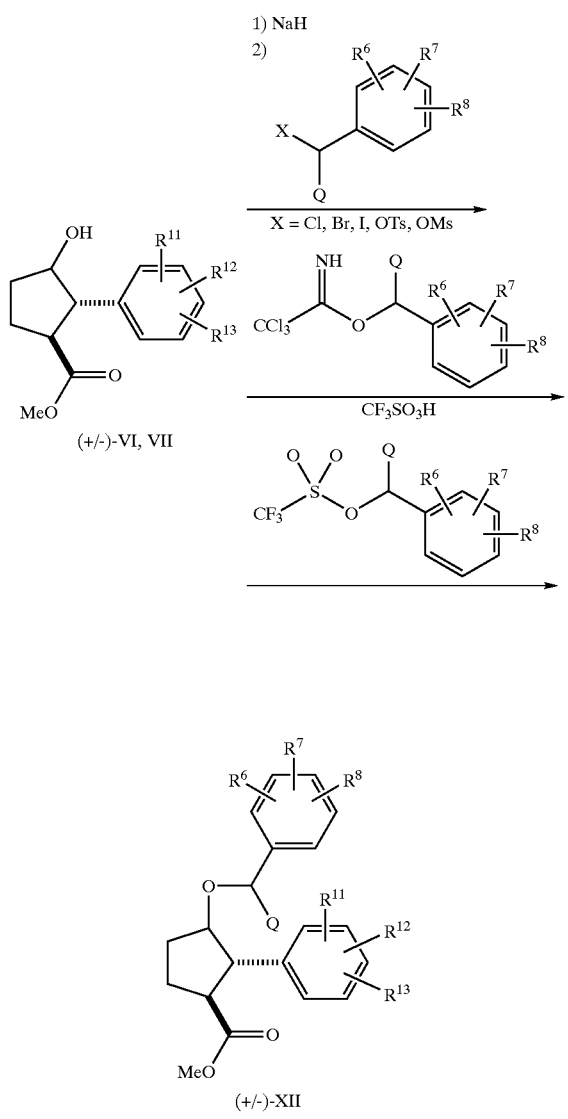

Q = H, C₁–C₄ alkyl

SCHEME 6

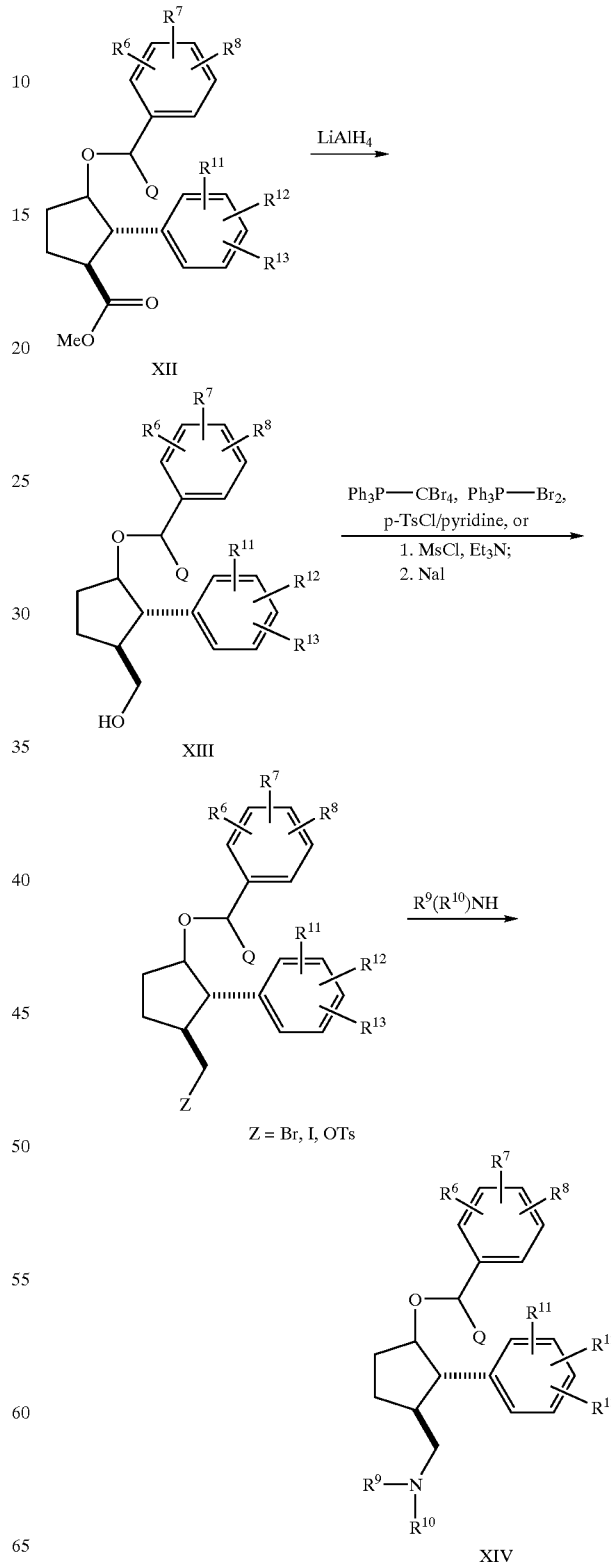

As shown in Scheme 5, O-alkylation of alcohols VI and VII may be carried out by several procedures, for example, treatment with sodium hydride followed by addition of a benzylic halide, alkylsulfonate or arylsulfonate; exposure of VI or VI to a benzylic trichloroacetimidate in the presence of a strong acid such as trifluoromethanesulfonic acid; or treatment with a benzylic trifluoromethanesulfonic ester, to give ether XII.

Ester XII may be reduced with a hydride-reducing agent such as lithium aluminum hydride, lithium borohydride or di-isobutylaluminum hydride to provide the primary alcohol XIII, which may be further functionalized by standard acylation or etherification, reactions (Scheme 6). Alternatively, the hydroxyl group may be replaced by a leaving group such as a bromide (by exposure to triphenylphosphine-bromine or triphenylphosphine-carbon tetrabromide), an iodide (by treatment with methanesulfonyl chloride followed by sodium iodide) or a p-toluenesulfonate (by treatment with p-TsCl in the presence of a suitable base such as pyridine). The leaving group may then be displaced by a variety of nucleophiles such as unsubstituted, mono- or disubstituted amines $R^9(R^{10})NH$, to give amine XIV.

SCHEME 7

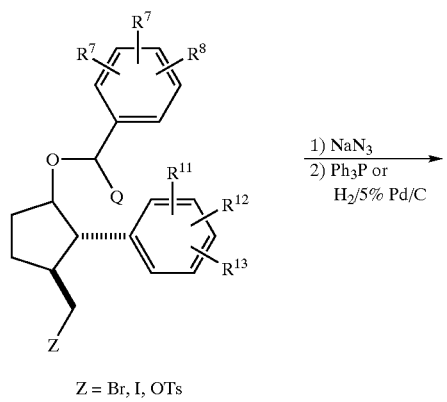

Z = Br, I, OTs

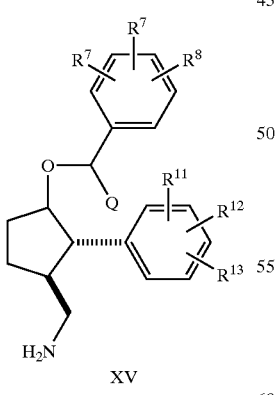

XV

SCHEME 8

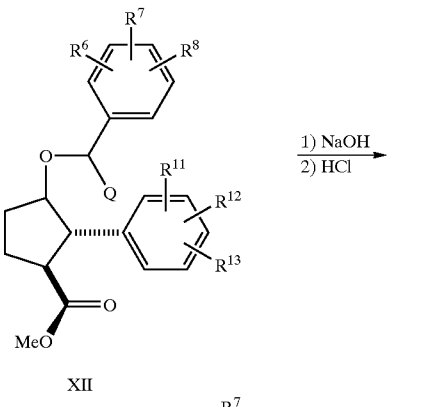

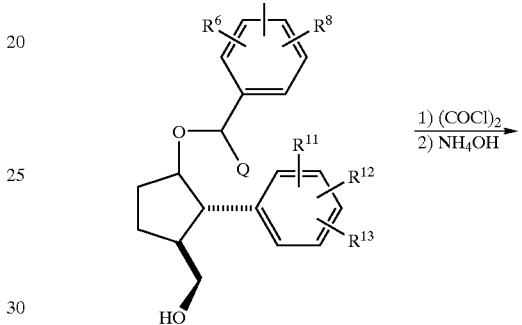

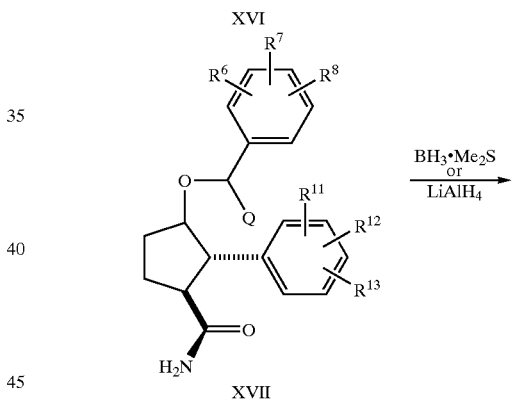

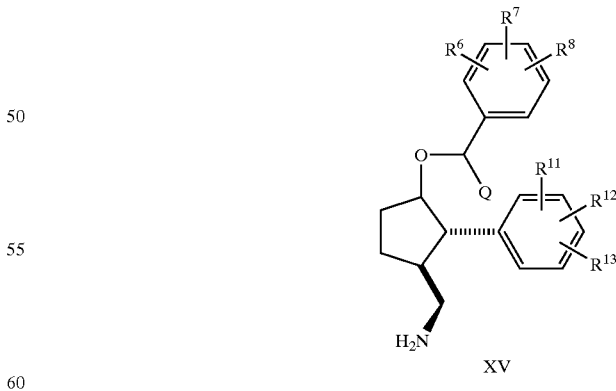

XV

Alternatively, as shown in Scheme 7 the leaving group may be displaced by azide anion and the azide group reduced by treatment with either triphenylphosphine/water or hydrogenation in the presence of a suitable metal catalyst to give the primary amine XV.

Primary amine XV may also be prepared by the route shown in Scheme 8. Hydrolysis of ester XII to the acid XVI, followed by formation of the acid chloride and exposure to aqueous ammonia, provides primary amide XVII. Reduction with borane-methyl sulfide, lithium aluminum hydride, or a similar reagent then gives amine XV.

SCHEME 9

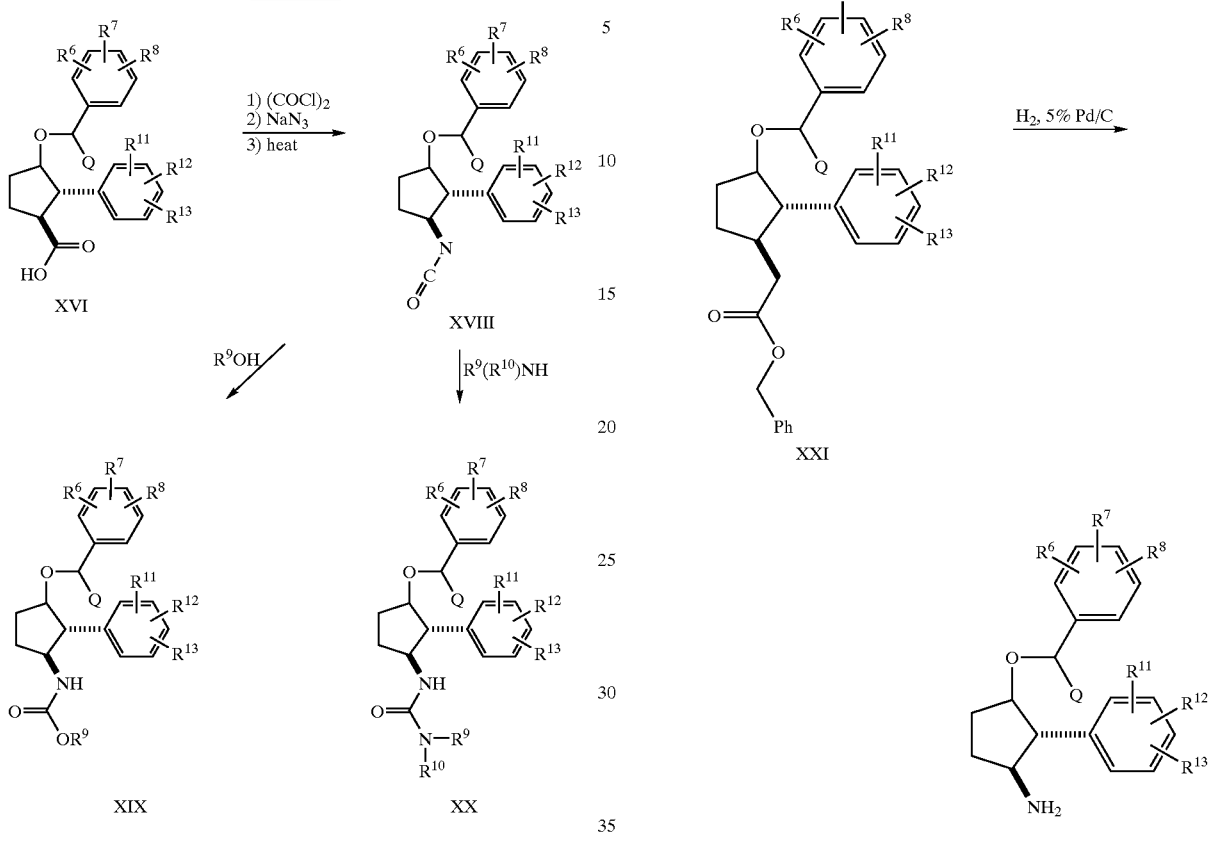

Treatment of acid XVI with oxalyl chloride and then sodium azide provides the corresponding acyl azide, which upon thermolysis provides isocyanate XVIII (Scheme 9). Treatment of XVIII with an alcohol $R^9OH$ gives the carbamate XIX, while reaction of XVIII with an amine $R^9(R^{10})$NH provides the urea XX.

In the specific case where $R^9OH=PhCH_2OH$, the CBZ-protected amine XXI is obtained, which may be de-protected under standard conditions (for example, $H_2$, 10% Pd/C) to afford primary amine XXII (Scheme 10).

SCHEME 10

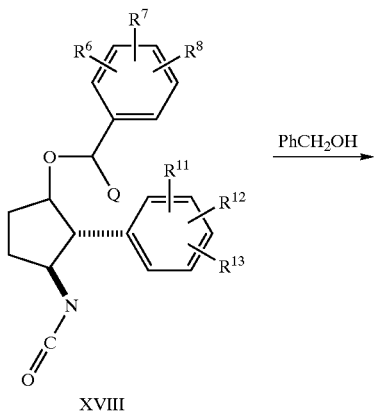

SCHEME 11

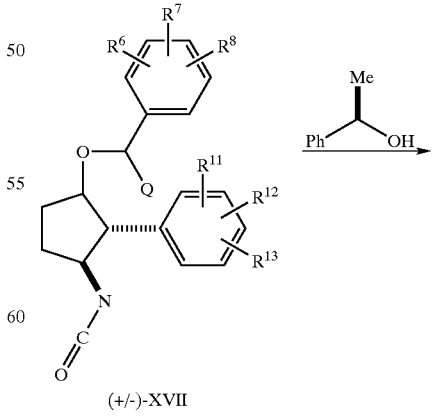

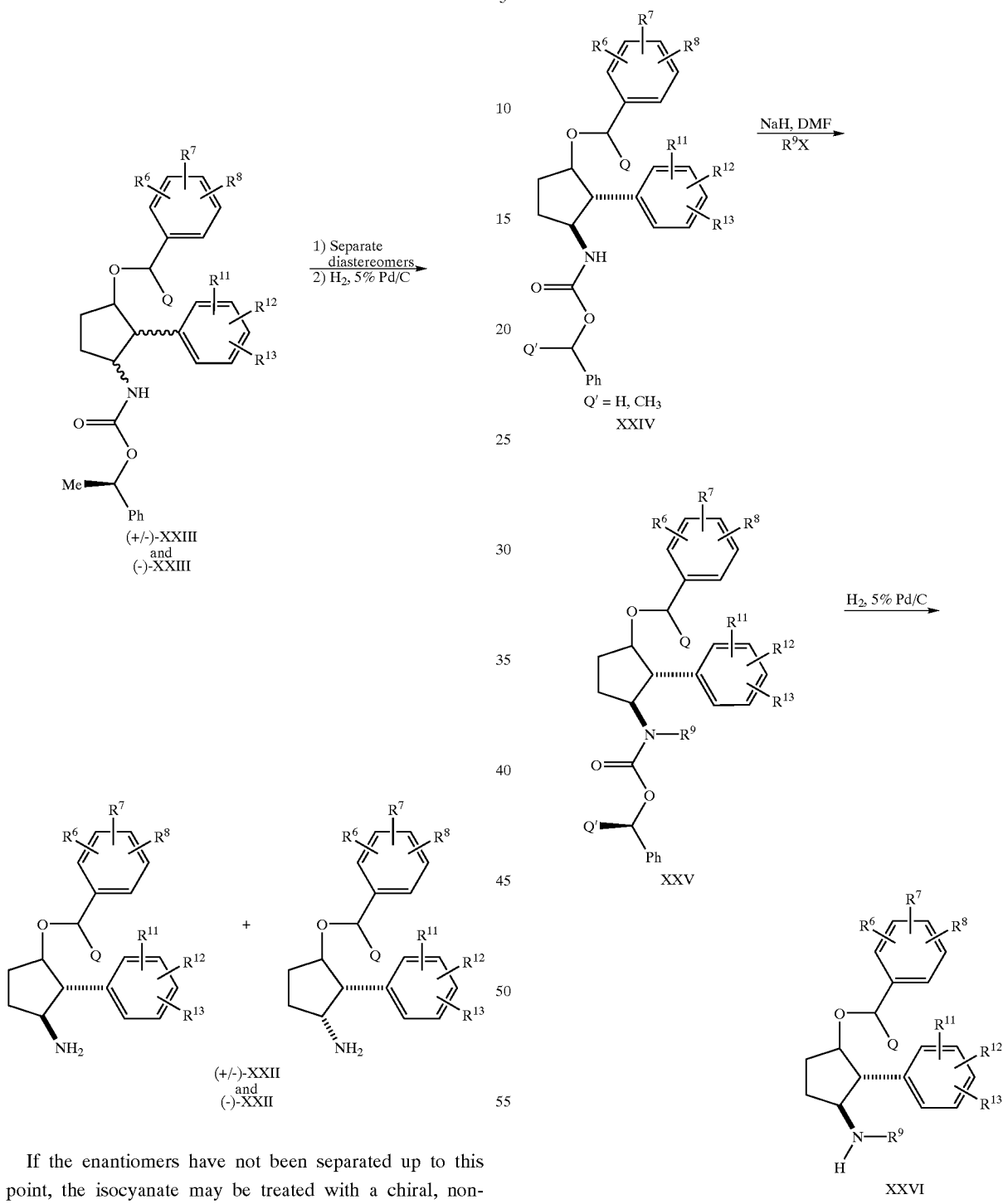

If the enantiomers have not been separated up to this point, the isocyanate may be treated with a chiral, non-racemic alcohol such as (R)-(+)-alpha-methylbenzyl alcohol to form diastereomeric carbamates XXIII, which after diastereomer separation by, for example, fractional crystallization or chromatography, may be converted to the non-racemic primary amine XXII by reduction or hydrolysis (Scheme 11).

Alkylation of carbamate XXIV may be carried out by treatment with a suitable base such as sodium hydride followed by addition of an alkylating agent $R^9X$, where X=Cl, Br, I, OMs, or OTs, to afford XXV (Scheme 12). Cleavage of the carbamate under conditions described previously gives secondary amine XXVI.

SCHEME 13

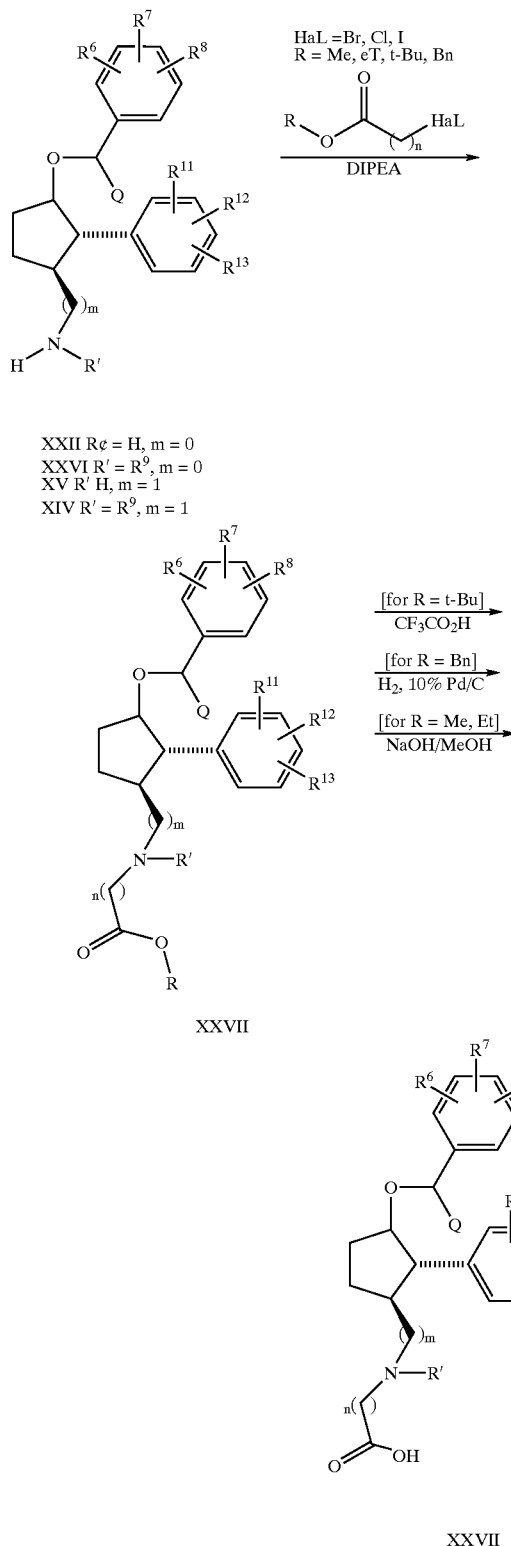

XXII R¢ = H, m = 0
XXVI R' = R⁹, m = 0
XV R' H, m = 1
XIV R' = R⁹, m = 1

Alkylation of amines XXII, XXVI, XV or XIV may be carried out by treatment with a number of reagents, such as t-butyl or benzyl bromoacetate or chloropropanoate (Scheme 13). The t-butyl esters XXVII (R=t-Bu) may be cleaved by exposure to trifluoroacetic acid to provide the carboxylic acid XXVII, while esters XXVII (R=Bn) may be converted to the acids XXVIII by hydrogenolysis and esters XXVII (R=Me or Et) may be converted to the acids XXVIII by basic hydrolysis.

SCHEME 14

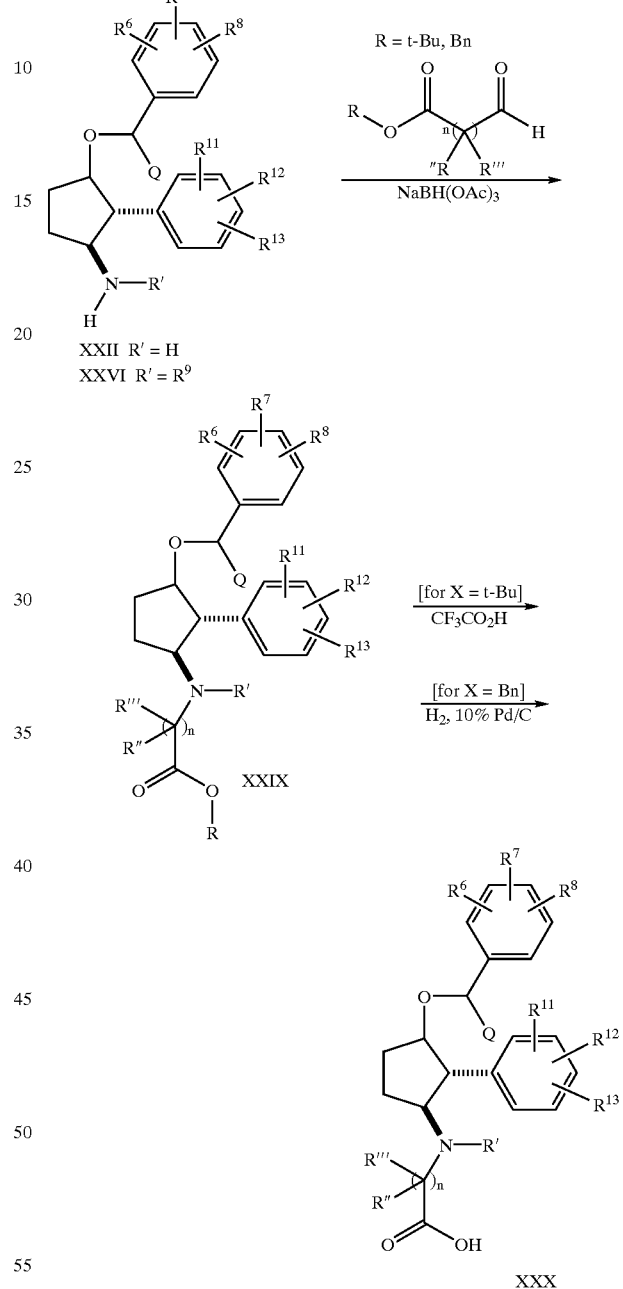

XXII R' = H
XXVI R' = R⁹

Alkylation of amine XXII or amine XXVI may also be carried out by reductive amination with an appropriate aldehyde in the presence of a reducing agents such as sodium triacetoxyborohydride in DCE or sodium cyanoborohydride in methanol (Scheme 14). The reductive amination can also be done catalytically with 10% palladium on carbon in methanol. The t-butyl esters XXIX (R=t-Bu) may be cleaved by exposure to trifluoroacetic acid to provide the carboxylic acid XXX, while esters XXIX (R=Bn) may be converted to the acids XXX by hydrogenolysis.

SCHEME 15

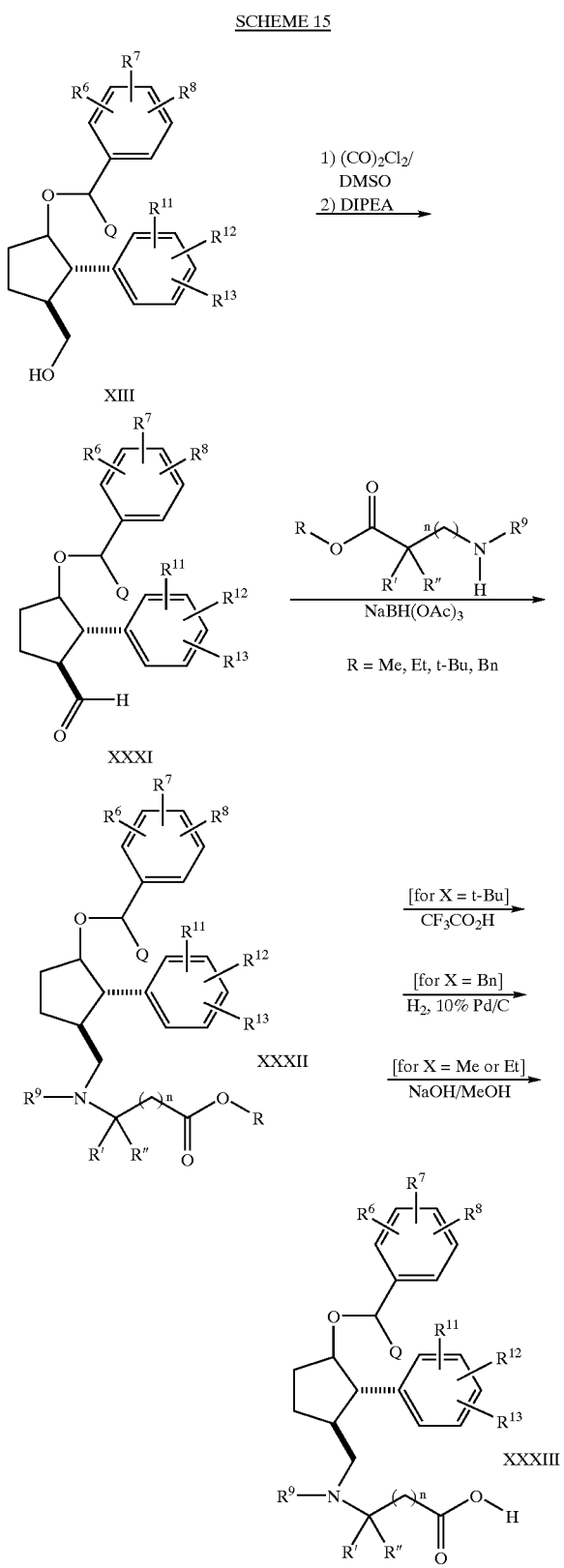

15). Reductive amination of primary or secondary amines with XXXI to afford amino-esters XXXII can be carried out in the presence of reducing agents such as sodium triacetoxyborohydride in DCE or sodium cyanoborohydride in methanol. The reductive amination can also be done catalytically with 10% palladium on carbon in methanol. The esters XXXII may be cleaved to the corresponding acids XXXIII as previously described depending on R.

SCHEME 17

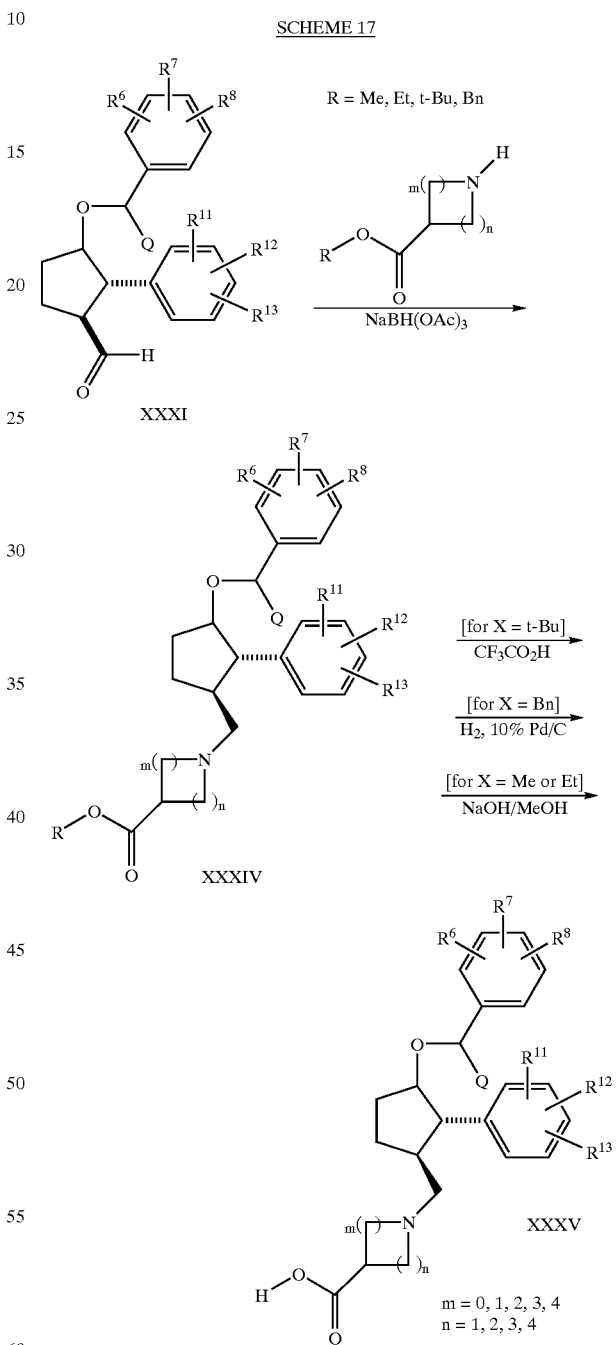

Oxidation of alcohol XIII (Scheme 6) to aldehyde XXXI can be accomplished with oxalyl chloride/DMSO/DIPEA in methylene chloride (Swern oxidation) or similar oxidation routes which stop at the aldehyde oxidation state (Scheme 15).

Reductive amination of cyclic amines with XXXI to afford amino-esters XXXIV can be carried in the presence of a reducing agents such as sodium triacetoxyborohydride in DCE or sodium cyanoborohydride in methanol (Scheme 17). The esters XXXII may be cleaved to the corresponding acids XXXV as previously described depending on R.

SCHEME 18

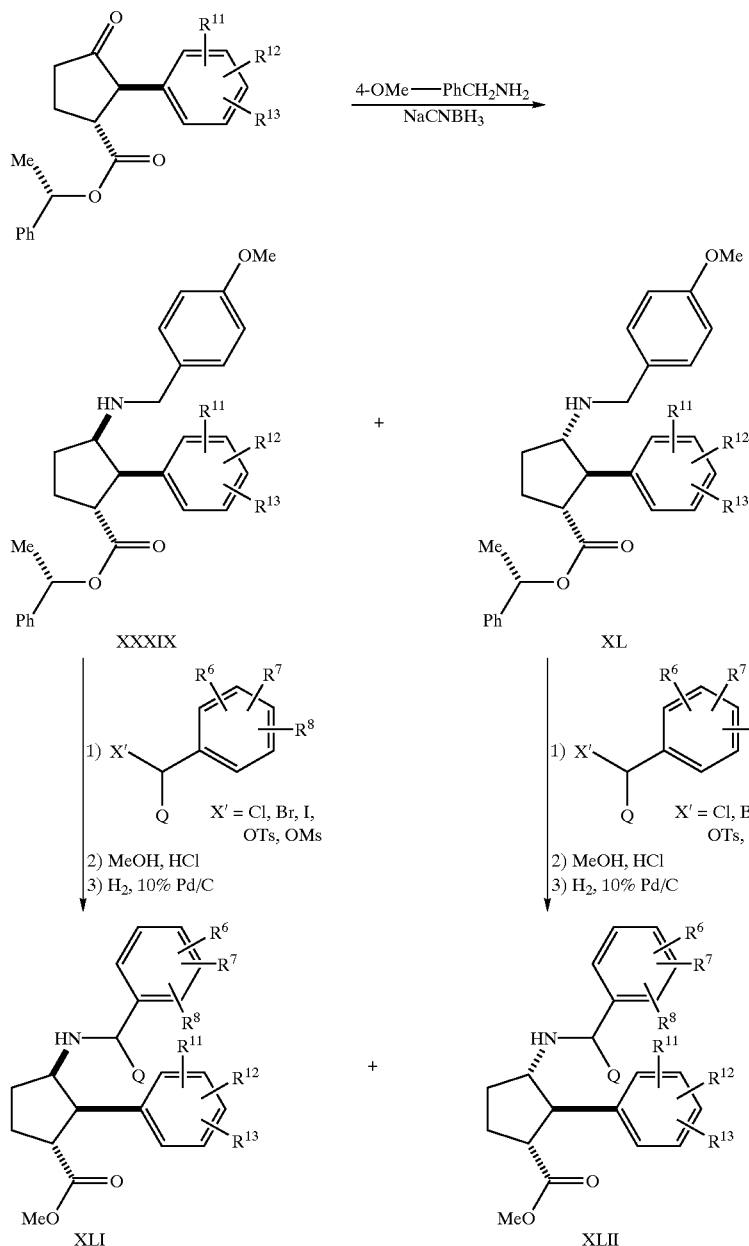

Benzylamine derivatives may be prepared as shown in Scheme 18. Treatment of ketone X with 4-methoxybenzylamine in the presence of a suitable reducing agent such as sodium cyanoborohydride provides a mixture of the cis and trans amines XXXIX and XL. Alkylation with a benzyl halide, benzyl alkylsulfonate or benzyl arylsulfonate followed by acidic methanolysis and then hydrogenolysis with 10% Pd/C provides the N-benzylated derivatives XLI and XLII.

SCHEME 21

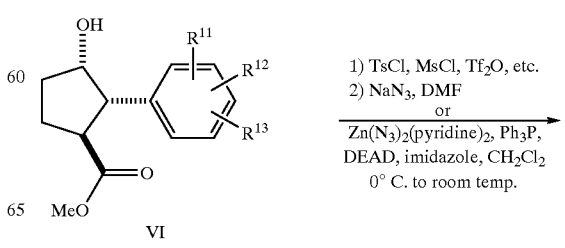

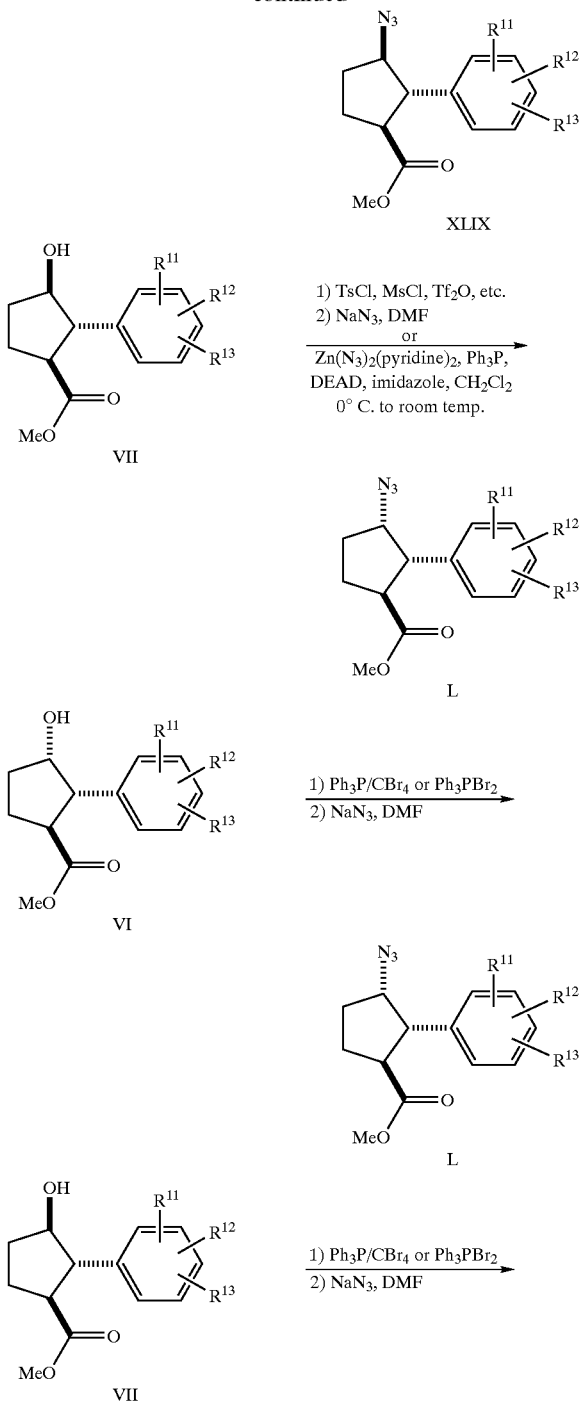

p-toluenesulfonyl chloride, methanesulfonyl chloride, trifluoromethane sulfonic anhydride, or similar agents, followed by treatment with sodium azide in DMF, provides the azide XLIX or L, respectively, in which the stereochemistry of the starting hydroxyl group has been inverted. Alternatively, activation of the alcohol VI or VII with a halogenating agent, for example triphenylphosphine/carbon tetrabromide or triphenylphosphine dibromide, followed by displacement with azide, results in formation of azides XLIX or L with overall retention of hydroxyl stereochemistry. Another method to produce the azide with inversion of stereochemistry involves treating the alcohol with triphenylphosphine, diethyl azodicarboxylate and zinc azide bis(pyridine) complex, in the presence of 2 equivalents of imidazole.

SCHEME 22

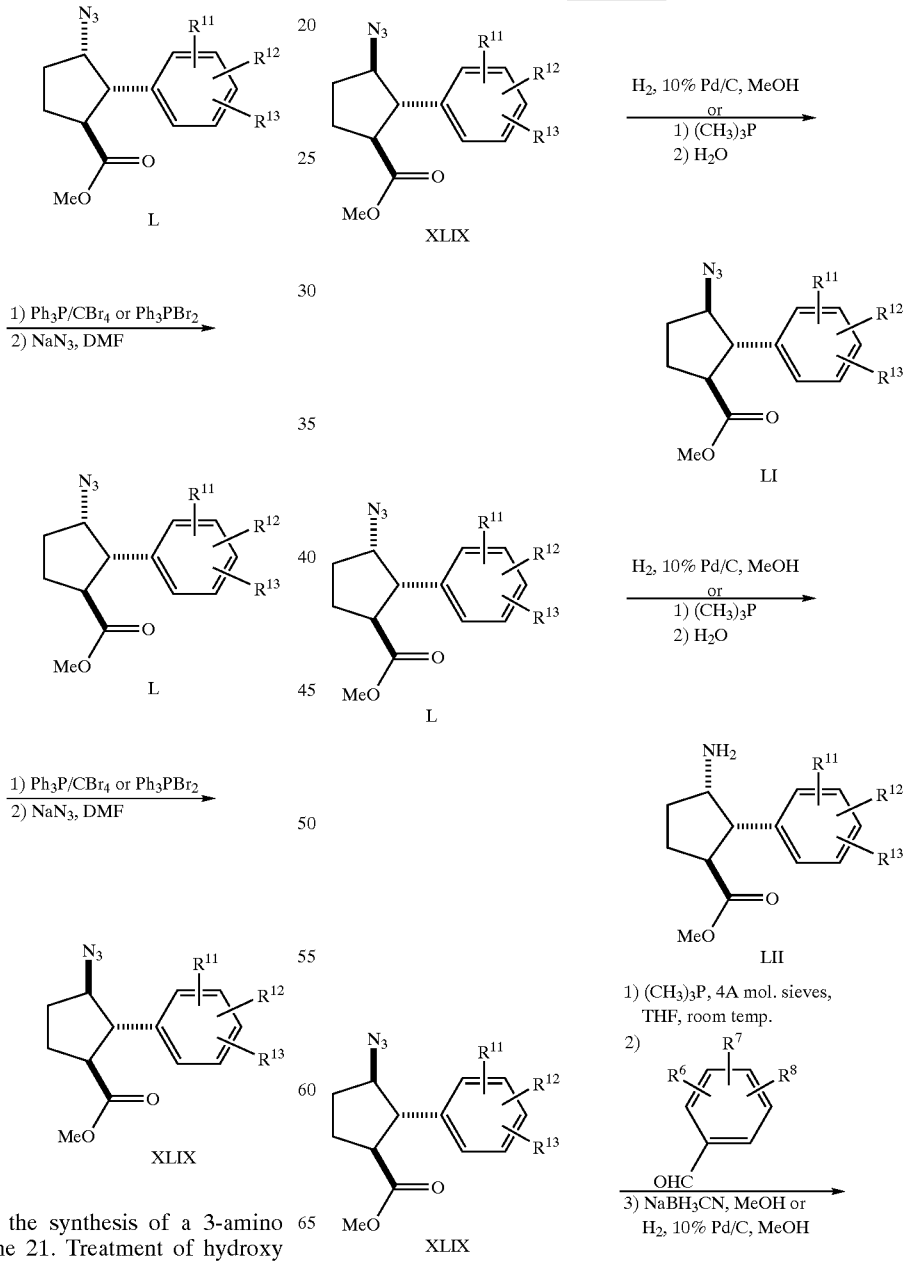

An alternative method for the synthesis of a 3-amino derivative is shown in Scheme 21. Treatment of hydroxy esters VI or VII with an activating agent, such as

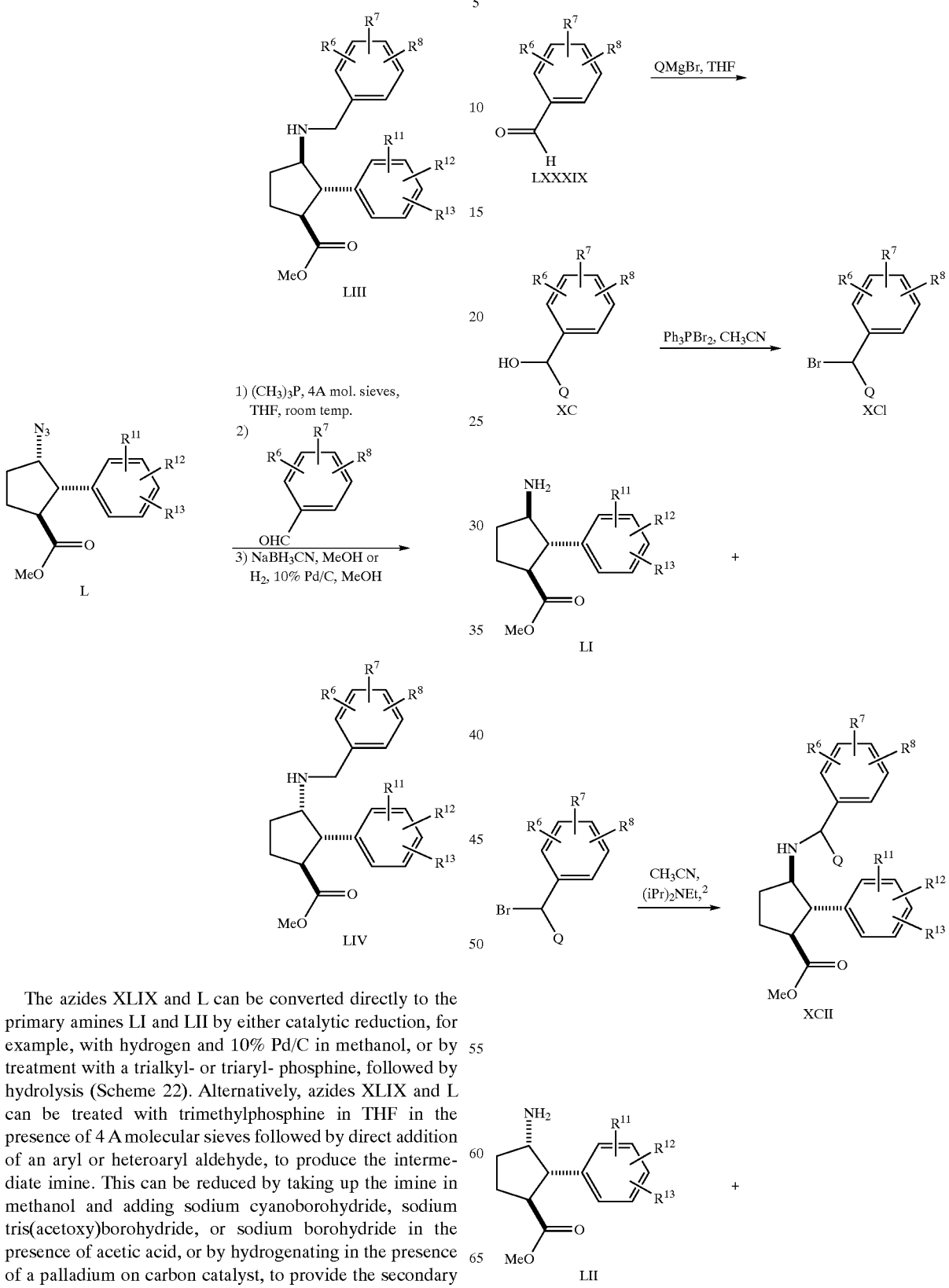

The azides XLIX and L can be converted directly to the primary amines LI and LII by either catalytic reduction, for example, with hydrogen and 10% Pd/C in methanol, or by treatment with a trialkyl- or triaryl- phosphine, followed by hydrolysis (Scheme 22). Alternatively, azides XLIX and L can be treated with trimethylphosphine in THF in the presence of 4 A molecular sieves followed by direct addition of an aryl or heteroaryl aldehyde, to produce the intermediate imine. This can be reduced by taking up the imine in methanol and adding sodium cyanoborohydride, sodium tris(acetoxy)borohydride, or sodium borohydride in the presence of acetic acid, or by hydrogenating in the presence of a palladium on carbon catalyst, to provide the secondary amine LIII and LIV, respectively.

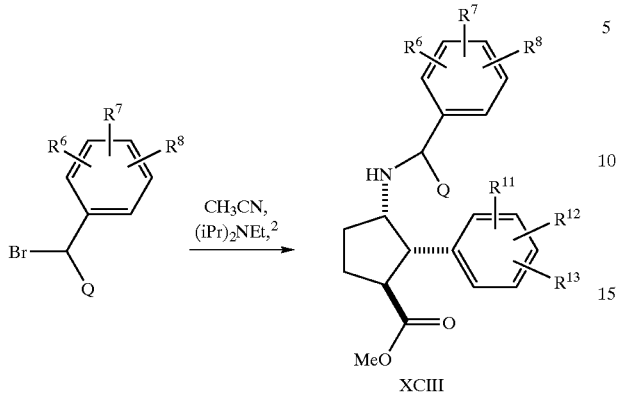

Preparation of derivatives wherein an alkyl chain Q is present at the benzylic position are prepared according to the procedure in Scheme 23. Addition of an alkyl magnesium halide or alkyllithium reagent to the aldehyde intermediate LXXXIX provides secondary alcohol XC. Conversion of the hydroxyl group to a leaving group, for example by formation of the tosylate, mesylate, triflate, bromide or iodide produces an intermediate XCI (when the leaving group is bromide) that can be used to alkylate amines LI and LII in refluxing acetonitrile in the presence of a suitable hindered amine base, such as DIEA, to give XCII and XCIII, respectively.

SCHEME 24

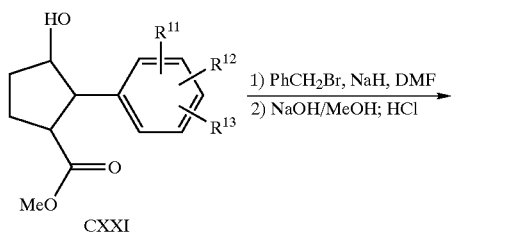

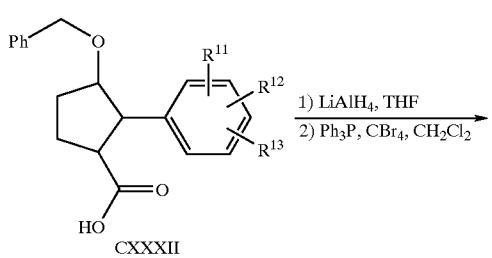

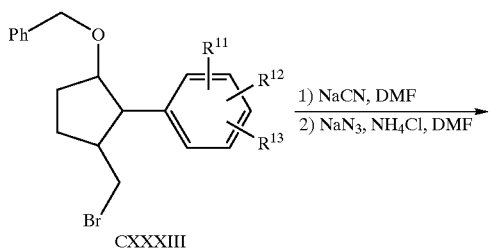

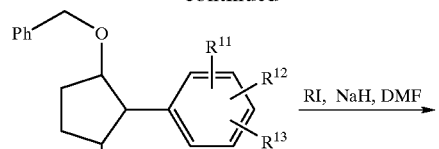

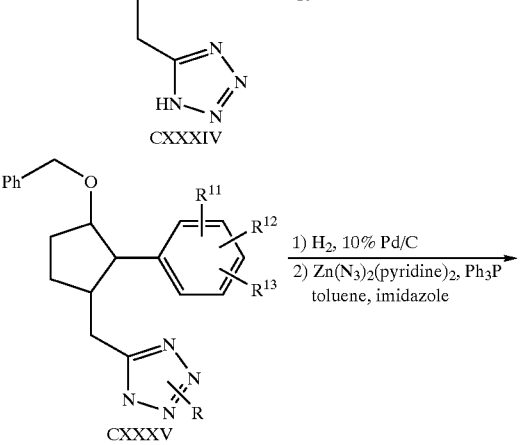

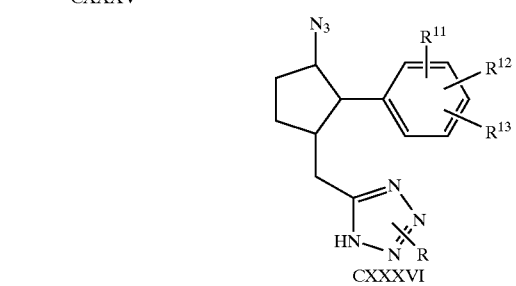

Preparation of intermediates which lead to analogs where Y is a methylene group, Z is absent and $R^3$ is an N-alkyl tetrazo-5-yl group is shown in Scheme 24. Protection of the hydroxyl group of ester CXXI followed by basic hydrolysis gives benzyl ether CXXXII. Reduction with lithium aluminum hydride and then treatment with triphenylphosphine and carbon tetrabromide affords bromide CXXXIII. Displacement with sodium cyanide and then treatment with sodium azide in the presence of ammonium chloride in DMF provides tetrazole CXXXIV. Alkylation under basic conditions provides a mixture of 1-alkyl- and 2-alkyl tetrazoles CXXXV, which can be converted to the desired azide intermediates by hydrogenolytic deprotection and then by treatment with zinc diazide bis(pyridine) complex and imidazole in the presence of diethylazodicarboxylate and triphenylphosphine to provide azido tetrazoles CXXXVI.

It is noted that in some cases the order of carrying out the foregoing reaction schemes may be varied to facilitate the reaction or to avoid unwanted reaction products.

Tachykinin Antagonism Assay

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSClENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-Sp and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

In particular, the intrinsic tachykinin receptor antagonist activities of the compounds of the present invention may be demonstrated by this assay. The compounds of the following examples have activity in the aforementioned assay in the range of 0.05 nM to 10 $\mu$M. The activity of the present compounds may also be demonstrated by the assay disclosed by Lei, et al., *British J. Pharmacol.*, 105, 261–262 (1992).

With respect to the compounds disclosed in U.S. Pat. Nos. 5,387,595, 5,750,549 and *Bioorg. & Med. Chem. Lett.*, 1345 (1995), the present compounds exhibit unexpected properties, such as with respect to duration of action and/or metabolism, such as enhanced oral bioavailability or absorption.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of the present invention are also of value in the treatment of a combination of the above conditions, in particular in the treatment of combined post-operative pain and post-operative nausea and vomiting.

The compounds of the present invention are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of the present invention are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of the present invention are also of use in the treatment of emesis induced by radiation including radiation therapy such as in the treatment of cancer; and in the treatment of post-operative nausea and vomiting.

It will be appreciated that the compounds of the present invention may be presented together with another therapeutic agent as a combined preparation for simultaneous, separate or sequential use for the relief of emesis. Such combined preparations may be, for example, in the form of a twin pack.

A further aspect of the present invention comprises the compounds of the present invention in combination with a 5-$HT_3$ antagonist, such as ondansetron, granisetron or tropisetron, or other anti-emetic medicaments, for example, a dopamine antagonist such as metoclopramide or domperidone or $GABA_B$ receptor agonists such as baclofen. Additionally, a compound of the present invention, either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of the present invention may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of the present invention are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The compounds of the present invention are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of the present invention for use in therapy.

According to a further or alternative aspect, the present invention provides a compound of the present invention for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The present invention is further directed to a method for the manufacture of a medicament for antagonizing the effect of substance P or another tachykinin at its receptor site or for the blockade of neurokinin-1 receptors or other tachykin receptors in a mammal comprising combining a compound of the present invention with a pharmaceutical carrier or diluent.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a further aspect of the present invention, it may be desirable to treat any of the aforementioned conditions with a combination of a compound according to the present invention and one or more other pharmacologically active agents suitable for the treatment of the specific condition. The compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above.

Also, for the treatment of respiratory diseases, such as asthma, a compound of the present invention may be used in conjunction with a bronchodilator, such as a $\beta_2$-adrenergic receptor agonist or a tachykinin antagonist which acts at neurokinin-2 receptors. Suitable β2-adrenergic receptor agonist include: Bambuterol (U.S. Pat. No. 4,419,364 issued to Draco on Dec. 6, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 2, 1973); Clenbuterol (U.S. Pat. No. 3,536,712 issued to Boehringer Ingelheim Oct. 4, 1970); Cimaterol (U.S. Pat. No. 4,407,819 issued to American Cyanamid Oct. 4, 1983); Docarpamine (U.S. Pat. No. 4,228,183 issued to Tanabe Oct. 14, 1980); Dopexamine (U.S. Pat. No. 4,645,768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. Pat. No. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exemplified by those disclosed in Patent Pub. EP O,480,717, published Apr. 15, 1992; Patent Pub. EP O 604,114, published June 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in conjunction with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

The present invention accordingly provides a method for the treatment of a respiratory disease, such as asthma, which method comprises administration to a patient in need thereof of an effective amount of a compound of the present invention and an effective amount of a bronchodilator.

The present invention also provides a composition comprising a compound of the present invention, a bronchodilator, and a pharmaceutically acceptable carrier.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

It will be appreciated that for the treatment or prevention of migraine, a compound of the present invention may be used in conjunction with other anti-migraine agents, such as ergotamines or $5\text{-}HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of the present invention, a bronchodilator, and a pharmaceutically acceptable carrier.

It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5-HT_{1A}$ agonists or antagonists, especially $5-HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5-HT_{1A}$ receptor agonists or antagonists include, in particular, the $5-HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of the present invention and an anorectic agent for the manufacture of a medicament for the treatment or prevention of eating disorders.

The present invention also provides a method for the treatment or prevention of eating disorders, which method comprises administration to a patient in need of such treatment an amount of a compound of the present invention and an amount of an anorectic agent, such that together they give effective relief.

In a further aspect of the present invention, there is provided a pharmaceutical composition comprising a compound of the present invention and an anorectic agent, together with at least one pharmaceutically acceptable carrier or excipient.

It will be appreciated that the compound of the present invention and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of the present invention and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of the present invention and an SSRI for the manufacture of a medicament for the treatment or prevention of obesity.

The present invention also provides a method for the treatment or prevention of obesity, which method comprises administration to a patient in need of such treatment an amount of a compound of the present invention and an amount of an SSRI, such that together they give effective relief.

In a further aspect of the present invention, there is provided a pharmaceutical composition for the treatment or prevention of obesity comprising a compound of the present invention and an SSRI, together with at least one pharmaceutically acceptable carrier or excipient.

It will be appreciated that the compound of the present invention and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of the present invention and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention"(of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention further relates to the use of a compound of the present invention for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of the present invention or a pharmaceutically acceptable salt thereof.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of achykinins, a suitable dosage level is about 0.001 to 50 mg/kg per day, in particular bout 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

The following examples are provided for the purpose of further illustration only and are not intended to be limitations on the disclosed invention.

EXAMPLE 1

Methyl 3-(SR)-(3,5-bis(trifluoromethyl)phenyl)methoxy)-2-(RS)-phenylcyclopentane-1-(RS)-carboxylate (Racemic 2,3-trans isomer)

The title compound was prepared as shown in Scheme 1 and using the procedures of W. Baker and W. G. Leeds, J. Chem. Soc. 974 (1948).

Step A: γ-δ-Dicarboxy-δ-phenyl-n-valeric acid

A mixture of 47 g of benzaldehyde and 50 g of ethyl cyanoacetate in 200 mL of absolute ethanol was treated with 2 mL of piperidine and the reaction was gently warmed. After the initial exothermic reaction had subsided, the reaction was heated to 60° C. (internal temperature) and then allowed to cool to room temperature. After 1 hour, 22 g of powdered sodium cyanide was added in portions over 25 minutes and a mild exotherm ensued. The reaction was heated to an internal temperature of 80° C. and then allowed to cool to 35° C. before slow addition of 60 g of ethyl β-chloropropionate over 10 minutes. After heating in an oil bath at 80° C. for 5 hours, the reaction was cooled and filtered to remove the precipitated sodium chloride. The filtrate was concentrated and to the residue was added 500 mL of concentrated hydrochloric acid and 250 mL of water. The mixture was heated at reflux for 48 hours and, while still hot, was treated with charcoal and filtered through Celite to remove some insoluble tarry material. On cooling, 25.8 g of title compound as a pale yellow solid was obtained after filtration and air drying. The filtrate was extracted with ethyl acetate, washed with brine, dried with sodium sulfate and evaporated to provide an additional 32.8 g of less pure product which could be used directly.

Step B: Trimethyl γ-δ-dicarboxy-δ-phenyl-n-valerate

Into a solution of 21.2 g of the above triacid dissolved in 200 mL of methanol was bubbled 48.6 g of hydrogen chloride gas. After heating at reflux overnight, the cooled reaction was concentrated and diluted with toluene. Most of the aqueous bottom phase was removed via pipette and the toluene was evaporated. The residue was taken up in 200 mL of methanol and resaturated with hydrogen chloride gas (53.5 g). After heating for another 20 hours, the reaction was concentrated and the residue was dissolved in ether and washed with water, saturated sodium bicarbonate, and brine, then dried with sodium sulfate, and evaporated to provide 25.7 g of an oil which crystallized in the freezer. Trituration with 5% ethyl acetate in hexanes and filtration gave 18.4 g of the title triester as a white solid.

Step C: trans-(+/−)-2-Phenylcyclopentan-3-one-1-carboxlic acid

To 50 mL of anhydrous methanol was added a solution of 26 mL of 25% by wt sodium methoxide in methanol followed by 18.4 g of the above triester dissolved in 25 mL of methanol. After heating at reflux for 5.5 hours, the solvent was evaporated and the residue was dissolved in 150 mL of concentrated hydrochloric acid and 75 mL of water and heated at reflux overnight. The reaction, while still hot, was treated with charcoal and filtered through Celite. After cooling, 7.65 g of title compound was obtained as a white solid after filtration and air drying. An additional 4.76 g of triacid was recovered by extraction of the filtrate with ethyl acetate.

Step D: Methyl trans-(+/−)-2-phenylcyclopentan-3-one-1-carboxylate

A solution of 4.17 g of above acid in 200 mL of methanol was saturated with hydrogen chloride gas and stirred overnight. The reaction was concentrated to a wet solid. This was taken up in ethyl acetate and washed with water, saturated sodium bicarbonate solution, and brine, then dried with sodium sulfate and evaporated to furnish 4.4 g of the title product as a white solid. NMR (CDCl$_3$): δ2.0–2.15 (m, 1H), 2.3–2.5 (m, 2H), 2.62 (br dd, 1H), 3.25 (dt, 1H), 3.65 (s, 3H), 3.70 (br d, 1H), 7.12 (m, 2H), 7.24 (m, 1H), 7.32 (m, 2H).

Step E: Methyl 3-(SR)-(hydroxy)-2-(SR)-phenylcyclopentane-1-(SR)-carboxylate (Racemic 2,3-cis isomer) and methyl 3-(SR)-(hydroxy)-2-(RS)-phenylcyclopentane-1-(RS)-carboxylate (Racemic 2,3-trans isomer)

Method A

To a solution of 4.43 g of methyl trans-(+/−)-2-phenylcyclopentan-3-one-1-carboxylate from Example 1, Step D in 65 mL of absolute methanol cooled in an ice/ethanol bath was added 807 mg of sodium borohydride in portions. After 1 hour, the reaction was quenched with aqueous NH$_4$Cl. The solvent was evaporated and the residual oil was partitioned between ethyl acetate and water. The organic layer was washed with brine, dried with sodium sulfate and evaporated. The residue was purified by Prep LC eluting first with 20% ethyl acetate in hexanes to provide 1.18 g of the higher $R_f$ 2,3-cis isomer. NMR (CDCl$_3$): δ1.8–2.0 (m, 2 H), 2.05–2.2 (m, 1H), 2.3–2.4 (m, 1H), 3.3–3.45 (m, 2H), 3.59 (s, 3H), 4.30 (m, 1H), 7.2–7.35 (m, 5H).

Further elution with 40% ethyl acetate in hexanes provided 3.90 g of the lower $R_f$ 2,3-trans isomer. NMR (CDCl$_3$): δ1.82 (m, 1H), 2.10 (m, 3H), 2.95 (q, 1H), 3.22 (dd, 1H), 3.60 (s, 3H), 4.20 (q, 1H), 7.22 (m, 3H), 7.31 (m, 2H).

Method B

To a solution of 100 mg of methyl trans-(+/−)-2-phenylcyclopentan-3-one-1-carboxylate from Example 1, Step D in 5 mL of dry THF under N$_2$ and cooled in a dry ice/acetone bath was added dropwise 0.55 mL of 1M L-Selectride in THF. After 1 hour, the reaction was quenched with dilute hydrochloric acid. The mixture was extracted twice with ether and the organic layers were washed with brine, combined, dried with sodium sulfate and evaporated, The residue was purified by flash chromatography eluting with 20% ethyl acetate in hexanes to give only the higher $R_f$ 2,3-cis product isomer. The NMR was same as the higher $R_f$ isomer in Method A.

Step F: Methyl 3-(SR)-(3,5-bis(trifluoromethyl)phenyl) methoxy)-2-(RS)-phenylcyclopentane-1-(RS)-carboxylate (Racemic 2,3-trans isomer)

To a solution of 250 mg of the lower 2,3-trans alcohol from Example 1, Step E, Method A and 525 mg of 3,5-bis (trifluoromethyl)benzyl bromide in 5 mL of DMF at room temperature was added 91 mg of 60% sodium hydride in mineral oil. After 3 hours, the reaction was quenched with dilute hydrochloric acid and extracted twice with ether. The organic layers were washed with a portion of brine, combined, dried with sodium sulfate and evaporated. The residue was purified by flash chromatography eluting with 10 to 20% ethyl acetate in hexanes to obtain 230 mg of title compound. NMR (CDCl$_3$): δ1.85–2.0 (m, 1H), 2.0–2.2 (m, 3H), 2.90 (q, 1H), 3.46 (dd, 1H), 3.59 (s, 3H), 4.05 (q, 1H), 4.47 (ABq, 2H), 7.2–7.25 (m, 3H), 7.25–7.35 (m, 2H), 7.59 (s, 2H), 7.72 (s, 1H).

EXAMPLE 2

Methyl 3-(SR)-(3,5-bis(trifluoromethyl)phenyl) methoxy)-2-(SR)-phenylcyclopentane-1-(SR)-carboxylate (Racemic 2,3-cis isomer)

Using essentially the same procedure as in Example 1, Step F but using 200 mg of the higher 2,3-cis alcohol from Example 1, Step E, Method A, 250 mg of the title compound was obtained. NMR (CDCl$_3$): δ1.85–2.0 (m, 1H), 2.05–2.2 (m, 2H), 2.25–2.35 (m, 2H), 3.35–3.5 (m, 2H), 3.58 (s, 3H), 4.05 (m 1H), 4.10 (d, 1H), 4.43 (d, 1H), 7.2–7.35 (m, 5H), 7.41 (s, 2H), 7.68 (s, 1H).

EXAMPLE 3

3-(SR)-(3,5-Bis(trifluoromethyl)phenyl)methoxy)-2-(RS)-phenylcyclopentane-1-(RS)-carboxylic acid Racemic 2,3-trans isomer)

To a solution of 250 mg of methyl 3-(SR)-(3,5-bis (trifluoromethyl)phenyl)methoxy)-2-(RS)-phenylcyclopentane-1-(RS)-carboxylate from Example 1, Step F in 5 mL of ethanol was added 1.2 mL of 2N sodium hydroxide. The reaction was heated at 80° C. for 3 hours, cooled, diluted with water and acidified with 2N hydrochloric acid. The mixture was extracted twice with ether and the organic layers were washed with a portion of brine, combined, dried with sodium sulfate and evaporated. The residue was purified by flash chromatography eluting with 20% ethyl acetate in hexanes then 1% acetic acid in 20% ethyl acetate/hexanes to obtain 230 mg of title compound as a semi-solid.

EXAMPLE 4

1-(SR)-(3,5-Bis(trifluoromethyl)phenyl)methoxy-2-(SR)-phenyl-3-(RS)-(benzyloxycarbonylamino) cyclopentane Step A: 3-(SR)-(3,5-Bis(trifluoromethyl)phenyl)methoxy)-2-(SR)-phenylcyclopentyl-1-(RS)-isocyanate To a solution of 230 mg of the above carboxylic acid in 5 mL of methylene chloride containing a catalytic amount of DMF was added 0.10 mL of oxalyl chloride. The reaction was stirred at room temperature for 1 hour and evaporated to dryness. The above residue was taken up in 5 mL of acetone and cooled in an ice bath and a solution of 70 mg of sodium azide in 5 mL of water was added. The reaction was stirred for 0.5 hour, diluted with ice water and extracted twice with toluene. The organic layers were washed with a portion of brine, combined, dried with sodium sulfate and concentrated to 10 mL with a minimum of heating. (Note: The acyl azide is unstable and should not be concentrated to dryness.) The above solution was diluted with another 20 mL of toluene and heated at 80° C. for 1.5 hours and then concentrated to dryness. The residue (175 mg, single spot on TLC, 25% ethyl acetate in hexanes) was used directly in subsequent reactions.

Step B: 1-(SR)-(3,5-Bis(trifluoromethyl)phenyl)methoxy-2-(SR)-phenyl-3-(RS)-(benzyloxycarbonylamino) cyclopentane A solution of isocyanate prepared from 1.3 g of acid as in Step A, a catalytic amount of DMAP, 1 mL of DIPEA and 3 mL of benzyl alcohol in 3 mL of toluene was stirred at 80° C. for 20 hours. The volatiles were removed in vacuo and the residue was purified by flash chromatography eluting with 25% ethyl acetate in hexanes to obtain 1.10 g of title compound after precipitation from 10% ethyl acetate in hexanes. NMR (CDCl$_3$): δ1.7–1.85 (m, 1H), 1.85–2.0 (m, 1H), 2.0–2.2 (m, 1H), 2.2–2.4 (m, 1H), 2.90 (br t, 1H), 3.97 (dt, 1H), 4.1–4.2 (m, 1H), 4.54 (ABq, 2H), 4.83 (br d, 1H), 4.98 (ABq, 2H), 7.2–7.4 (m, 10H), 7.59 (s, 2H), 7.72 (s, 1H).

EXAMPLE 5

1-(SR)-(3,5-Bis(trifluoromethyl)phenyl)methoxy-2-(SR)-phenyl-3-(RS)-aminocyclopentane A solution of 200 mg of 1-(SR)-(3,5-bis(trifluoromethyl) phenyl)methoxy-2-(SR)-phenyl-3-(RS)-(benzyloxycarbonylamino)cyclopentane prepared in Example 4, Step B in 5 mL of methanol was hydrogenated over 50 mg of 10% Pd/C for 2 hours. The reaction was filtered and concentrated. The residue was purified on a 1 mm preparative silica gel plate eluted with 10% MeOH in ethyl acetate to obtain 120 mg of title compound. Mass spec (NH$_3$/CI): 404 (M+1).

EXAMPLE 6

1-(SR)-(3,5-Bis(trifluoromethyl)phenyl)methoxy-2-(SR)-phenyl-3-(RS)-(methylamino)cyclopentane Step A: 1-(SR)-(3,5-Bis(trifluoromethyl)phenyl)methoxy-2-(SR)-phenyl-3-(RS)-(N-(benzyloxycarbonyl)-N-methylamino) cyclopentane To a solution of 500 mg of benzyl carbamate prepared in Example 4, Step B and 0.12 mL of iodomethane in 5 mL of DMF was added 60 mg of 60% sodium hydride in mineral oil. After 2 hours, the reaction was quenched with 2N hydrochloric acid and water and extracted twice with ethyl acetate. The organic layers were washed with a portion of brine, combined, dried over sodium sulfate and evaporated. The residue was purified by flash chromatography eluting with 25% ethyl acetate in hexanes to obtain 500 mg of title compound as an oil. NMR (CDCl$_3$): δ1.80–2.0 (m, 3H), 2.0–2.2 (m, 1H), 2.80 and 2.87 (2 br s, 3H), 3.05–3.15 (m, 1H), 3.9–4.0 (m, 1H), 4.36 and 4.40 (2 s, 1H), 4.4–4.55 (m, 1H), 4.55–4.85 (2 br m, 1H), 4.91 and 5.03 (2 br s, 2H), 7.0–7.3 (m, 10H), 7.58 (br s, 2H), 7.72 (s, 1H).

Step B: 1-(SR)-(3,5-Bis(trifluoromethyl)phenyl)methoxy-2-(SR)-phenyl-3-(RS)-(methylamino)cyclopentane A solution of 475 mg of the above 1-(SR)-(3,5-bis(trifluoromethyl)-phenyl)methoxy-2-(SR)-phenyl-3-(RS)-(N-(benzyloxycarbonyl)-N-methylamino) cyclopentane in 5 mL of 1:1 methanol: ethyl acetate was hydrogenated over 100 mg of 10% Pd/C for 2 hours. The reaction was filtered and concentrated to afford the title compound as an oil. Mass spec (NH$_3$/CI): 418 (M+1).

EXAMPLE 7

Starting with the racemic 2,3-cis methyl ester from Example 2 and using essentially the same procedures as in Examples 3 thru 6, the following racemic 2,3-cis isomeric compounds were prepared:

3-(SR)-3,5-Bis(trifluoromethyl)phenyl)methoxy)-2-(SR)-phenylcyclopentane-1-(SR)-carboxylic acid 1-(SR)-(3,5-Bis(trifluoromethyl)phenyl)methoxy-2-(RS)-phenyl-3-(SR)-(benzyloxycarbonylamino)cyclopentane
Mass spec (NH$_3$/CI): 538 (M+1).

1-(SR)-(3,5-Bis(trifluoromethyl)phenyl)methoxy-2-(RS)-phenyl-3-(SR)-aminocyclopentane
Mass spec (NH$_3$/CI): 404 (M+1).

1-(SR)-(3,5-Bis(trifluoromethyl)phenyl)methoxy-2-(RS)-phenyl-3-(SR)-(methylamino)cyclopentane
Mass spec (NH$_3$/CI): 418 (M+1).

EXAMPLE 8

Methyl 3-(SR)-(1-(SR)-(3,5-bis(trifluoromethyl)phenyl)ethoxy)-2-(RS)-phenylcyclopentane-1-(RS)-carboxylate (higher R$_f$ α-methyl isomer) and methyl 3-(SR)-(1-(RS)-(3,5-bis(trifluoromethyl)phenyl)ethoxy)-2-(RS)-phenylcyclopentane-1-(RS)-carboxylate (lower R$_f$ α-methyl isomer) (Racemic 2,3-trans isomers)

Step A: (+/−)-1-3,5-Bis(trifluoromethyl)phenyl)-1-hydroxyethane

To a solution of 17.8 g of 3',5'-bis(trifluoromethyl)acetophenone in 300 mL of absolute ethanol was added 1.32 g of sodium borohydride while stirring in an ice bath. After 30 minutes the ice bath was removed and stirring was continued for an additional 1.5 hours. The reaction was quenched using excess 2 N hydrochloric acid and the solvent was mostly evaporated in vacuo. The residue was partitioned between ethyl acetate and aq. hydrochloric acid and the aqueous layer was extracted again with ethyl acetate. The separate organic layers were sequentially washed with brine, then combined, dried over magnesium sulfate and evaporated to provide 16.74 g of the title compound as a white solid after vacuum drying.

Step B: (+/−)-(1-(3,5-Bis(trifluoromethyl)phenyl)ethyl) trichloroacetamidate

To 40 mL of anhydrous ether was added 160 mg of 60% sodium hydride in mineral oil. After stirring 10 minutes, 10.3 g of the above racemic alcohol dissolved in 25 mL of ether was added. The reaction was warmed slightly and stirred until a homogeneous solution was obtained. After a further 10 minutes, the solution was added via canula to a solution of 4.0 mL of trichloroacetonitrile in 10 mL of ether cooled in an ice bath. After 1 hour an amber color was produced and the reaction was concentrated to give 15.6 g of the title product as an amber oil.

Step C: (+/−)-1-(3,5-Bis(trifluoromethyl)phenyl)ethyl bromide

To a solution of 1.89 g of (+/−)-1-(3,5-bis(trifluoromethyl)phenyl)-1-hydroxyethane prepared as in Example 8, Step A in 50 mL of acetonitrile at room temperature was added 5.15 g of triphenylphosphene-dibromide. After 1.5 hours, the reaction was partitioned between ether and water and the ether layer was washed with brine, dried with sodium sulfate and evaporated. The product was triturated with hexanes, filtered to remove the solid and reconcentrated. The residue was purified by flash chromatography using hexanes to provide 1.75 g of title compound as an oil.

Step D: Methyl 3-(SR)-(1-(SR)-(3,5-bis(trifluoromethyl)phenyl)ethoxy)-2-(RS)-phenylcyclopentane-1-(RS)-carboxylate (higher R$_f$ α-methyl isomer) and methyl 3-(SR)-(1-(RS)-(3,5-bis(trifluoromethyl)phenyl)ethoxy)-2-(RS)-phenylcyclopentane-1-(RS)-carboxylate (lower R$_f$ α-methyl isomer) (Racemic 2,3-trans isomers)

Method A

To a solution of 153 mg of the lower Rf$_f$ 2,3-trans alcohol isomer from Example 1, Step E, Method A in 2.0 mL of dry dichloromethane was added 600 mg of the trichloroacetamidate from Step B in 2.0 mL of cyclohexane. After stirring for 10 minutes, 0.015 mL of triflic acid was added. After 2 hours the reaction was filtered to remove any insoluble white solid. The filtrate was diluted with dichloromethane and washed with saturated sodium bicarbonate, water and brine, and then dried with sodium sulfate and concentrated. The crude solid was purified by flash chromatography using 2 to 5% ethyl acetate in hexanes to provide first 145 mg of the higher R$_f$ α-methyl isomer. NMR (CDCl$_3$): δ1.2 (d, 3H), 1.8–2.1 (m, 4H), 2.8 (m, 1H), 3.4 (dd, 1H), 3.58 (s, 3H), 3.78 (q, 1H), 4.3 (q, 1H), 7.16–7.3 (m, 5H), 7.43 (s,2H),7.7 (s, 1H).

Mass spec (NH$_3$/CI): 461 (M+1).

Further elution afforded 148 mg of the lower R$_f$ α-methyl isomer. NMR (CDCl3): δ1.34 (d, 3H), 1.86–1.92 (m, 1H), 2.05–2.1 (m, 3H), 2.80 (q, 1H), 3.34 (dd, 1H), 3.78 (q, 1H), 4.46 (q, 1H), 7.04–7.24 (m, 5H), 7.43 (s, 2H), 7.64 (s, 1H).

Mass spec (NH$_3$/CI): 461 (M+1).

Method B

To a solution of 219 mg of the lower R$_f$ 2,3-trans alcohol isomer from Example 1, Step E, Method A and 642 mg of above bromide from Step C in 3.0 mL of dry DMF at room temperature was added 80 mg of 60% sodium hydride in mineral oil in portions over 10 minutes. After 2 hours, additional bromide (321 mg) and sodium hydride (40 mg) were added and stirring was continued another 2 hours. The reaction was then quenched with dilute hydrochloric acid. The mixture was extracted twice with ether and the organic layers were washed with brine, combined, dried with sodium sulfate and evaporated. The residue was purified by flash chromatography eluting with hexanes and then 5% ethyl acetate in hexanes to give first the higher R$_f$ product isomer (50 mg) and then the lower product isomer (47 mg). The NMR of each was the same as in Method A.

EXAMPLE 9

Methyl 3-(SR)-(1-(SR)-(3,5-bis(trifluoromethyl)phenyl)ethoxy)-2-(SR)-phenylcyclopentane-1-(SR)-carboxylate (higher $R_f$ α-methyl isomer) and methyl 3-(SR)-(1-(RS)-(3,5-bis(trifluoromethyl)phenyl)ethoxy)-2-(SR)-phenylcyclopentane-1-(SR)-carboxylate (lower $R_f$ α-methyl isomer) (Racemic 2,3-cis isomers)

Following essentially the same procedure as in Example 8, Step D, Method A but employing methyl 3-(SR)-(hydroxy)-2-(SR)-phenylcyclopentane-1-(SR)-carboxylate (racemic 2,3-cis isomer from Example 1, Step E, Method A higher isomer or Method B) (1.06 g), the title compounds (378 and 712 mg) were obtained.

Higher $R_f$ isomer:
NMR (CDCl$_3$): δ1.04 (d, 3H), 1.75–1.89 (m, 2H), 1.95–2.04 (m, 1H), 1.95–2.04 (m, 1H), 3.34 (m, 2H), 3.6 (s, 3H), 3.87–3.96 (m, 2H), 7.05 (m, 2H), 7.34 (m, 2H), 7.6 (s, 2H), 7.75 (s, 1H).

Lower $R_f$ isomer:
NMR (CDCl$_3$): δ1.3 (d, 3H), 1.92–2.04 (m, 3H), 2.28–2.37 (m, 1H), 3.24 (dd, 1H), 3.36–3.44 (m, 1H), 3.58 (s, 3H), 3.72 (m, 1H), 4.4 (q, 1H), 6.94 (m, 2H) 7.18–7.22 (m, 4H), 7.63 (s, 1H).

EXAMPLE 10

1-(R)-(1-(S)-(3,5-Bis(trifluoromethyl)phenyl)ethoxy-2-(R)-phenyl-3-(S)-((1-(S)-phenyl)ethoxycarbonylamino)cyclopentane (higher $R_f$ α-methyl isomer) and 1-(S)-(1-(R)-(3,5-bis(trifluoromethyl)phenyl)ethoxy-2-(S)-phenyl-3-(R)-((1-(S)-phenyl)ethoxycarbonylamino)cyclopentane (lower $R_f$ α-methyl isomer) (non-racemic 2,3-trans)

The title compounds were prepared essentially the same as in Examples 3 and 4 except that (S)-α-methylbenzyl alcohol was reacted with the intermediate isocyanate and the diastereomers were chromatographically separated.

Step A: 3-(SR)-(1-(RS)-(3,5-Bis(trifluoromethyl)phenyl)-ethoxy)-2-(RS)-phenylcyclopentane-1-(RS)-carboxylic acid (from lower $R_f$ α-methyl isomer) (Racemic 2,3-trans isomers)

To a solution of 905 mg of methyl 3-(SR)-(1-(RS)-(3,5-bis(trifluoromethyl)phenyl)-ethoxy)-2-(RS)-phenylcyclopentane-1-(RS)-carboxylate (lower $R_f$ α-methyl isomer) (Racemic 2,3-trans isomer) from Example 8, Step D, Method A in 20 mL of methanol was added 5 mL of 2.0 N sodium hydroxide. After heating at reflux for 2 hours, the methanol was evaporated, and the residual liquid was acidified with 2 N hydrochloric acid. The aqueous phase was washed twice with ethyl acetate. The separate organic layers were washed with brine, combined, dried with sodium sulfate and evaporated to furnish 943 mg of the carboxylic acid.

Step B: 3-(SR)-(1-(RS)-(3,5-Bis(trifluoromethyl)phenyl)-ethoxy)-2-(RS)-phenylcyclopentane-1-(RS)-carboxylic acid chloride (from lower $R_f$ α-methyl isomer) (Racemic 2,3-trans isomers)

A solution of 855 mg 3-(SR)-(1-(RS)-(3,5-bis(trifluoromethyl)phenyl)-ethoxy)-2-(RS)-phenylcyclopentane-1-(RS)-carboxylic acid in 20 mL of dry dichloromethane was treated with 2 drops of DMF followed by 0.36 mL of oxalyl chloride. After 1 hour the reaction was evaporated and the residual yellow oil was concentrated twice more from dichloromethane.

Step C: 3-(SR)-(1-(RS)-(3,5-Bis(trifluoromethyl)phenyl)-ethoxy)-2-(RS)-phenylcyclopentane-1-(RS)-carbonyl azide (from lower $R_f$ α-methyl isomer) (Racemic 2,3-trans isomers)

The above acid chloride was then taken up in 20 mL of acetone and added to a solution of 248 mg of sodium azide in 20 mL of water stirring in an ice bath. After 30 minutes the reaction was partitioned between benzene and cold water. The aqueous layer was washed again with benzene and the separate organic layers were washed with brine, combined, dried with sodium sulfate and then evaporated to approximately 10 mL (DO NOT EVAPORATE TO DRYNESS!!!).

Step D: 3-(SR)-(1-(RS)-(3,5-Bis(trifluoromethyl)phenyl)-ethoxy)-2-(RS)-phenylcyclopentane-1-(RS)-isocyanate (from lower $R_f$ α-methyl isomer) (Racemic 2,3-trans isomers)

Another 40 mL of dry benzene was added to the above solution of acyl azide and the solution was heated at 80° C. for 2 hours and then evaporated to give crude isocyanate as an oil.

Step E: 1-(R)-(1-(S)-(3,5-Bis(trifluoromethyl)phenyl)ethoxy-2-(R)-phenyl-3-(S)-((1-(S)-phenyl)ethoxycarbonylamino) cyclopentane (higher $R_f$ α-methyl isomer) and 1-(S)-(1-(R)-(3,5-bis(trifluoromethyl)phenyl)-ethoxy-2-(S)-phenyl-3-(R)-((1-(S)-phenyl)ethoxycarbonylamino)-cyclopentane (lower $R_f$ α-methyl isomer) (non-racemic 2,3-trans)

The above isocyanate was dissolved in 8 mL of toluene and treated with 1 g of (S)-(−)-α-methylbenzyl alcohol, 0.66 mL of DIPEA and 15 mg of dimethylaminopyridine. The resulting solution was heated at 100° C. overnight and then evaporated. Purification on a silica gel flash column (5 to 20% ethyl acetate in hexanes) gave 193 mg of pure higher Rf isomer and 180 mg of pure lower $R_f$ isomer.

Higher $R_f$ isomer.
NMR (CDCl$_3$): δ1.37 (d, 6H), 1.68–2.3 (m, 4H), 2.85 (m, 1H), 3.74 (q, 1H), 4.02 (q, 1H), 4.48 (q, 1H), 4.76 (br s, 1H), 5.67 (q, 1H), 7.06–7.4 (m, 10H), 7.46 (s, 2H), 7.67 (s, 1H).

Lower $R_f$ isomer.
NMR (CDCl$_3$): δ1.37 (d, 3H), 1.47 (m, 3H), 1.7–1.94 (m, 2H), 2.02–2.12 (m, 1H), 2.24–2.36 (m, 1H), 2.84 (m, 1H), 3.74 (m, 1H), 4.0 (q, 1H), 4.49 (q, 1H) 4.77 (br s, 1H), 5.67 (m, 1H), 7.02 (br s, 2H), 7.16–7.32 (m, 8H), 7.46 (s, 2H) 7.67 (s, 1H).

EXAMPLE 11

1-(R)-(1-(S)-(3,5-(trifluoromethyl)phenyl)ethoxy)-2-(R)-phenyl-3-(S)-aminocyclopentane To 185 mg of the higher $R_f$ isomer from Example 10, Step E dissolved in 5 mL of ethanol was added 40 mg of 10% Pd on carbon and the mixture was hydrogenated on the Parr shaker. The reaction was filtered over Celite and the filtrate was evaporated to provide 111 mg of the title compound as a white solid. Mass spec (NH$_3$/CI): 418 (M+1).

EXAMPLE 12

1-(S)-(1-(R)-(3,5-Bis(trifluoromethyl)phenyl)ethoxy)-2-(S)-phenyl-3-(R)-aminocyclopentane To 174 mg of the lower $R_f$ isomer from Example 10, Step E dissolved in 5 mL of ethanol was added 40 mg of 10% Pd on carbon and the mixture was hydrogenated on the Parr shaker. The reaction was filtered thru Celite and the filtrate was evaporated to provide 106 mg of the title compound as a white solid.

Mass spec (NH$_3$/CI): 418 (M+1).

EXAMPLE 13

1-(S)-(1-(S)-(3,5-Bis(trifluoromethyl)phenyl) ethoxy)-2-(R)-(4-fluorophenyl)-3-(R)- (methoxycarbonyl)cyclopentane (higher $R_f$ α-methyl isomer) and 1-(S)-(1-(R)-(3,5-bis (trifluoromethyl)phenyl)ethoxy)-2-(R)-(4-fluorophenyl)-3-(R)-(methoxycarbonyl)cyclopentane (lower $R_f$ α-methyl isomer) (non-racemic 2,3-trans isomers Step A–C: Methyl trans-(+/−)-2-(4-fluorophenyl) cyclopentan-3-one-1-carboxylate Using essentially the same procedures as described in Example 1, Steps A–C but starting with 4-fluorobenzaldehyde, the title compound was prepared. NMR (CD$_3$OD): δ2.0–2.2 (m, 1H), 2.3–2.5 (m, 2H), 2.56–2.76 (m, 1H), 3.1–3.3 (m, 1H), 3.68 (s, 3H), 3.72 (br d, 1H), 6.98–7.16 (m, 4H).

Step D: Methyl 3-(SR)-(hydroxy)-2-(SR)-(4-fluorophenyl) cyclopentane-1-(SR)-carboxylate (Racemic 2,3-cis isomer) and methyl 3-(SR)-(hydroxy)-2-(RS)-(4-fluorophenyl)cyclopentane-1-(RS)-carboxylate (Racemic 2,3-trans isomer)

Method A

Using essentially the same procedures as described in Example 1, Step D but using with the 4-fluorophenyl derivative from Step C, the title compounds were prepared. Higher $R_f$ 2,3-cis isomer. NMR (CDCl$_3$): δ1.86–2.0 (m, 2H), 2.1–2.2 (m, 1H), 2.29–2.36 (m, 1H), 3.28–3.4 (m, 2H), 3.6 (s, 3H), 4.28 (m, 1H), 7.0 (m, 2H) 7.24 (m, 2H). Lower $R_f$ 2,3-trans isomer. NMR (CDCl$_3$): δ1.80–1.86 (m, 1H), 2.06–2.17 (m, 3H), 2.87 (q, 1H), 3.19 (dd, 1H), 3.6 (s, 3H), 4.14 (q, 1H), 6.99 (m, 2H) 7.18 (m, 2H).

Method B

Additional quantities of the title 2,3-trans alcohol can also be obtained from the minor 2,3-cis alcohol obtained above thru oxidation to the ketone as described in Example 14, Step A, Alternate Method and subsequent reduction with sodium borohydride as in Method A above. Thus, 4.35 g of 2,3-cis alcohol was converted to 2.35 g of pure 2,3-trans product.

Method C

Step D–C1: 2-(4-Fluorophenyl)cyclopent-2-en-1-one

To a solution of 80 g (0.5 mole) of 2-bromocyclopent-2-en-1-one in 1600 mL of toluene was added 23.3 g (0.1 mole) of triphenylphosphine and 5.63 g (0.025 mole) of palladium (II) acetate at room temperature. A solution of 84 g (0.6 mole) of 4-fluorophenylboronic acid in 800 mL of ethanol was added followed immediately by the addition of 800 mL of sat'd sodium bicarbonate. The reaction was heated to reflux for 4 hours and was then cooled and poured into brine. The mixture was extracted twice with ethyl acetate and the organic layers were each washed with a portion of brine, dried over sodium sulfate, combined and concentrated. The residue was purified by flash chromatography (25 to 50% methylene chloride in hexanes) to afford 67 g of title compound.

Step D–C2: (+/−)-trans-3-Cyano-2-(4-fluorophenyl) cyclopentan-1-one

To a solution of 61 g (0.35 mole) of 2-(4-fluorophenyl) cyclopent-2-en-1-one from Step D–C1 in 600 mL of methanol at 0° C. was added a solution of 65 g (0.49 mole) of potassium cyanide in 250 mL of water over 30 minutes. The reaction was stirred at 0° C. for 5 hours and then at room temperature for 30 minutes. Most of the methanol was removed in vacuo and the mixture was then diluted with water and extracted twice with ethyl acetate. The organic layers were each washed with a portion of brine, dried over sodium sulfate, combined and concentrated. The residue was purified by flash chromatography (30% ethyl acetate in hexanes) to afford 50 g of title compound.

Step D–C3: (+/−)-1,2-trans-2,3-trans-3-Cyano-2-(4-fluorophenyl)-1-hydroxycyclopentane To a solution of 50 g (0.25 mole) of 3-cyano-2-(4-fluorophenyl)cyclopentan-1-one from Step D–C2 in 850 mL of methanol: THF (2.5:1) at −78° C. was added 14 g (0.37 mole) of sodium borohydride portionwise over 20 minutes. After stirring at −78° C. for 1.5 hours, the reaction was warmed to room temperature for 30 minutes and was then quenched by addition of acetone. The reaction was concentrated and the mixture was then diluted with water and extracted four times with ethyl acetate. The organic layers were each washed with a portion of brine, dried over sodium sulfate, combined and concentrated. The residue was purified by flash chromatography (0 to 7% ethyl acetate in methylene chloride) to afford 35 g of title compound as the major, lowest $R_f$ isomer.

Step D–C4: Methyl 3-(SR)-(hydroxy)-2-(RS)-(4-fluorophenyl)cyclopentane-1-(RS)-carboxylate(Racemic 2,3-trans isomer)

To a solution of 35 g (0.17 mole) of (+/−)-1,2-trans-2,3-trans-3-cyano-2-(4-fluorophenyl)-1-hydroxycyclopentane from Step D–C3 in 300 mL of methanol at room temperature was added 150 mL of 5N sodium hydroxide. The reaction was heated to reflux for 20 hours and was then cooled and concentrated in vacuo to remove most of the methanol. The mixture was diluted with water, the pH was adjusted to 2-3 with concentrated hydrochloric acid and the mixture was extracted three times with ethyl acetate. The organic layers were each washed with a portion of brine, dried over sodium sulfate, combined and concentrated to afford 35.2 g of 3-(SR)-(hydroxy)-2-(RS)-(4-fluorophenyl)cyclopentane-1-(RS)-carboxylic acid. The crude acid was then taken up in 300 mL of methanol and the solution was saturated with hydrogen chloride gas. After stirring at room temperature for 20 hours, the mixture was concentrated and then diluted with water and extracted twice with ethyl acetate. The organic layers were each washed with sat'd sodium bicarbonate and brine, dried over sodium sulfate, combined and concentrated. The residue was purified by flash chromatography (20% ethyl acetate in hexanes to afford the title compound which was the same as the lower product from Method A.

Step E: Resolution of methyl 3-(S)-(hydroxy)-2-(R)-(4-fluorophenyl)cyclopentane-1-(R)-carboxylate (from R-salt) and methyl 3-(R)-(hydroxy)-2-(S)-(4-fluorophenyl)cyclopentane-1-(S)-carboxylate (from S-salt). (Non-racemic 2,3-trans isomers)

Step E-1: (R)-(+)-α-Methylbenzylammonium 3-(S)-(hydroxy)-2-(R)-(4-fluorophenyl)cyclopentane-1-(R)-carboxylate To a solution of 3.0 g of the lower $R_f$ trans alcohol of Example 13, Step D in 20 mL of methanol was added 13 mL of 5N sodium hydroxide. The reaction was stirred at room temperature for 20 hours and then concentrated in vacuo. The residue was taken up in water, acidified with 2N hydrochloric acid, and extracted with three portions of ethyl acetate. The organic layers were washed with a portion of brine, combined, dried over sodium sulfate and evaporated to afford the crude acid as a white solid. To a warm solution of 2.3 g of the above crude acid in 35 mL of isopropanol was added 930 mg (0.75 eq) of (R)-(+)-α-methylbenzyl amine. The solution was seeded and aged at room temperature for 4 hours, the solid was filtered, washed with isopropanol and then ether, and air dried to give 1.8 g white solid. Recrystallization twice from 30 mL of isopropanol afforded 1.1 g of the title compound as a white solid. $[\alpha]_D$ (EtOH)=−11.3 (c=0.37).

Step E-2: (S)-(−)-α-Methylbenzylammonium 3-(R)-(hydroxy)-2-(S)-(4-fluorophenyl)cyclopentane-1-(S)-carboxylate The mother liquors from Step E-1 were combined and concentrated. The residue was taken up in water and acidified with 2N hydrochloric acid and was extracted with 3 portions of ethyl acetate. The organic layers were washed with a portion of brine, combined, dried sodium sulfate and evaporated. The residue was dissolved in 25 mL of isopropanol and 0.75 g (0.95 eq) of (S)-(−)-α-methylbenzyl amine was added. The solution was seeded and left at room temperature overnight afterwhich the solid was filtered, washed with isopropanol and then ether, and air dried to give 1.56 g white solid. Recrystallization from another 30 mL of isopropanol afforded 1.3 g of the title compound as a white solid. $[\alpha]_D$ (EtOH)=+12.5 (c=0.44).

Step E-3: 3-(S)-(Hydroxy)-2-(R)-(4-fluorophenyl)cyclopentane-1-(R)-carboxylic acid The salt from Step E-1 was dissolved in water and acidified with 2N hydrochloric acid and was extracted with 3 portions of ethyl acetate. The organic layers were washed with a portion of brine, combined, dried over sodium sulfate and evaporated to give a white solid. $[\alpha]_D$ (EtOH)=−19.9 (c=0.675).

Step E-4: 3-(R)-(Hydroxy)-2-(S)-(4-fluorophenyl)cyclopentane-1-(S)-carboxylic acid The salt from Step E-2 was dissolved in water and acidified with 2N hydrochloric acid and was extracted with 3 portions of ethyl acetate. The organic layers were washed with a portion of brine, combined, dried over sodium sulfate and evaporated to give a white solid. $[\alpha]_D$ (EtOH)=+21.6 (c=2.55).

Step E-5: Methyl 3-(S)-(hydroxy)-2-(R)-(4-fluorophenyl)cyclopentane-1-(R)-carboxylate
Method A The salt from Step E-1 was converted to the free acid as in Step E-3 and dissolved in ether and a solution of diazomethane was added portionwise until the yellow color persisted. The excess diazomethane was quenched with acetic acid and the volatiles were removed in vacuo. The residue was purified by flash chromatography eluting with 20 to 40% ethyl acetate in hexanes to obtain 800 mg of title compound as an oil. $[\alpha]_D$ (EtOH)=−30 (c=0.390).
Method B (R)-salt (8.7 g) obtained as in Step E-1 was converted to the free acid as in Step E-3 to give 5.7 g of crude acid. $[\alpha]_D$ (EtOH)=−19.9 (c=0.675). This was taken up in 200 mL of methanol and saturated with hydrogen chloride gas. The solution was stirred at room temperature for 16 hours and then concentrated in vacuo. The residue was dissolved in water and extracted twice with ether. The organic layers were washed with a portion of brine, combined, dried over sodium sulfate and evaporated to give 6.0 g of oil. $[\alpha]^D$ (EtOH)=−30.5 (c=0.98).

Step E-6: Methyl 3-(R)-(hydroxy)-2-(S)-(4-fluorophenyl)cyclo-pentane-1-(S)-carboxylate Using essentially the same procedures as in Step E-5, the acid from the (S)-salt (7.50 g) afforded 4.92 g of the title compound as an oil. $[\alpha]_D$ (EtOH)=+37 (=1.05).

Step F: 1-(S)-(1-(S)-(3,5-Bis (trifluoromethyl)phenyl) ethoxy)-2-(R)-(4-fluorophenyl)-3-(R)-(methoxycarbonyl)cyclopentane (higher $R_f$ α-methyl isomer) and 1-(S)-(1-(R)-(3,5-bis(trifluoromethyl)phenyl)-ethoxy)-2-(R)-(4-fluorophenyl)-3-(R)-(methoxycarbonyl)cyclopentane (lower $R_f$ α-methyl isomer)(non-racemic 2,3-trans isomers)

Following essentially the same procedure as in Example 8, Step D, Method A but using non-racemic alcohol from Step E-5, the title compounds were prepared. The NMR spectra were identical to those of the racemic products.

EXAMPLE 14

1-(S)-(1-(S)-(3,5-Bis(trifluoromethyl)phenyl) ethoxy)-2-(S)-(4-fluorophenyl)-3-(S)-(methoxycarbonyl) cyclopentane(higher $R_f$ α-methyl isomer) and 1-(S)-(1-(R)-(3,5-bis (trifluoromethyl)phenyl)ethoxy)-2-(S)-(4-fluorophenyl)-3-(S)-(methoxycarbonyl)cyclopentane (lower $R_f$ α-methyl isomer) (non-racemic 2,3-cis isomers)

Step A: Methyl 3-(S)-(hydroxy)-2-(S)-(4-fluorophenyl)cyclopentane-1-(S)-carboxylate (from R-salt) and methyl 3-(R)-(hydroxy)-2-(R)-(4-fluorophenyl)cyclopentane-1-(R)-carboxylate (from S-salt). (Non-racemic 2,3-cis isomers)
Method A Using essentially the same procedures as in Example 13, Step E the title compounds were prepared from the higher $R_f$ 2,3-cis alcohol from Example 13, Step D.

Step A-1: (R)-(+/−)-α-Methylbenzylammonium 3-(S)-(hydroxy)-2-(S)-(4-fluorophenyl)cyclopentane-1-(S)-carboxylate
$[\alpha]_D$ (EtOH)=+84 (c=0.375).

Step A-2: (S)-(−)-α-Methylbenzylammonium 3-(R)-(hydroxy)-2-(R)-(4-fluorophenyl)cyclopentane-1-(R)-carboxylate
$[\alpha]_D$ (EtOH)=−81 (c=0.335).

Step A-3: 3-(S)-(Hydroxy)-2-(S)-(4-fluorophenyl)cyclopentane-1-(S)-carboxylic acid
From Step A-1. $[\alpha]_D$ (EtOH)=+126 (c=0.915).

Step A-4: 3-(R)-(Hydroxy)-2-(R)-(4-fluorophenyl)cyclopentane-1-(R)-carboxylic acid
From Step A-2. $[\alpha]_D$ (EtOH)=−108 (c=0.810).

Step A-5: Methyl 3-(S)-(hydroxy)-2-(S)-(4-fluorophenyl)cyclopentane-1-(S)-carboxylate
From Step A-3. $[\alpha]_D$ (EtOH)=+133 (c=1.81).

Alternate Step A: Methyl 3-(S)-(hydroxy)-2-(S)-(4-fluorophenyl)cyclopentane-1-(S)-carboxylate Step A'-A,: Methyl 2-(S)-(4-fluorophenyl)cyclopentan-3-one-1-(S)-carboxylate Method A To a solution of 3.35 g of non-racemic alcohol obtained as in Example 13, Step E-6 was added dropwise 5.8 mL of 8N Jones reagent over 1 minute. After stirring at room temperature for 30 minutes, the reaction was concentrated in vacuo. The residue was diluted with water and extracted twice with ether. The organic layers were washed with a portion of brine, combined, dried over sodium sulfate and evaporated to give 3.55 g of oil. Flash chromatography with 20 to 40% ethyl acetate in hexanes afforded 2.63 g of title compound as a white solid. $[\alpha]_D$ (EtOH)=+25(c=0.62).
Method B A solution of 20.25 mL of oxalyl chloride in 200 mL of methylene chloride was cooled to <−70° C. in a dry ice/acetone bath. A solution of 32 mL of DMSO in 50 mL of methylene chloride was added dropwise while maintaining the temperature at <−60° C. After a further 15 minutes of stirring, a solution of 21.75 g of non-racemic alcohol obtained as in Example 13, Step E-6 in 100 mL of methylene chloride was added dropwise while maintaining the temperature at <−60 ° C. After a further 60 minutes of stirring, a solution of 127 mL of DIPEA in 100 mL of methylene chloride was added dropwise while maintaining the temperature at <−60 ° C. The ice bath was then removed and the reaction was allowed to warm to 0°C. over 1 hour. The reaction was then slowly added (some gas evolution) to a mixture of 500 mL of ice water and 250 mL of 2 N hydrochloric acid. The layers were separated and the aqueous layer was extracted with a second portion of methylene chloride. The organic layers were each washed with brine, dried over sodium sulfate, combined and evaporated. The residue was purified by flash chromatography using a gradient of 20 to 30% ethyl acetate/hexanes as eluent. Evaporation of the product fractions afforded 21.7 g of title product as a white solid. $[\alpha]_D$ (EtOH)=+27(c=0.84).

Step A'–B: Methyl 3-(S)-(hydroxy)-2-(S)-(4-fluorophenyl)cyclopentane-1-(S)-carboxylate A solution of 0.55 g of crude ketone prepared as in Step A'–A in 30 mL of THF was cooled in an ice bath and 3.2 mL of 1M L-Selectride was added. The ice bath was removed and the reaction was stirred at room temperature for 2 hours before being quenched with 2N hydrochloric acid. The mixture was extracted twice with ethyl acetate and the organic layers were washed with a portion of brine, combined, dried over sodium sulfate and evaporated. TLC analysis (30% ethyl acetate in hexanes) indicated that very little if any 2,3-trans alcohol was formed. The residue was purified by flash chromatography eluting with 10 to 20% ethyl acetate in hexanes to obtain 210 mg of title compound as an oil. $[\alpha]_D$ (EtOH)=+107(c=0.79).

Step B: 1-(S)-(1-(S)-(3,5-Bis(trifluoromethyl)phenyl)ethoxy)-2-(S)-(4-fluorophenyl)-3-(S)-(methoxycarbonyl)cyclopentane (higher $R_f$α-methyl isomer) and 1-(S)-(1-(R)-(3,5-bis(trifluoromethyl)phenyl)-ethoxy)-2-(S)-(4-fluorophenyl)-3-(S)-(methoxycarbonyl)cyclopentane (lower $R_f$α-methyl isomer)(non-racemic 2,3-cis isomers)

Following essentially the same procedure as in Example 8, Step D, Method A but using non-racemic alcohol from Step A-5, the title compounds were prepared. The NMR spectra were identical to those of the racemic products.

EXAMPLE 15

Following essentially the same procedures as in Examples 3 thru 6, but using non-racemic ether from Example 13, Step F (lower $R_f$α-methyl isomer), the following 1,2-trans compounds were prepared.

1-(S)-(1-(R)-(3,5-Bis(trifluoromethyl)phenyl)ethoxy)-2-(S)-(4-fluorophenyl)-3-(R)-aminocyclopentane 1-(S)-(1-(R)-(3,5-Bis(trifluoromethyl)phenyl)ethoxy)-2-(S)-(4-fluorophenyl)-3-(R)-(methylamino)cyclopentane

EXAMPLE 16

1-(S)-(1-(R)-(3,5-Bis(trifluoromethyl)phenyl)ethoxy)-2-(R)-(4-fluorophenyl)-3-(S)-(methylamino)cyclopentane Following essentially the same procedures as in Examples 3 thru 6, but using non-racemic ether from Example 14 (lower $R_f$α-methyl isomer), the title 1,2-cis compound was prepared.

EXAMPLE 17

1-(S)-(1-(R)-(3,5-Bis(trifluoromethyl)phenyl)ethoxy)-2-(R)-(4-fluorophenyl)-3-(R)-aminomethylcyclopentane Step A: 1-(S)-(1-(R)-(3,5-Bis(trifluoromethyl)phenyl)ethoxy)-2-(R)-(4-fluorophenyl)-3-(R)-carboxylcyclopentane Following essentially the same procedure as in Example 3, but using non-racemic ether/ester from Example 13, Step F (lower $R_f$α-methyl isomer) (1.0 gm), the title compound (0.9 gm) was prepared as an oil.

Step B: 1-(S)-(1-(R)-(3,5-Bis(trifluoromethyl)phenyl)ethoxy)-2-(R)-(4-fluorophenyl)-3-(R)-aminocarbonylcyclopentane To a solution of 0.9 gm of the acid from Step A in 15 mL of methylene chloride was added a drop of DMF and then 0.285 mL of oxalyl chloride. The reaction was stirred at room temperature for 1 hour and then evaporated to dryness. The residue was taken up in 15 mL of 1:1 methylene chloride: THF and 1.4 mL of 7.4M ammonium hydroxide was added. The reaction was stirred at room temperature for 1 hour and was then diluted with water and extracted twice with ethyl acetate. The organic layers were washed with brine, dried over sodium sulfate, combined and evaporated. The residue was purified by FC (50% ethyl acetate/hexanes) to give 850 mg of title compound as a white solid. Mass spec (ESI): 464(M+1).

Step C: 1-(S)-(1-(R)-(3,5-Bis(trifluoromethyl)phenyl)ethoxy)-2-(R)-(4-fluorophenyl)-3-(R)-aminomethylcyclopentane To a solution of 0.70 gm of the amide from Step B in 10 mL of THF was added 2.25 mL of 2M borane-dimethylsulfide in THF. The reaction was stirred at room temperature for 16 hours and then warmed at 50° C. for another 6 hours. The excess borane was quenched with dropwise addition of methanol and then 20 mL of methanol and 5 mL of 2N hydrochloric acid were added and the reaction was stirred at room temperature for 24 hours. The mixture was concentrated in vacuo, diluted with water, made basic with 2N sodium hydroxide and extracted twice with methylene chloride. The organic layers were washed with brine, dried over sodium sulfate, combined and evaporated. The residue was purified by FC (methylene chloride, the 5 −10% methanol in methylene chloride) to give 350 mg of title compound. NMR (CDCl$_3$) δ1.33 (d, 3H, J=6.5 Hz), 1.53 (br s, NH$_2$+H$_2$O), 1.5–1.65 (m, 1H), 1.7–1.85 (m, 1H), 1.85–2.0 (m, 2H), 2.0–2.15 (m, 1H), 2.59 (dd, 1H, J=8 and 10 Hz 2.52 and 2.67 (dABq, 2H, J=4.6 and 12.6 Hz), 3.67 (q, 1H, J=6 Hz), 4.45 (q, 1H, J=6.5 Hz), 6.85–6.95 (m, 2H), 6.95–7.05 (m, 2H), 7.38 (s, 2H), 7.64 (s, 1H). Mass spec (ESI): 450(M+1).

EXAMPLE 18

1-(S)-(1-(R)-(3,5-Bis(trifluoromethyl)phenyl)ethoxy)-2-(R)-(4-fluorophenyl)-3-(R)-((methylamino)methyl)cyclopentane Following essentially the same procedures as in Example 17, but using 2M methylamine in THF in place of ammonium hydroxide in Step B, the title compound was prepared. Mass spec (NH$_3$/CI): 464(M+1).

EXAMPLE 19

1-(S)-(1-(R)-(3,5-Bis(trifluoromethyl)phenyl)ethoxy)-2-(R)-(4-fluorophenyl)-3-(R)-(hydroxymethyl)cyclopentane (non-racemic 1,2-trans)

Method A

To a solution of 2.0 g of non-racemic ether/ester from Example 13, Step F (lower $R_f$α-methyl isomer) in 50 mL of THF cooled to 0° C. in an ice bath was added 80 mg of LAH. After 15 minutes the ice bath was removed and the reaction was stirred for another 30 minutes. At this time the reaction was not complete by TLC and an additional 60 mg of LAH was added and stirring was continued for another 1 hour. The reaction was quenched with the addition of ethyl acetate, poured into water containing 10 mL of 2N hydrochloric acid and extracted twice with ether. The organic layers were washed with a portion of brine, combined, dried over sodium sulfate and evaporated to give 1.92 g of title compound as an oil. NMR (CDCl$_3$) δ1.34 (d, 3H, J=6.5 Hz), 1.7–1.85 (m, 2H), 1.85–2.0 (m, 1H), 2.0–2.15 (m, 2H), 2.72 (dd, 1H, J=8 and 11 Hz), 3.52 (dABq, 2H, J=6.6 and 10.6 Hz), 3.68 (q, 1H, J=6 Hz), 4.47 (q, 1H, J=6.5 Hz), 6.85–6.95 (m, 2H), 6.95–7.05 (m, 2H), 7.40 (s,2H), 7.65 (s, 1H). Mass spec (NH$_3$/CI): 451(M+1).

Method B

To a solution of 6.25 g of non-racemic ether/ester from Example 13, Step F (lower R$_f$ α-methyl isomer) in 100 mL of THF cooled to 0° C. in an ice bath was added 13 mL of 2M lithium borohydride. After 15 minutes the ice bath was removed and the reaction was stirred at room temperature for 16 hours. At this time the reaction was not complete by TLC so the reaction was warmed to 50° C. and stirring was continued for another 5 hours. The reaction was cooled in an ice bath and quenched with the dropwise addition of water containing 2N hydrochloric acid and extracted twice with ether. The organic layers were washed with a portion of brine, combined, dried over sodium sulfate and evaporated to. give 1.92 g of title compound as an oil. Mass spec (NH$_3$/CI): 451(M+1).

EXAMPLE 20

1-(S)-(1-(R)-(3,5-Bis(trifluoromethyl)phenyl) ethoxy)-2-(R)-(4-fluorophenyl)-3-(R)-(((R and/or S)-3-carboxylpyrrolidin-1-yl)methyl)cyclopentane Step A: 1-(S)-(1-(R)-(3,5-Bis(trifluoromethyl)phenyl) ethoxy)-2-(R)-(4-fluorophenyl)-3-(R)-(bromomethyl) cyclopentane Method A To a solution of 1.9 g of alcohol from Example 19, Method A or B in 50 mL of dry acetonitrile at room temperature was added 2.0 g of triphenylphosphene-dibromide. After 1 hour an additional 700 mg of triphenylphosphene-dibromide was added and the reaction was stirred a further 1 hour. The reaction was quenched with sodium bicarbonate solution and extracted twice with ether. The organic layers were washed with a portion of brine, combined, dried over sodium sulfate and evaporated. The residue was purified by flash chromatography eluting with 10% ethyl acetate in hexanes to obtain 708 mg of title compound and 484 mg of recovered starting material. NMR (CDCl$_3$)δ1.34 (d, 3H, J=6.5 Hz), 1.7–1.85 (m, 2H), 1.85–2.05 (m, 1H), 2.05–2.2 (m, 2H), 2.78 (dd, 1H, J=8.3 and 10.9 Hz), 3.29 (dABq, 2H, J=7.1 and 10.1 Hz), 3.75 (m, 1H), 4.46 (q, 1H, J=6.5 Hz), 6.85–6.95 (m, 2H), 6.95–7.05 (m, 2H), 7.38 (s, 2H), 7.65 (s, 1 H). Mass spec (NH$_3$/CI): 513 (M+1), 433 (M+1- HBr).

Method B

To a solution of 520 mg of alcohol from Example 19, Method A or B in 20 mL of dry methylene chloride at room temperature was added 452 mg of triphenylphosphene and then 574 mg of carbon tetrabromide and stirred for 1–2 hours. The reaction was diluted with hexanes and filtered through Celite. The filtrate was concentrated and the residue was purified by flash chromatography eluting with 10% ethyl acetate in hexanes to obtain 519 mg of title compound as a waxy white solid. Mass spec (NH$_3$/CI): 513 (M+1), 433 (M+1- HBr).

Step B: 1-(S)-(1-(R)-(3,5-Bis(trifluoromethyl)phenyl) ethoxy)-2-(R)-(4-fluorophenyl)-3-(R)-(((R and/or S)-3-t-butoxycarboxylpyrrolidin-1-yl)methyl)cyclopentane To a solution of 300 mg of bromide from Example 20, Step A in 5 mL of acetonitrile was added 200 mg of (R,S)-3-t-butoxycarbonylpyrrolidine and 0.35 mL of DIPEA. The reaction was heated at 90° C. for 24 hours. The volatiles were removed under a stream of nitrogen and the residue was taken up in methylene chloride and washed with sat'd sodium bicarbonate solution and brine, dried over sodium sulfate and evaporated. The residue was purified by FC (25% ethyl acetate/hexanes) to give 252 mg of the diastereomeric mixture. More careful chromatography (10 then 25% ethyl acetate/hexanes) of 160 mg allowed for the separation of pure fractions of the higher (16.5 mg) and lower (15 mg) Rf pyrrolidine diastereomeric title compounds. Mass spec (ESI): 604 (M+1). Higher: NMR (CDCl$_3$) δ1.33 (d, 3H, J=6.5 Hz), 1.38 (s, 9H), 1.55–1.7 (m, 2H), 1.7–1.85 (m, 1H), 1.85–2.15 (2 m, 5 H), 2.2–2.35 (m, 2H), 2.35–2.45 (m, 1H), 2.45–2.55 (m, 2H), 2.58 (dd, 1H, J=8.3 and 10.9 Hz), 2.7–2.9 (m, 1H), 3.65 (q, 1H, J=8 Hz), 4.45 (q, 1H, J=6.5 Hz), 6.85–6.95 (m, 2H), 6.95–7.05 (m, 2H), 7.38 (s, 2H), 7.64 (s, 1H). Lower: NMR (CDCl$_3$) δ1.32 (d, 3H, J=6.5 Hz), 1.39 (s, 9H), 1.55–1.7 (m, 2H), 1.7–1.85 (m, 1H), 1.85–2.15 (2 m, 5H), 2.2–2.45 (m, 3H), 2.45–2.6 (m, 1H), 2.57 (dd, 1H, J=8.3 and 10.9 Hz), 2.7–2.9 (m, 1H), 3.65 (q, 1H, J=8 Hz), 4.45 (q, 1H, J=6.5 Hz), 6.85–6.95 (m, 2H), 6.95–7.05 (m, 2H), 7.38 (s, 2H), 7.63 (s, 1H).

Step C: 1-(S)-(1-(R)-(3,5-Bis(trifluoromethyl)phenyl) ethoxy)-2-(R)-(4-fluorophenyl)-3-(R)-(((R or S)-3-carboxylpyrrolidin-1-yl)methyl)cyclopentane To 16.5 mg of the higher R$_f$ diastereomer from Step B was added 0.5 mL of TFA. After 1.5 hours, the volatiles were removed in vacuo and the residue taken up in ethyl acetate and washed with sat'd sodium bicarbonate and brine. The aqueous layers were reextracted with another portion of ethyl acetate. The organic layers were dried, combined and evaporated. The residue was purified by prep TLC (83:15:1:1 methylene chloride: methanol: ammonium hydroxide:water) to afford 5.9 mg of title compound derived from the higher diastereomeric t-butyl ester. NMR (CDCl$_3$) δ1.31 (d, 3H, J=6.5 Hz), 1.6–1.75 (m, 1H), 1.75–1.9 (m, 1H), 2.0–2.15 (m, 2H), 2.2–2.35 (m, 3H), 2.45–2.75 (m, 4H), 2.75–2.95 (m, 2H), 3.3–3.5 (m, 1H), 3.64 (q, 1H, J=8 Hz), 3.6–3.8 (m, 1H), 4.44 (q, 1H, J=6.5 Hz), 6.85–6.95 (m, 2H), 6.95–7.05 (m, 2H), 7.35 (s, 2H), 7.64 (s, 1H). Mass spec (NH$_3$/CI): 548 (M +1). Similarly, the lower diastereomeric t-butyl ester afforded 4.9 mg of title compound. NMR (CDCl$_3$) δ1.32 (d, 3H, J=6.5 Hz), 1.7–1.9 (m, 2H), 2.0–2.2 (m, 2H), 2.2–2.4 (m, 3H), 2.5–2.75 (m, 3H), 2.75–3.1 (m, 3H), 3.2–3.4 (m, 1H), 3.64 (q, 1H, J=8 Hz), 3.6–3.8 (m, 1H), 4.42 (q, 1H, J=6.5 Hz), 6.85–6.95 (m, 2H), 6.95–7.05 (m, 2H), 7.35 (s, 2H), 7.64 (s, 1H). Mass spec (NH$_3$/CI): 548 (M+1).

EXAMPLE 21

1-(S)-(1-(R)-(3,5-Bis(trifluoromethyl)phenyl) ethoxy)-2-(R)-(4-fluorophenyl)-3-(R)-(((2-carboxylalkyl)methylamino)methyl)cyclopentane hydrochloride Method A Step A: 1-(S)-(1-(R)-(3,5-Bis(trifluoromethyl)phenyl) ethoxy)-2-(R)-(4-fluorophenyl)-3-(R)-(formyl) cyclopentane To a solution of 0.248 mL of oxalyl chloride in 8 mL of methylene chloride cooled to −70° C. was added dropwise 0.40 ml of DMSO. The reaction was stirred for 10–15 minutes and then a solution of 510 mg of 1-(S)-(1-(R)-(3,5-bis(trifluoromethyl)phenyl)ethoxy)-2-(R)-(4-fluorophenyl)-3-(R)-(hydroxymethyl)-cyclopentane from Example 19, Method A or B in 5 mL of methylene chloride was added dropwise at −70° C. The reaction was stirred for 1 hour before dropwise addition of 2.0 mL of DIPEA in 3 mL of methylene chloride. After 5 minutes, the dry ice/acetone bath was removed and the reaction was allowed to warm to room temperature over 1 hour. The reaction was then diluted with methylene chloride and water containing 5 mL of 2N hydrochloric acid and the layers were separated. The aqueous layer was reextracted with methylene chloride and the organic layers were washed with brine, dried over sodium sulfate, combined and evaporated. The residue was purified by FC (10% ethyl acetate/hexanes) to give 440 mg of title compound as a waxy solid.

Step B: 1-(S)-(1-(R)-(3,5-Bis(trifluoromethyl)phenyl)ethoxy)-2-(R)-(4-fluorophenyl)-3-(R)-(((2-benzyloxycarbonylethyl)methylamino)-methyl)cyclopentane To a solution of 500 mg of aldehyde from Step A in 5 mL of 1,2-dichloroethane was added 320 mg of N-methyl-β-alanine benzyl ester hydrochloride and 0.24 mL of DIPEA. After stirring at room temperature for 10 minutes, 470 mg of sodium triacetoxyborohydride was added. The reaction was stirred for 16 hr. The reaction was quenched with sat'd sodium bicarbonate and was extracted twice with methylene chloride. The organic layers were washed with brine, dried over sodium sulfate, combined and evaporated. The residue was purified by FC (20–30% ethyl acetate/hexanes) to give 564 mg of title compound.

Mass spec ($NH_3$/CI): 626 (M+1).

Step C: 1-(S)-(1-(R)-(3,5-Bis(trifluoromethyl)phenyl)ethoxy)-2-(R)-(4-fluorophenyl)-3-(R)-(((2-carboxylethyl)methylamino)methyl)-cyclopentane hydrochloride A solution of 560 mg of benzyl ester from Step B in 10 mL of methanol was hydrogenated over 100 mg of 10% Pd/C at 40 psi for 16 hours. The catalyst was removed by filtration and the filtrate was concentrated in vacuo. The residue was directly purified by FC (5–10% methanol in methylene chloride, then addition of 1% ammonium hydroxide and 1% water, and finally 15:83:1:1 methanol:methylene chloride:ammonium hydroxide:water) to give 443 mg of oil. This was taken up in isopropyl acetate and evaporated twice. The residue was then taken up in ether and the hydrochloride precipitated with the addition of 1.2 mL of 1M hydrochloric acid in ether. The solid was filtered and dried in vacuo to afford 435 mg of title compound as a white solid. NMR ($CD_3OD$) δ1.34 (d, 3 H, J=6.5 Hz), 1.7–1.85 (m, 1H), 1.85–2.0 (m, 1H), 2.15–2.35 (m, 2H), 2.35–2.5 (m, 1H), 2.6–2.85 (m, 3H), 2.74 (s, 3H), 2.85–3.0 (m, 1H), 3.0–3.5 (m, 3H), 3.81 (q, 1 H, J=8 Hz), 3.6–3.8 (m, 1H), 4.64 (q, 1 H, J=6.5 Hz), 6.97 (t, 2 H, J=8.8 Hz), 7.1–7.2 (m, 2H), 7.54 (s, 2H), 7.73 (s, 1H). Mass spec (ESI): 536 (M+1).

Method B

Using essentially the same procedures as in Example 20, but using N-methyl-β-alanine t-butyl ester in Step B, the t-butyl ester was prepared from the bromide of Step A. This was then treated with TFA to afford the title compound. NMR and mass spec were the same as Method A.

EXAMPLE 22

1-(S)-(1-(R)-(3,5-Bis(trifluoromethyl)phenyl)ethoxy)-2-(S)-(4-fluorophenyl)-3-(R)-((2-carboxylethyl)methylamino)cyclopentane Step A: 1-(S)-(1-(R)-(3,5-Bis(trifluoromethyl)phenyl)ethoxy)-2-(S)-(4-fluorophenyl)-3-(R)-((2-methoxycarbonylethyl)methylamino)-cyclopentane To a solution of 40 mg of 1-(S)-(1-(R)-(3,5-bis(trifluoromethyl)-phenyl)ethoxy)-2-(S)-(4-fluorophenyl)-3-(R)-(methylamino)cyclopentane from Example 15 in 1 mL of acetonitrile was added 0.011 mL of methyl 3-bromoproprionate and 0.046 mL of DIPEA. The reaction was heated at 50° C. for 24 hours, then an additional 0.011 mL of methyl 3-bromoproprionate and 0.030 mL of DIPEA were added and heating continued at 80° C. for 60 hours. The reaction was evaporated under a stream of nitrogen and the residue purified by prep TLC (5% methanol in methylene chloride) to give 39 mg of title compound. Mass spec (ESI): 536 (M+1).

Step B: 1-(S)-(1-(R)-(3,5-Bis(trifluoromethyl)phenyl)ethoxy)-2-(S)-(4-fluorophenyl)-3-(R)-((2-carboxylethyl)methylamino)cyclopentane To 39 mg of methyl ester from Step A in 1 mL of methanol was added 0.18 mL of 2N sodium hydroxide. The reaction was stirred at room temperature for 24 hours before being diluted with water, neutralized to pH=7 with 2N hydrochloric acid, and extracted twice with ether. The organic layers were washed with brine, dried over sodium sulfate, combined and evaporated to afford 29 mg of title compound. NMR ($CDCl_3$): δ1.35 (d, 3 H, J=6.5 Hz), 1.75–1.9 (m, 1H), 1.9–2.0 (m, 2H), 2.0–2.15 (m, 1H), 2.31 (s, 3H), 2.3–2.4 (m, 2H), 2.6–2.7 (m, 2H), 3.05 (dd, 1H, J=7.5 and 9.5 Hz), 3.25 (q, 1 H, J=8.5 Hz), 3.58 (q, 1 H, J=6.5 Hz), 4.45 (q, 1 H, J=6.5 Hz), 6.9–7.0 (m, 2H), 7.0–7.1 (m, 2H), 7.36 (s, 2H), 7.65 (s, 1H).

Mass spec (ESI): 522 (M +1).

EXAMPLE 23

1-(S)-(1-(R)-(3,5-Bis(trifluoromethyl)phenyl)ethoxy)-2-(S)-(4-fluorophenyl)-3-(R)-((3-carboxylpropyl)methylamino)cyclopentane Step A: 1-(S)-(1-(R)-(3,5-Bis(trifluoromethyl)phenyl)ethoxy)-2-(S)-(4-fluorophenyl)-3-(R)-((3-methoxycarbonylpropyl)methylamino)-cyclopentane To a solution of 40 mg of 1-(S)-(1-(R)-(3,5-bis(trifluoromethyl)phenyl)ethoxy)-2-(S)-(4-fluorophenyl)-3-(R)-(methylamino)cyclopentane from Example 15 in 1 mL of acetonitrile was added 0.011 mL of methyl 4-chlorobutyrate and 0.046 mL of DIPEA. The reaction was heated at 50° C. for 24 hours, then an additional 0.022 mL of methyl 4-chlorobutyrate, 0.030 mL of DIPEA and 3 mg of tetrabutylammonium iodide were added and heating continued at 80° C. for 60 hours. The reaction was evaporated under a stream of nitrogen and the residue purified by prep TLC (5% methanol in methylene chloride) to give 27 mg of title compound. Mass spec (ESI): 550 (M+1).

Step B: 1-(S)-(1-(R)-(3,5-Bis(trifluoromethyl)phenyl)ethoxy)-2-(S)-(4-fluorophenyl)-3-(R)-((3-carboxylpropyl)methylamino)cyclopentane To 27 mg of methyl ester from Step A in 1 mL of methanol was added 0.12 mL of 2N sodium hydroxide. The reaction was stirred at room temperature for 24 hours before being diluted with water, neutralized with 2N hydrochloric acid, and extracted twice with ether. The organic layers were washed with brine, dried over sodium sulfate, combine d and evaporated to afford 29 mg of title compound. NMR ($CDCl_3$): δ1.34 (d, 3 H, J=6.5 Hz), 1.7–2.0 (m, 3H), 2.05–2.15 (m, 1H), 2.15–2.3 (m, 2H), 2.3–2.4 (m, 2H), 2.51 (s, 3H), 2.7–2.85 (m, 1H), 2.85–2.95 (m, 1H), 3.34 (t, 1 H, J=8.5 Hz), 3.4–3.6 (m, 2H), 4.46 (q, 1 H, J=6.5 Hz), 6.9–7.0 (m, 2H), 7.0–7.1 (m, 2H), 7.31 (s, 2H), 7.65 (s, 1H). Mass spec (ESI): 536 (M+1).

EXAMPLE 24

1-(S)-(1-(R)-(3,5-Bis(trifluoromethyl)phenyl) ethoxy)-2-(R)-(4-fluorophenyl)-3-(R)-((3-carboxylpropyl)methylamino)methyl)cyclopentane Step A: 1-(S)-(1-(R)-(3,5-Bis(trifluoromethyl)phenyl) ethoxy)-2-(R)-(4-fluorophenyl)-3-(R)-(((3-methoxycarbonylpropyl)methylamino)-methyl) cyclopentane To a solution of 65 mg of 1-(S)-(1-(R)-(3,5-bis (trifluoromethyl)-phenyl)ethoxy)-2-(R)-(4-fluorophenyl)-3-(R)-((methylamino)methyl)cyclopentane from Example 18, Step B in 1 mL of acetonitrile was added 0.019 mL of methyl 4-chlorobutyrate and 0.037 mL of DIPEA. The reaction was heated at 50° C. for 48 hours, then an additional 0.038 mL of methyl 4-chlorobutyrate, 0.074 mL of DIPEA and 3 mg of tetrabutylammonium iodide were added and heating continued at 70° C. for 48 hours. The reaction was evaporated under a stream of nitrogen and the residue purified by prep TLC (10% methanol in ethyl acetate) to give 41 mg of title compound and 17 mg of recovered starting material. Mass spec (ESI): 564 (M+1).

Step B: 1(S)-(1-(R)-(3,5-Bis(trifluoromethyl)phenyl) ethoxy)-2-(R)-(4-fluorophenyl)-3-(R)-(((3-carboxylpropyl)methylamino)-methyl)cyclopentane To 41 mg of methyl ester from Step A in 1 mL of methanol was added 0.5 mL of 5N sodium hydroxide. The reaction was stirred at room temperature for 24 hours before being diluted with water, neutralized to pH=7 with 1.2 N hydrochloric acid, and evaporated to dryness in vacuo. The residue was purified by prep TLC (83:15:1:1 methylene chloride:methanol:ammonium hydroxide:water) to afford the title compound. NMR (CDCl$_3$): δ1.37 (d, 3 H, J=6.5 Hz), 1.7–1.8 (m, 3H), 1.8–1.9 (m, 1H), 2.05–2.25 (m, 3H), 2.32 (s, 3H), 2.4–2.7 (m, 7H), 3.67 (q, 1 H, J=7.5 Hz), 4.48 (q, 1 H, J=6.5 Hz), 6.9–7.0 (m, 2H), 7.0–7.05 (m, 2H), 7.41 (s, 2H), 7.41 (s, 2H), 7.67 (s, 1H).

Mass spec (ESI): 550 (M+1).

EXAMPLE 25

1-(S)-(1-(R)-(3,5-Bis(trifluoromethyl)phenyl) ethoxy)-2-(R)-(4-fluorophenyl)-3-(R)-((4-carboxylpiperidin-1-yl)methyl)cyclopentane Method A Using essentially the same procedures as in Example 20, but using 4-(t-butoxycarbonyl)piperidine in Step B, the t-butyl ester was prepared from the bromide of Step A. This was then treated with TFA to afford the title compound. NMR (CDCl$_3$): δ1.31 (d, 3 H, J=6.5 Hz), 1.5–1.8 (m, 4H), 1.8–1.95 (m, 2H), 1.95–2.2 (m, 4H), 2.2–2.35 (m, 2H), 2.35–2.5 (m, 1H), 2.55 (dd, 1 H, J=8 and 10 Hz), 2.55–2.8 (m, 1H), 3.0–3.25 (m, 2H), 3.61 (q, 1 H, J=7.5 Hz), 4.42 (q, 1 H, J=6.5 Hz), 6.9–7.0 (m, 2H), 7.0–7.05 (m, 2H), 7.34 (s, 2H), 7.64 (s, 1H).

Mass spec (ESI): 562 (M+1).

Method B

Using essentially the same procedures as in Example 21, Method A, but using 4-(benzyloxycarbonyl)piperidine in Step B, the benzyl ester was prepared from the aldehyde of Step A. This was then hydrogenated as in Example 21, Step C to afford the title compound. NMR and mass spec were the same as Method A.

EXAMPLE 26

1-(S)-(1-(R)-(3,5-Bis(trifluoromethyl)phenyl) ethoxy)-2-(R)-(4-fluorophenyl)-3-(R)-(4-carboxyl-4-methylpiperidin-1-yl)methyl)cyclopentane Using essentially the same procedures as in Example 21, Method A, but using 4-(benzyloxycarbonyl)-4-methylpiperidine in Step B, the benzyl ester was prepared from the aldehyde of Step A. This was then hydrogenated as in Example 21, Step C to afford the title compound.

NMR (CDCl$_3$): δ1.25 (s, 3H), 1.32 (d, 3 H, J=6.5 Hz), 1.75–1.95 (m, 2H), 1.95–2.25 (m, 4H), 2.25–2.55 (m, 4H), 2.60 (dd, 1 H, J=8 and 10 Hz), 2.55–2.75 (m, 2H), 2.88 (dd, 1 H, J=8 and 10 Hz), 3.15–3.25 (m, 1H), 3.25–3.45 (m, 1H), 3.61 (q, 1 H, J=7.5 Hz), 4.42 (q, 1 H, J=6.5 Hz), 6.9–7.0 (m, 2H), 7.0–7.05 (m, 2H), 7.35 (s, 2H), 7.64 (s, 1H).

Mass spec (ESI): 576 (M+1).

EXAMPLE 27

1-(S)-(1-(R)-(3,5-Bis(trifluoromethyl)phenyl) ethoxy)-2-(S)-(4-fluorophenyl)-3-(R)-((carboxylmethyl)methylamino) cyclopentane Step A: 1-(S)-(1-(R)-(3,5-Bis(trifluoromethyl)phenyl) ethoxy)-2-(S)-(4-fluorophenyl)-3-(R)-((methoxycarbonylmethyl)methylamino)-cyclopentane To a solution of 251 mg of 1-(S)-(1-(R)-(3,5-bis (trifluoromethyl)-phenyl)ethoxy)-2-(S)-(4-fluorophenyl)-3-(R)-(methylamino)cyclopentane from Example 15 in 6 mL of acetonitrile was added 0.108 mL of t-butyl bromoacetate and 0.36 mL of DIPEA. The reaction was heated at 50° C. for 5 hours and then concentrated in vacuo. The residue was diluted with water and extracted twice with ethyl acetate. The organic layers were washed with brine, dried with sodium sulfate, combined and evaporated. The residue was purified by FC (0–2.5% methanol in methylene chloride) to afford 294 mg of title compound. Mass spec (ESI): 564 (M+1).

Step B: 1-(S)-(1-(R)-(3,5-Bis(trifluoromethyl)phenyl) ethoxy)-2-(S)-(4-fluorophenyl)-3-(R)-((carboxylmethyl) methylamino)cyclopentane Following essentially the same procedure as in Example 20, Step C but using 12 mg of the product from Step A, 4.0 mg of the title compound was obtained. Mass spec (ESI): 508 (M+1).

EXAMPLE 28

1-(S)-(1-(R) -(3,5-Bis(trifluoromethyl)phenyl) ethoxy)-2-(R)-(4-fluorophenyl)-3-(R)-(((R)-2-carboxylpyrrolidin-1-yl)methyl)cyclopentane Using essentially the same procedures as in Example 20, but using (R)-2-(t-butoxycarbonyl)pyrrolidine in Step B, the t-butyl ester was prepared from the bromide of Step A. This was then treated with TFA to afford the title compound.

Mass spec (ESI): 548 (M+1).

EXAMPLE 29

1-(S)-(1-(R)-(3,5-Bis(trifluoromethyl)phenyl) ethoxy)-2-(R)-(4-fluorophenyl)-3-(R)-(((RS)-3-carboxylpiperidin-1-yl)methyl)cyclopentane Using essentially the same procedures as in Example 21, Method A, but using (S)-3-(benzyloxycarbonyl)piperidine in Step B, the benzyl ester was prepared from the aldehyde of Step A. This was then hydrogenated as in Example 21, Step C to obtain the title compound. Mass spec (ESI): 562 (M+1).

EXAMPLE 30

1-(S)-(1-(R)-(3,5-Bis(trifluoromethyl)phenyl) ethoxy)-2-(R)-(4-fluorophenyl)-3-(R)-((3-carboxylazetidin-1-yl)methyl)cyclopentane Using essentially the same procedures as in Example 21, Method A, but using 3-(benzyloxycarbonyl)azetidine in Step B, the benzyl ester was prepared from the aldehyde of Step A. This was then hydrogenated as in Example 21, Step C as in Example 21, Step C to obtain the title compound. Mass spec (ESI): 534 (M+1).

EXAMPLE 31

1-(S)-(1-(R)-(3,5-Bis(trifluoromethyl)phenyl) ethoxy)-2-(R)-(4-fluorophenyl)-3-(R)-(((2-carboxyethyl)amino)methyl)cyclopentane Using essentially the same procedures as in Example 21, Method A, but using benzyl β-alanine in Step B, the benzyl ester was prepared from the aldehyde of Step A. This was then hydrogenated as in Example 21, Step C to afford the title compound. Mass spec (ESI): 522 (M+1).

EXAMPLE 32

1-(S)-(1-(R)-(3,5-Bis(trifluoromethyl)phenyl) ethoxy)-2-(R)-(4-fluorophenyl)-3-(R)-(((carboxylmethyl)amino)methyl)cyclopentane Using essentially the same procedures as in Example 20, but using t-butyl glycine in Step B, the t-butyl ester was prepared from the bromide of Step A. This was then treated with TFA to afford the title compound. Mass spec (ESI): 508 (M+1).

EXAMPLE 33

1-(S)-(1-(R)-(3,5-Bis(trifluoromethyl)phenyl) ethoxy)-2-(R)-(4-fluorophenyl)-3-(R)-((((S)-1-carboxylethyl)amino)methyl)cyclopentane Using essentially the same procedures as in Example 20, but using t-butyl L-alanine in Step B, the t-butyl ester was prepared from the bromide of Step A. This was then treated with TFA to afford the title compound. Mass spec (ESI): 522 (M+1).

EXAMPLE 34

1-(S)-(1-(R)-(3,5-Bis(trifluoromethyl)phenyl) ethoxy)-2-(R)-(4-fluorophenyl)-3-(R)-((((R)-1-carboxylethyl)amino)methyl)cyclopentane Using essentially the same procedures as in Example 20, but using t-butyl D-alanine in Step B, the t-butyl ester was prepared from the bromide of Step A. This was then treated with TFA to afford the title compound.

Mass spec (ESI): 522 (M+1).

EXAMPLE 35

1-(S)-(1-(R)-(3,5-Bis(trifluoromethyl)phenyl) ethoxy)-2-(S)-(4-fluorophenyl)-3-(R)-(ethylamino) cyclopentane Following essentially the same procedures as in Example 3 thru 6 but using non-racemic ester/ether from Example 13 (lower $R_f$ α-methyl isomer) and iodoethane in Example 6, Step A, the title compound was prepared.

Mass spec (NH$_3$/CI): 464 (M+1).

EXAMPLE 36

1-(S)-(1-(R)-(3,5-Bis(trifluoromethyl)phenyl) ethoxy)-2-(R)-(4-fluorophenyl)-3-(R)-((4-(tetrazol-5-yl)piperidin-1-yl)methyl)cyclopentane Step A: N-Boc-4-(tetrazol-5-yl)piperidine To a solution of 0.513 g of N-Boc 4-cyanopiperidine in 5 mL of dioxane was added 0.71 mL of tri-n-butyl tin azide. The reaction was heated at 100° C. for 4 days and was then evaporated to a viscous oil. The residue was taken up in 5 mL of ether and treated with 10 mL of 2N hydrochloric acid in ether. The reaction was stirred for 1 hour and then the precipitate was filtered, washed well with ether and dried to afford 0.54 g the title compound as a tan solid.

Step B: 4-(Tetrazol-5-yl)piperidine

To 100 mg of the solid from Step A was added a solution of 0.30 mL of acetyl chloride in 5 mL of methanol (generates a methanol solution of hydrochloric acid). After 2.5 hours at room temperature, the reaction was evaporated to dryness, triturated twice with ether and vacuum dried to give the title compound as a tan solid.

Step C: 1-(S)-(1-(R)-(3,5-Bis(trifluoromethyl)phenyl) ethoxy)-2-(R)-(4-fluorophenyl)-3-(R)-(((4-(tetrazol-5-yl) piperidin-1-yl)methyl)cyclopentane To a solution of 40 mg of aldehyde prepared in Example 21, Step A in 1.0 mL of 1,2-dichloroethane was added 100 mg of powdered 3A molecular sieves, 45 mg of 4-(tetrazol-5-yl)piperidine from Step A and 0.041 mL of DIPEA. After 15 minutes, 57 mg of sodium triacetoxyborohydride was added and the reaction was stirred at room temperature for 5 hours. The reaction was quenched with water and extracted twice with methylene chloride. The organic layers were dried with sodium sulfate, combined and evaporated. The residue was purified by prep TLC (15:83:1:1 methanol:methylene chloride:ammonium hydroxide:water) to give 13 mg of title compound. Mass spec (ESI): 586 (M+1).

EXAMPLE 37

1-(S)-(1-(R)-(3,5-Bis(trifluoromethyl)phenyl) ethoxy)-2-(R)-(4-fluorophenyl)-3-(R)-(((2-(tetrazol-5-yl)ethyl)methylamino)methyl)cyclopentane Step A: N-Boc-N-methylalanine nitrile To a solution of 3.0 g of N-methylalanine nitrile in 70 mL of dioxane was added 8.1 g of di-t-butyldicarbonate and 7.49 g of sodium carbonate dissolved in 35 mL of water. The reaction was stirred at room temperature for 16 hours and was then poured into water and extracted twice with ether. The organic layers were washed with brine, dried over sodium sulfate, combined and concentrated. The residue was purified by FC (20% ethyl acetate in hexanes) to give 4.99 g of title compound as an oil.

Step B: N-Methyl-2-(tetrazol-5-yl)ethylamine

Following essentially the same procedures as used in Example 36, Steps A and B, the title compound was prepared.

Step C: 1-(S)-(1-(R)-(3,5-Bis(trifluoromethyl)phenyl) ethoxy)-2-(R)-(4-fluorophenyl)-3-(R)-(((2-(tetrazol-5-yl) ethyl)methylamino)methyl)-cyclopentane Following essentially the same procedures as used in Example 36, Step C, the title compound was prepared. Mass spec (ESI): 560 (M+1).

EXAMPLE 38

1-(S)-(1-(R)-(3,5-Bis(trifluoromethyl)phenyl) ethoxy)-2-(R)-(4-fluorophenyl)-3-(S)-((4-carboxylpiperidin-1-yl)methyl)cyclopentane Following essentially the same procedures as in Example 19 thru 22, but using non-racemic ether/ester from Example 14 (lower $R_f$ α-methyl isomer), the title 1,2-cis compound was prepared.

Mass spec (ESI): 562 (M+1).

EXAMPLE 39

1-(S)-(1-(R)-(3-Fluoro-5-trifluoromethyl)phenyl)ethoxy)-2-(R)-(4-fluorophenyl)-3-(R)-((4-carboxylpiperidin-1-yl)methyl)cyclopentane Following essentially the same procedures as in Example 8, but using (+/−)-1-(3-fluoro-5-trifluoromethylphenyl)ethyl bromide prepared as in Example 8, Step A and C, and subsequent reactions as in Examples 19, 20 and 25, the title compound was prepared. Mass spec (ESI): 512 (M+1).

EXAMPLE 40

1-(S)-(1-(R)-(3,5-Bis(trifluoromethyl)phenyl)ethoxy)-2-(R)-(4-fluorophenyl)-3-(R)-((4-(methylsulfonylaminocarbonyl)piperidin-1-yl)methyl)cyclopentane Step A: 1-(Benzyloxycarbonyl)-4-(methylsulfonylaminocarbonyl)piperidine To a solution of 200 mg of 1-(benzyloxycarbonyl)-4-carboxylpiperidine in 3 mL of methylene chloride was added a catalytic amount of DMF and 0.14 mL of oxalyl chloride. The reaction was stirred for 40 minutes and was then evaporated to dryness. The residue was taken up in 2 mL of THF.

Simultaneously, to 144 mg of methylsulfonamide in 1.5 mL of THF was added 66 mg of 60% sodium hydride and the mixture was stirred at room temperature. The above THF solution of acid chloride was then added and stirred for 2 hours. The reaction was then quenched with 2N hydrochloric acid and extracted twice with ethyl acetate. The organic layers were washed with brine, dried over sodium sulfate, combined and evaporated. The residue was purified by FC (20–40% ethyl acetate/hexanes, then 1% acetic acid in 40% ethyl acetate/hexanes) to give 197 mg of the title product.

Step B: 4-(Methylsulfonylaminocarbonyl)piperidine

The 197 mg of the product from Step A was taken up in 5 mL of methanol and hydrogenated at 40 psi over 60 mg of 10% Pd/C for 16 hours. The catalyst was removed by filtration and the solvent was removed in vacuo to afford 49 mg of title compound.

Step C: 1-(S)-(1-(R)-(3,5-Bis(trifluoromethyl)phenyl)ethoxy)-2-(R)-(4-fluorophenyl)-3-(R)-((4-(methylsulfonylaminocarbonyl)-piperidin-1-yl)methyl)cyclopentane Following essentially the same procedures as used in Example 36, Step C, the title compound was prepared. Mass spec (ESI): 639 (M+1).

EXAMPLE 41

1-(S)-(1-(3,5-Bis(trifluoromethyl)phenyl)methoxy)-2-(R)-(4-fluorophenyl)-3-(R)-(carboxyl)cyclopentane A solution of 5.0 g of 3-(S)-(hydroxy)-2-(R)-(4-fluorophenyl)cyclopentane-1-(R)-carboxylic acid from Example 13, Step E-3 in 50 mL of DMF was added to a suspension of 2.3 g of 60% sodium hydride at 0° C. The mixture was stirred for 10 minutes and then 4.1 mL of 3,5-bis(trifluoromethyl)benzyl bromide was added. The reaction was stirred for 2 hours while allowed to warm to room temperature. An additional 0.23 g of sodium hydride was added and after another 1 hour the reaction was quenched with water and extracted with ether. The aqueous layer was acidified with (c) hydrochloric acid to pH=2 and was extracted 3 times with ether. The organic layers were washed with brine, dried over sodium sulfate, combined and evaporated. The residue was purified by FC (40–50% ethyl acetate in hexanes then with 1% acetic acid to elute 7.35 g of the title product.

EXAMPLE 42

1-(S)-(1-(3,5-Bis(trifluoromethyl)phenyl)methoxy)-2-(R)-(4-fluorophenyl)-3-(R)-(hydroxymethyl)cyclopentane To a solution of 7.35 g of 1-(S)-(1-(3,5-bis(trifluoromethyl)phenyl)methoxy)-2-(R)-(4-fluorophenyl)-3-(R)-(carboxyl)cyclopentane from Example 41 in 32 mL of THF was added 12 mL of 2M borane methyl sulfide in THF. The reaction was stirred at room temperature for 16 hours and was then quenched with methanol and concentrated in vacuo to give 6.97 g of crude title compound which was used directly.

EXAMPLE 43

Following essentially the same procedures as in Example 21 thru 22, but using non-racemic ether/alcohol from Example 42, the following compounds were prepared.

1-(S)-(1-(3,5-Bis(trifluoromethyl)phenyl)methoxy)-2-(R)-(4-fluorophenyl)-3-(R)-((4-carboxylpiperidin-1-yl)methyl)cyclopentane NMR (CDCl$_3$): δ1.6–2.05 (m, 5H), 2.05–2.15 (m, 1H), 2.15–2.3 (m, 2H), 2.3–2.5 (m, 2H), 2.5–2.8 (m, 2H), 2.8–3.0 (m, 1H), 3.1–3.3 (m, 2H), 3.9 (m, 1H) 4.52 (ABq, 2H, J=13 Hz), 7.0 (m, 2H), 7.2 (br s, 2H), 7.57 (s, 2H), 7.74 (s, 1H).

Mass spec (ESI): 548 (M+1).

1-(S)-(1-(3,5-Bis(trifluoromethyl)phenyl)methoxy)-2-(R)-(4-fluorophenyl)-3-(R)-(((S)-2-carboxylpyrrolidin-1-yl)methyl)cyclopentane Mass spec (ESI): 534 (M+1).

1-(S)-(1-(3,5-Bis(trifluoromethyl)phenyl)methoxy)-2-(R)-(4-fluorophenyl)-3-(R)-(((R,S)-3-carboxylpyrrolidin-1-yl)methyl)cyclopentane Mass spec (ESI): 534 (M+1).

1-(S)-(1-(3,5-Bis(trifluoromethyl)phenyl)methoxy)-2-(R)-(4-fluorophenyl)-3-(R)-(((2-carboxylethyl)amino)methyl)cyclopentane Mass spec (ESI): 522 (M+1).

1-(S)-(1-(3,5-Bis(trifluoromethyl)phenyl)methoxy)-2-(R)-(4-fluorophenyl)-3-(R)-(((2-carboxylethyl)methylamino)methyl)cyclopentane

EXAMPLE 44

1-(S)-(1-(S)-(3,5-Bis(trifluoromethyl)phenyl)-2-hydroxyethoxy)-2-(R)-(4-fluorophenyl)-3-(R)-(hydroxymethyl)cyclopentane Step A: 1-(S)-(Hydroxy)-2-(R)-(4-fluorophenyl)cyclopentane-3-(R)-(hydroxymethyl)cyclopentane To a solution of 1.0 g of 3-(S)-(hydroxy)-2-(R)-(4-fluorophenyl)cyclopentane-1-(R)-carboxylic acid from Example 13, Step E-3 was in 9 mL of THF was added 3.4 mL of 2M borane-methyl sulfide solution in THF. The reaction was stirred at room temperature for 3 hours and then quenched with methanol, stirred for 0.5 hour and then evaporated to give 1.09 g of crude product which was used directly in Step B.

Step B: 1-(S)-(Hydroxy)-2-(R)-(4-fluorophenyl)cyclopentane-3-(R)-(t-butyldimethylsilyloxymethyl)cyclopentane To a solution of crude alcohol from Step A in 20 mL of methylene chloride was added 1.1 mL of DIPEA and then 0.863 g of t-butyldimethylsilyl chloride. The reaction was stirred at room temperature for 16 hours and was then quenched with water and extracted 3 times with methylene chloride. The organic layers were washed with brine, dried over sodium sulfate, combined and evaporated. The residue was purified by FC (20–30% ethyl acetate/hexanes) to give 0.56 g of title compound.

Step C: 1-(S)-(Benzoyloxy)-2-(R)-(4-fluorophenyl) cyclopentane-3-(R)-(t-butyldimethylsilyloxymethyl) cyclopentane To an ice bath cooled solution of 0.56 g of 1-(S)-(hydroxy)-2-(R)-(4-fluorophenyl)cyclopentane-3-(R)-(t-butyldimethylsilyloxymethyl)-cyclopentane from Step B in 7 mL of methylene chloride was added 0.29 mL of DIPEA and then 0.525 g of bis-(3,5-trifluoromethylbenzoyl chloride. The reaction was stirred at 0° C. for 10 minutes, allowed to warm to room temperature over 30 minutes and was then quenched with water and extracted 3 times with methylene chloride. The organic layers were washed with brine, dried over sodium sulfate, combined and evaporated. The residue was purified by FC (1–2.5% ethyl acetate/hexanes) to give 0.77 g of title compound.

Step D: 1-(S)-(1-(3,5-Bis(trifluoromethyl)phenyl)ethen-1-yloxy)-2-(R)-(4-fluorophenyl)cyclopentane-3-(R)-(t-butyldimethylsilyloxymethyl)cyclopentane To a solution of 0.77 g of 1-(S)-(benzoyloxy)-2-(R)-(4-fluorophenyl)-cyclopentane-3-(R)-(t-butyldimethylsilyloxymethyl)-cyclopentane from Step C in 3 mL of THF was added 4.5 mL of a solution of 1M dimethyltitanocene in toluene. The reaction was heated in the dark at 95° C. for 16 hours, then cooled to room temperature and diluted with ether to precipitate the titanium salts. The mixture was filtered thru Celite and the filtrate was evaporated. The residue was purified by FC (2% ethyl acetate/hexanes) to give 0.45 g of title compound.

Step E: 1-(S)-(1-(R)-(3,5-Bis(trifluoromethyl)phenyl)-2-hydroxyethoxy)-2-(R)-(4-fluorophenyl)cyclopentane-3-(R)-(t-butyldimethylsilyloxymethyl)cyclopentane (higher $R_f$) and 1-(S)-(1-(S)-(3,5-Bis(trifluoromethyl)phenyl)-2-hydroxyethoxy)-2-(R)-(4-fluorophenyl)cyclopentane-3-(R)-(t-butyldimethylsilyloxymethyl)cyclopentane (lower $R_f$)

To a solution of 0.45 g of 1-(S)-(1-(3,5-bis(trifluoromethyl)phenyl)ethen-1-yloxy)-2-(R)-(4-fluorophenyl)-cyclopentane-3-(R)-(t-butyldimethylsilyloxymethyl)cyclopentane in 4 mL of THF was added 1.6 niL of 1M borane in THF. The reaction was stirred at room temperature for 1 hour and was then quenched with 0.7 mL of 30% hydrogen peroxide in water and 1.1 mL of 1M sodium hydroxide. The mixture was stirred at room temperature for 30 minutes and was then diluted with water and extracted 3 times with ether. The organic layers were washed with brine, dried over sodium sulfate, combined and evaporated. The residue was purified by FC (5–10% ethyl acetate/hexanes) to give 0.22 g the higher $R_f$ diastereomer and 0.22 g of the lower $R_f$ diastereomer of title compound.

Step F: 1-(S)-(1-(S)-(3,5-Bis(trifluoromethyl)phenyl)-2-hydroxyethoxy)-2-(R)-(4-fluorophenyl)cyclopentane-3-(R)-(t-butyldimethylsilyloxymethyl)cyclopentane To a solution of 0.18 g of lower $R_f$ product from Step E in 2 mL of methylene chloride was added 0.19 mL of DIPEA and 0.11 mL of benzyl chloroformate. The reaction was stirred at room temperature for 3 days and then additional aliquots of DIPEA and benzyl chloroformate were added. The mixture was heated to 55° C. for 3 hours before being quenched with water and extracted 3 times with methylene chloride. The organic layers were washed with brine, dried over sodium sulfate, combined and evaporated. The residue was purified by FC (10% ethyl acetate/hexanes) to give 0.14 g of title compound.

Step G: 1-(S)-(1-(S)-(3,5-Bis(trifluoromethyl)phenyl)-2-(benzyloxycarbonyloxy)ethoxy)-2-(R)-(4-fluorophenyl)cyclopentane-3-(R)-(hydroxymethyl)cyclopentane To a solution of 0.14 g of product from Step F in 1 mL of THF was added 0.4 mL of 1M tetrabutylammonium fluoride. The reaction was stirred at room temperature for 40 minutes before being quenched with water and extracted 3 times with ethyl acetate. The organic layers were washed with brine, dried over sodium sulfate, combined and evaporated. The residue was purified by FC (50% ethyl acetate/hexanes) to give 57 mg of title compound.

EXAMPLE 45

1-(S)-(1-(S)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane Step A: 1-(S)-(1-(S)-(3,5-Bis(trifluoromethyl)phenyl)-2-(benzyloxycarbonyloxy)ethoxy)-2-(R)-(4-fluorophenyl)cyclopentane-3-(R)-(formyl)-cyclopentane Following essentially the same procedure as in Example 21, Step A but using non-racemic ether/alcohol (57 mg) from Example 44, Step G, the title compound (67 mg crude) was prepared.

Step B: 1-(S)-(1-(S)-(3,5-Bis(trifluoromethyl)phenyl)-2-(benzyloxycarbonyloxy)ethoxy)-2-(R)-(4-fluorophenyl)-3-(R)-((4-benzyloxycarbonylpiperidin-1-yl)methyl)cyclopentane Following essentially the same procedure as in Example 21, Step B but using the 36 mg of crude product from Step A, the title compound (28 mg) was prepared.

Step C: 1-(S)-(1-(S)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane Following essentially the same procedure as in Example 21, Step C but using the 28 mg of product from Step B, the title compound (9 mg) was prepared.

Mass spec (ESI): 578 (M+1).

EXAMPLE 46

1-(S)-(1-(R)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane Following essentially the same procedures as in Example 44, Steps F and G and Example 45, but starting with the higher $R_f$ non-racemic ether/alcohol from Example 44, Step E, the title compound was prepared. Mass spec (ESI): 578 (M+1).

EXAMPLE 47

1-(S)-(1-(S)-(3,5-Bis(trifluoromethyl)phenyl)-2-hydroxyethoxy)-2-(R)-(4-fluorophenyl)-3-(R)-((((2-carboxylethyl)methyl)amino)methyl)cyclopentane Following essentially the same procedures as in Example 45, but using benzyl N-methyl-β-alanine in Step B, the non-racemic ether/alcohol from Example 44, Step G was converted to the title compound. Mass spec (ESI): 552 (M+1).

EXAMPLE 48

1-(S)-(1-(S)-(3,5-Bis(trifluoromethyl)phenyl)-2-hydroxyethoxy)-2-(R)-(4-fluorophenyl)-3-(R)-(((R,S)-3-carboxylpyrrolidin-1-yl)methyl)cyclopentane Step A: 1-(S)-(1-(S)-(3,5-Bis(trifluoromethyl)phenyl)-2-acetoxyethoxy)-2-(R)-(4-fluorophenyl)-3-(R)-(hydroxymethyl)cyclopentane Following essentially the same procedures as in Example 44, Step F and G but using acetyl chloride in Step F, the title non-racemic ether/alcohol was obtained.

Step B: 1-(S)-(1-(S)-(3,5-Bis(trifluoromethyl)phenyl)-2-acetoxyethoxy)-2-(R)-(4-fluorophenyl)-3-(R)-(((R,S)-3-t-butylcarbonylpyrrolidin-1-yl)methyl)cyclopentane Following essentially the same procedures as in Example 45, but using (R,S)-t-butyl β-proline in Step B, the non-racemic ether/alcohol from Step A was converted to the title compound.

Step C: 1-(S)-(1-(S)-(3,5-Bis(trifluoromethyl)phenyl)-2-hydroxyethoxy)-2-(R)-(4-fluorophenyl)-3-(R)-(((R,S)-3-carboxylpyrrolidin-1-yl)methyl)-cyclopentane To 24 mg of product from Step B was added 1 mL of TFA. The solution was stirred at room temperature for 1 hr and then concentrated in vacuo. The residue was taken up in 2 mL of methanol containing 0.1 mL of acetyl chloride to generate hydrochloric acid. The mixture was stirred at room temperature for 2 hours and then concentrated in vacuo. An NMR of the residue indicated that the product was mostly the methyl ester of the title compound. Thus, the residue was taken up in 1 mL of methanol and treated with 0.25 mL of 5N sodium hydroxide at room temperature for 3 hours. The mixture was neutralized to pH=7 with 1.2 N hydrochloric acid and evaporated to dryness. The residue was taken up in methylene chloride and purified by Prep TLC (15:83:1:1 methanol:methylene chloride:ammonium hydroxide: water) to afford 7.2 mg of title compound.

Mass spec (ESI): 564 (M+1).

EXAMPLE 49

1-(S)-(1-(S)-(3,5-Bis(trifluoromethyl)phenyl)-2-hydroxyethoxy)-2-(R)-(4-fluorophenyl)-3-(R)-((4-carboxyl-4-methylpiperidin-1-yl)methyl)cyclopentane Following essentially the same procedures as in Example 45 and 48, but using 4-benzyloxycarbonyl-4-methylpiperidine, the title compound was prepared.

Mass spec (ESI): 592 (M+1).

EXAMPLE 50

1-(S)-(1-(S)-(3,5-Bis(trifluoromethyl)phenyl)-2-hydroxyethoxy)-2-(R)-(4-fluorophenyl)-3-(R)-(((R and S)-3-carboxylpiperidin-1-yl)methyl)cyclopentane Following essentially the same procedures as in Example 45 and 48, but using (R,S)-3-benzyloxycarbonylpiperidine, the title compound was prepared. The intermediate diastereomer benzyl esters from the reductive amination step were separable and were carried individually thru the remaining steps.

Higher $R_f$: Mass spec (ESI): 578 (M+1).
Lower $R_f$: Mass spec (ESI): 578 (M+1).

EXAMPLE 51

1-(S)-(1-(R)-(3,5-Bis(trifluoromethyl)phenyl)ethoxy)-2-(R)-(4-fluorophenyl)-3-(R)-(((S)-3-carboxylpiperidin-1-yl)methyl)cyclopentane Using essentially the same procedures as in Example 21, Method A, but using (R)-3-(ethoxycarbonyl)-3-methylpiperidine in Step B, the ethyl ester was prepared from the aldehyde of Step A. This was then converted to the title compound as in Example 22, Step B.

Mass spec (ESI): 562 (M+1).

EXAMPLE 52

1-(S)-(1-(R)-(3,5-Bis(trifluoromethyl)phenyl)ethoxy)-2-(R)-(4-fluorophenyl)-3-(R)-(((RS)-3-carboxylpiperazin-1-yl)methyl)cyclopentane Using essentially the same procedures as in Example 21, Method A, but using (RS)-3-(methoxycarbonyl)piperazine in Step B, the methyl ester was prepared from the aldehyde of Step A. This was then hydrolyzed to the title compound as in Example 22, Step B.

Mass spec (ESI): 563 (M+1).

EXAMPLE 53

1-(S)-(1-(R)-(3,5-Bis(trifluoromethyl)phenyl)ethoxy)-2-(R)-(4-fluorophenyl)-3-(R)-(((RS)-2-carboxyl-1-methylpiperazin-4-yl)methyl)cyclopentane Using essentially the same procedures as in Example 21, Method A, but using (RS)-2-(methoxycarbonyl)-1-methylpiperazine in Step B, the methyl ester was prepared from the aldehyde of Step A. This was then hydrolyzed to the title compound as in Example 22, Step B.

Mass spec (ESI): 577 (M+1).

EXAMPLE 54

1-(S)-(1-(R)-(3,5-Bis(trifluoromethyl)phenyl)ethoxy)-2-(R)-(4-fluorophenyl)-3-(R)-(((RS)-2-carboxylmorpholin-4-yl)methyl)cyclopentane Using essentially the same procedures as in Example 21, Method A, but using (RS)-2-(methoxycarbonyl)morpholine in Step B, the methyl ester was prepared from the aldehyde of Step A. This was then hydrolyzed to the title compound as in Example 22, Step B.

Mass spec (ESI): 564 (M+1).

EXAMPLE 55

1-(S)-(1-(R)-(3,5-Bis(trifluoromethyl)phenyl)ethoxy)-2-(R)-(4-fluorophenyl)-3-(R)-(((R)-3-carboxyl-3-methylpiperidin-1-yl)methyl)cyclopentane Using essentially the same procedures as in Example 21, Method A, but using (R)-3-(ethoxycarbonyl)-3-methylpiperidine in Step B, the ethyl ester was prepared from the aldehyde of Step A. This was then hydrolyzed to the title compound as in Example 22, Step B.

Mass spec (ESI): 576 (M+1).

EXAMPLE 56

1-(S)-(1-(R)-(3,5-Bis(trifluoromethyl)phenyl)ethoxy)-2-(R)-(4-fluorophenyl)-3-(R)-(((S)-3-carboxyl-3-methylpiperidin-1-yl)methyl)cyclopentane Using essentially the same procedures as in Example 21, Method A, but using (S)-3-(ethoxycarbonyl)-3-methylpiperidine in Step B, the ethyl ester was prepared from the aldehyde of Step A. This was then hydrolyzed to the title compound as in Example 22, Step B.

Mass spec (ESI): 576 (M+1).

EXAMPLE 57

1-(S)-(1-(R)-(3,5-Bis(trifluoromethyl)phenyl) ethoxy)-2-(R)-(4-fluorophenyl)-3-(R)-(((R)-2-carboxylpiperidin-1-yl)methyl)cyclopentane and 1-(S)-(1-(R)-(3,5-Bis(trifluoromethyl)phenyl)ethoxy)-2-(R)-(4-fluorophenyl)-3-(R)-(((S)-2-carboxylpiperidin-1-yl)methyl)cyclopentane Using essentially the same procedures as in Example 21, Method A, but using (RS)-2-(methoxycarbonyl)piperidine in Step B, the diastereomeric methyl esters was prepared from the aldehyde of Step A. Separation on silica gel plates afforded the separate diastereomers. These were then hydrolyzed to the title compounds as in Example 22, Step B.

Mass spec (ESI): 562 (M+1).

EXAMPLE 58

1-(S)-(1-(R)-(3,5-Bis(trifluoromethyl)phenyl) ethoxy)-2-(R)-(4-fluorophenyl)-3-(R)-(((1-carboxyl-1-methyl)ethyl)aminomethyl)cyclopentane Using essentially the same procedures as in Example 21, Method A, but using dimethylglycine t-butyl ester in Step B, the t-butyl ester was prepared from the aldehyde of Step A. This was then treated with TFA to obtain the title compound.

Mass spec (ESI): 536 (M+1).

EXAMPLE 59

1-(S)-(1-(R)-(3,5-Bis(trifluoromethyl)phenyl) ethoxy)-2-(R)-(4-fluorophenyl)-3-(R)-((((R)-1-carboxyl-1,2-dimethylprop-1-yl)amino)methyl) cyclopentane and 1-(S)-(1-(R)-(3,5-bis (trifluoromethyl)phenyl)ethoxy)-2-(R)-(4-fluorophenyl)-3-(R)-((((S)-1-carboxyl-1,2-dimethylprop-1-yl)aminomethyl)cyclopentane Using essentially the same procedures as in Example 21, Method A, but using D/L methylvaline t-butyl ester in Step B, the diastereomeric t-butyl esters were prepared from the aldehyde of Step A. Separation on silica gel plates (20% ethyl acetate in hexanes) afforded the separate diastereomers. These were then individually treated with TFA to obtain the title compounds.

Mass spec (ESI): 564 (M+1).

EXAMPLE 60

1-(S)-(1-(R)-(3,5-Bis(trifluoromethyl)phenyl) ethoxy)-2-(R)-(4-fluorophenyl)-3-(R)-(((R)-3-carboxyl-(R)-5-methylpiperidin-1-yl)methyl) cyclopentane Using essentially the same procedures as in Example 21, Method A, but using (R)-3-methoxycarbonyl-(R)-5-methylpiperidine in Step B, the methyl ester was prepared from the aldehyde of Step A. This was then converted to the title compound as in Example 22, Step B.

Mass spec (ESI): 576 (M+1).

EXAMPLE 61

1-(S)-(1-(R)-(3,5-Bis(trifluoromethyl)phenyl) ethoxy)-2-(R)-(4-fluorophenyl)-3-(R)-(((R)-3-carboxyl-(S)-5-methylpiperidin-1-yl)methyl) cyclopentane Using essentially the same procedures as in Example 21, Method A, but using (R)-3-methoxycarbonyl-(S)-5-methylpiperidine in Step B, the methyl ester was prepared from the aldehyde of Step A. This was then converted to the title compound as in Example 22, Step B.

Mass spec (ESI): 576 (M+1).

EXAMPLE 62

1-(S)-(1-(R)-(3,5-Bis(trifluoromethyl)phenyl) ethoxy)-2-(R)-(4-fluorophenyl)-3-(R)-(((S)-3-carboxyl-(R)-5-methylpiperidin-1-yl)methyl) cyclopentane Using essentially the same procedures as in Example 21, Method A, but using (S)-3-methoxycarbonyl-(R)-5-methylpiperidine in Step B, the methyl ester was prepared from the aldehyde of Step A. This was then converted to the title compound as in Example 22, Step B.

Mass spec (ESI): 576 (M+1).

EXAMPLE 63

1-(S)-(1-(R)-(3,5-Bis(trifluoromethyl)phenyl) ethoxy)-2-(R)-(4-fluorophenyl)-3-(R)-(((S)-3-carboxyl-(S)-5-methylpiperidin-1-yl)methyl) cyclopentane Using essentially the same procedures as in Example 21, Method A, but using (S)-3-methoxycarbonyl-(S)-5-methylpiperidine in Step B, the methyl ester was prepared from the aldehyde of Step A. This was then converted to the title compound as in Example 22, Step B.

Mass spec (ESI): 576 (M+1).

EXAMPLE 64

1-(S)-(1-(R)-(3,5-Bis(trifluoromethyl)phenyl) ethoxy)-2-(R)-(4-fluorophenyl)-3-(R)-(((R)-2-carboxyl-(R)-5-methylpiperidin-1-yl)methyl) cyclopentane Using essentially the same procedures as in Example 21, Method A, but using (R)-3-methoxycarbonyl-(R)-5-methylpiperidine in Step B, the methyl ester can be prepared from the aldehyde of Step A. This can then be converted to the title compound as in Example 22, Step B.

EXAMPLE 65

1-(S)-(1-(R)-(3,5-Bis(trifluoromethyl)phenyl) ethoxy)-2-(R)-(4-fluorophenyl)-3-(R)-(((R)-2-carboxyl-(S)-5-methylpiperidin-1-yl)methyl) cyclopentane Using essentially the same procedures as in Example 21, Method A, but using (R)-3-methoxycarbonyl-(S)-5-methylpiperidine in Step B, the methyl ester can be prepared from the aldehyde of Step A. This can then be converted to the title compound as in Example 22, Step B.

EXAMPLE 66

1-(S)-(1-(R)-(3,5-Bis(trifluoromethyl)phenyl) ethoxy)-2-(R)-(4-fluorophenyl)-3-(R)-(((S)-2-carboxyl-(R)-5-methylpiperidin-1-yl)methyl) cyclopentane Using essentially the same procedures as in Example 21, Method A, but using (S)-3-methoxycarbonyl-(R)-5-methylpiperidine in Step B, the methyl ester can be prepared from the aldehyde of Step A. This can then be converted to the title compound as in Example 22, Step B.

EXAMPLE 67

1-(S)-(1-(R)-(3,5-Bis(trifluoromethyl)phenyl)
ethoxy)-2-(R)-(4-fluorophenyl)-3-(R)-(((S)-2-
carboxyl-(S)-5-methylpiperidin-1-yl)methyl)
cyclopentane Using essentially the same procedures as in Example 21, Method A, but using (S)-3-methoxycarbonyl-(S)-5-methylpiperidine in Step B, the methyl ester can be prepared from the aldehyde of Step A. This can then be converted to the title compound as in Example 22, Step B.

EXAMPLE 68

1-(S)-(1-(R)-(3,5-Bis(trifluoromethyl)phenyl)
ethoxy)-2-(R)-(4-fluorophenyl)-3-(R)-((((S)-1-
carboxylethyl)methylamino)methyl)cyclopentane Using essentially the same procedures as in Example 21, Method A, but using (S)-N-methylalanine t-butyl ester in Step B, the t-butyl ester can be prepared from the aldehyde of Step A. This can then be treated with TFA to obtain the title compound. Mass spec (ESI): 536 (M+1).

EXAMPLE 69

1-(S)-(1-(R)-(3,5-Bis(trifluoromethyl)phenyl)
ethoxy)-2-(R)-(4-fluorophenyl)-3-(R)-((((R)-1-
carboxylethyl)methylamino)methyl)cyclopentane Using essentially the same procedures as in Example 21, Method A, but using (R)-N-methylalanine t-butyl ester in Step B, the t-butyl ester can be prepared from the aldehyde of Step A. This can then be treated with TFA to obtain the title compound. Mass spec (ESI): 536 (M+1).

EXAMPLE 70

1-(S)-(1-(R)-(3,5-Bis(trifluoromethyl)phenyl)
ethoxy)-2-(R)-(4-fluorophenyl)-3-(R)-((((RS)-2-
carboxylprop-1-yl)methylamino)methyl)
cyclopentane Using essentially the same procedures as in Example 21, Method A, but using t-butyl (RS)-N-methyl-2-methyl-3-aminopropanoate in Step B, the t-butyl ester can be prepared from the aldehyde of Step A. This can then be treated with TFA to obtain the title compound. Mass spec (ESI): 550 (M+1).

EXAMPLE 71

1-(S)-(1-(S)-(3,5-Bis(trifluoromethyl)phenyl)-2-
hydroxyethoxy)-2-(R)-(4-fluorophenyl)-3-(R)-(((R)-
3-carboxyl-3-methylpiperidin-1- yl)methyl)
cyclopentane Following essentially the same procedures as in Example 45 and 48, but using (R)-3-benzyloxycarbonyl-3-methylpiperidine, the title compound was prepared. Mass spec (ESI): 592 (M+1).

EXAMPLE 72

1-(S)-(1-(S)-(3,5-Bis(trifluoromethyl)phenyl)-2-
hydroxyethoxy)-2-(R)-(4-fluorophenyl)-3-(R)-(((S)-
3-carboxyl-3-methylpiperidin-1-yl)methyl)
cyclopentane Following essentially the same procedures as in Example 45 and 48, but using (S)-3-benzyloxycarbonyl-3-methylpiperidine, the title compound was prepared. Mass spec (ESI): 592 (M+1).

EXAMPLE 73

1-(S)-(1-(R)-(3,5-Bis(trifluoromethyl)phenyl)
ethoxy)-2-(S)-(4-fluorophenyl)-3-(R)-((2-carboxyl-
2-methylprop-1-yl)methylamino)cyclopentane Using essentially the same procedures as in Example 21, Method A, but using 1-(S)-(1-(R)-(3,5-bis(trifluoromethyl)phenyl)ethoxy)-2-(S)-(4-fluorophenyl)-3-(R)-(methylamino)cyclopentane from Example 15 and 4-methoxybenzyl 2,2-dimethyl-3-oxopropanoate, the benzyl ester was prepared in Step A. This was then hydrogenated as in Example 21, Step C to afford the title compound. Mass spec (ESI): 550 (M+1).

EXAMPLE 74

1-(S)-(1-(R)-(3,5-Bis(trifluoromethyl)phenyl)
ethoxy)-2-(S)-(4-fluorophenyl)-3-(R)-((2-carboxyl-
2-ethylbut-1-yl)methylamino)cyclopentane Using essentially the same procedures as in Example 21, Method A, but using 1-(S)-(1-(R)-(3,5-bis(trifluoromethyl)phenyl)ethoxy)-2-(S)-(4-fluorophenyl)-3-(R)-(methylamino)cyclopentane from Example 15 and 4-methoxybenzyl 2,2-diethyl-3-oxopropanoate, the benzyl ester was prepared in Step A. This was then hydrogenated as in Example 21, Step C to afford the title compound.

Mass spec (ESI): 578 (M+1).

EXAMPLE 75

1-(S)-(1-(R)-(3,5-Bis(trifluoromethyl)phenyl)
ethoxy)-2-(R)-(4-fluorophenyl)-3-(R)-(((1-
carboxylcyclopent-1-yl)methyl)methylamino)
cyclopentane Using essentially the same procedures as in Example 21, Method A, but using 1-(S)-(1-(R)-(3,5-bis(trifluoromethyl)phenyl)ethoxy)-2-(S)-(4-fluorophenyl)-3-(R)-(methylamino)cyclopentane from Example 15 and 4-methoxybenzyl 1-formylcyclopentane carboxylate, the benzyl ester was prepared in Step A. This was then hydrogenated as in Example 21, Step C to afford the title compound. Mass spec (ESI): 576 (M+1).

EXAMPLE 76

1-(S)-(1-(R)-(3,5-Bis(trifluoromethyl)phenyl)
ethoxy)-2-(R)-(4-fluorophenyl)-3-(R)-((1-
carboxylcyclohex-1-ylamino)methyl)cyclopentane Using essentially the same procedures as in Example 21, Method A, but using 1-aminocyclohexane carboxylic acid t-butyl ester in Step B, the t-butyl ester was prepared from the aldehyde of Step A. This was then treated with TFA to obtain the title compound. Mass spec (ESI): 576 (M+1).

EXAMPLE 77

1-(S)-(1-(R)-(3,5-Bis(trifluoromethyl)phenyl)
ethoxy)-2-(R)-(4-fluorophenyl)-3-(R)-((1-
carboxylcyclopent-1-ylamino)methyl)cyclopentane Using essentially the same procedures as in Example 21, Method A, but using 1-aminocyclopentane carboxylic acid t-butyl ester in Step B, the t-butyl ester was prepared from the aldehyde of Step A. This was then treated with TFA to obtain the title compound. Mass spec (ESI): 562 (M+1).

EXAMPLE 78

1-(S)-(1-(R)-(3,5-Bis(trifluoromethyl)phenyl)
ethoxy)-2-(R)-(4-fluorophenyl)-3-(R)-(((1-
carboxylcyclohex-1-yl)methylamino)methyl)
cyclopentane Using essentially the same procedures as in Example 21, Method A, but using 1-(S)-(1-(R)-(3,5-bis(trifluoromethyl) phenyl)ethoxy)-2-(R)-(4-fluorophenyl)-3-(R)-((1-t-butoxycarbonylcyclohex-1-ylamino)methyl)cyclopentane from Example 76 and formaldehyde in Step B, the t-butyl ester was prepared. This was then treated with TFA to afford the title compound.

Mass spec (ESI): 590 (M+1).

EXAMPLE 79

1-(S)-(1-(R)-(3,5-Bis(trifluoromethyl)phenyl)
ethoxy)-2-(R)-(4-fluorophenyl)-3-(R)-(((1-
carboxylcyclopent-1-yl)methylamino)methyl)
cyclopentane Using essentially the same procedures as in Example 21, Method A, but using 1-(S)-(1-(R)-(3,5-bis(trifluoromethyl) phenyl)ethoxy)-2-(R)-(4-fluorophenyl)-3-(R)-((1-t-butoxycarbonylcyclopent-1-ylamino)methyl)cyclopentane from Example 77 and formaldehyde in Step B, the t-butyl ester was prepared. This was then treated with TFA to afford the title compound.

Mass spec (ESI): 576 (M+1).

EXAMPLE 80

1-(S)-(1-(R)-(3,5-Bis(trifluoromethyl)phenyl)
ethoxy)-2-(R)-(4-fluorophenyl)-3-(R)-(((R)-3-
carboxylpiperidin-1-yl)methyl)cyclopentane Step A: 1-(S)-(1-(R)-(3,5-Bis(trifluoromethyl)phenyl) ethoxy)-2-(R)-(4-fluorophenyl)-3-(R)-(formyl) cyclopentane To a solution of 5.4 mL (61.7 mmole) of oxalyl chloride in 100 mL of methylene chloride cooled to −70° C. was added dropwise 8.7 mL (123 mmole) of DMSO. The reaction was stirred for 10–15 minutes at −70° C. and then a solution of 11.11 g (24.7 mmole) of 1-(S)-(1-(R)-(3,5-bis (trifluoromethyl)phenyl)ethoxy)-2-(R)-(4-fluorophenyl)-3-(R)-(hydroxymethyl)cyclopentane, prepared as in Example 19, Step A, in 40 mL of methylene chloride was added dropwise at −70° C. The reaction was stirred for 1 hour before dropwise addition of 43 mL (246 mmole) of DIPEA in 25 mL of methylene chloride. After 5 minutes, the dry ice/acetone bath was removed and the reaction was warmed to room temperature in a water bath and stirred for 1 hour. The reaction was then diluted with methylene chloride and water containing 150 mL of 2N hydrochloric acid and the layers were separated. The aqueous layer was reextracted with methylene chloride and the organic layers were each washed with a portion of brine, dried over sodium sulfate, combined and evaporated. The residue was purified by FC (10% ethyl acetate/hexanes) to give 9.8 g of title compound as a waxy solid.

Step B: 1-(S)-(1-(R)-(3,5-Bis(trifluoromethyl)phenyl) ethoxy)-2-(R)-(4-fluorophenyl)-3-(R)-(((R)-3-ethoxycarbonylpiperidin-1-yl)methyl)cyclopentane To a solution of 9.8 g (22 mmole) of 1-(S)-(1-(R)-(3,5-bis(trifluoromethyl)phenyl)ethoxy)-2-(R)-(4-fluorophenyl)-3-(R)-(formyl)cyclopentane from Step A in 100 mL of 1,2-dichloroethane was added 8.7 g (28 mmole) of (R)-3-ethoxycarbonylpiperidine hydrochloride and 4.9 mL (28 mmole) of DIPEA. After stirring at room temperature for 10 minutes, 9.2 g (44 mmole) of sodium triacetoxyborohydride was added. The reaction was stirred for 16 hours. The reaction was quenched with sat'd sodium bicarbonate and was extracted twice with methylene chloride. The organic layers were each washed with a portion of brine, dried over sodium sulfate, combined and evaporated. The residue was purified by prep LC (20–30% ethyl acetate/hexanes) to give 10.5 g of title compound.

Mass spec (NH$_3$/CI): 626 (M+1).

Step C: 1-(S)-(1-(R)-(3,5-Bis(trifluoromethyl)phenyl) ethoxy)-2-(R)-(4-fluorophenyl)-3-(R)-(((R)-3-carboxypiperidin-1-yl)methyl)-cyclopentane To a solution of 10.14 g (17.2 mmole) of 1-(S)-(1-(R)-(3,5-bis(trifluoromethyl)phenyl)ethoxy)-2-(R)-(4-fluorophenyl)-3-(R)-(((R)-3-ethoxycarbonylpiperidin-1-yl) methyl)cyclopentane from Step B in 100 mL of methanol was added 17.2 mL (86 mmole) of 5N sodium hydroxide. The reaction was stirred at rt for 20 hours and was then most of the methanol was removed in vacuo. The residue was diluted with water and the pH was adjusted to 7 with 2N hydrochloric acid. The mixture was extracted 3 times with methylene chloride and each organic layer was washed with a portion of brine. The organic layers were dried over sodium sulfate and evaporated to afford 9.0 g of crude title compound as a white foam. NMR (CDCl$_3$)δ: 1.37 (d, J=6 Hz, 3H), 1–8–2.0 (m, 2H), 2.0–2.7 (m, 12H), 2.7–3.1 (m, 2H), 3.2–3.4 (1H), 3.4–3.6 (m, 2H), 3.69 (m, 1H), 4.48 (q, J=6 Hz, 1H), 6.96 (m, 1H), 7.11 (m, 1H), 7.40 (s, 2H), 7.69 (s, 1H).

Mass spec (ESI): 562 (M+1).

The hydrochloride salt can be prepared by dissolving the crude title compound in ether (40 mL/g), addition of excess 2M hydrogen chloride in ether and filtration of the solid precipitate. Alternatively, the title compound can be obtained as the crystalline free amine from water (10 mL/g).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula:

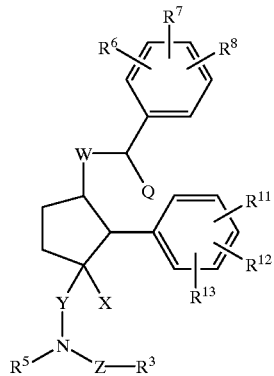

or a pharmaceutically acceptable salt thereof, wherein:
Q is selected from the group consisting of:
(1) hydrogen,
(2) $C_{1-6}$ alkyl,
(3) $C_{1-6}$ alkyl-OH, and
(4) $C_{1-6}$ alkyl-O—$C_{1-6}$ alkyl;
W is selected from the group consisting of:
(1) —O—,
(2) —NH—, and
(3) —N($C_{1-6}$ alkyl)-;
X is selected from the group consisting of:
(1) hydrogen, and
(2) $C_{1-6}$ alkyl, and
(3) $C_{1-6}$ alkyl-OH;
Y is selected from the group consisting of:
(1) a single bond, and
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, wherein halo is fluoro, chloro, bromo or iodo,
(h) —$NR^9R^{10}$, wherein $R^9$ and $R^{10}$ are independently selected from:
(I) hydrogen,
(II) $C_{1-6}$ alkyl,
(III) phenyl,
(IV) ($C_{1-6}$ alkyl)-phenyl,
(V) ($C_{1-6}$ alkyl)-hydroxy, and
(VI) ($C_{1-6}$ alkyl)-($C_{1-4}$ alkoxy),
(i) —$NR^9$—$COR^{10}$,
(j) —$NR^9$—$CO_2R^{10}$,
(k) —CO—$NR^9R^{10}$,
(l) —$COR^9$, and
(m) —$CO_2R^9$;
Z is selected from the group consisting of:
$C_{1-6}$ alkyl, $C_{3-6}$ cycloalkyl and $C_{1-6}$ alkyl($C_{3-6}$ cycloalkyl), which is unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9$—$COR^{10}$,
(j) —$NR^9$—$CO_2R^{10}$,
(k) —CO—$NR^9R^{10}$,
(l) —$COR^9$, and
(m) —$CO_2R^9$;
$R^3$ is selected from the group consisting of:
(1) —$CO_2H$,
(2) -tetrazolyl, and
(3) —CO—NH—$SO_2$—$CH_3$;
$R^5$ is selected from the group consisting of:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9$—$COR^{10}$,
(j) —$NR^9$—$CO_2R^{10}$,
(k) —CO—$NR^9R^{10}$,
(l) —$COR^9$, and
(m) —$CO_2R^9$,
or $R^5$ and Z may be joined together to form a pyrrolidinyl, piperidinyl, piperazinyl or morpholinyl ring which is substituted with $R^3$ and further substituted with one or more of the substituents selected from:
(a) $C_{1-6}$ alkyl,
(b) ($C_{1-6}$ alkyl)-phenyl,
(c) ($C_{1-6}$ alkyl)-hydroxy,
(d) ($C_{1-6}$ alkyl)-($C_{1-4}$ alkoxy),
(e) hydroxy,
(f) oxo,
(g) $C_{1-6}$ alkoxy,
(h) phenyl-$C_{1-3}$ alkoxy,
(i) phenyl,
(j) —CN,
(k) halo,
(l) —$NR^9R^{10}$,
(m) —$NR^9$—$COR^{10}$,
(n) —$NR^9$—$CO_2R^{10}$,
(o) —CO—$NR^9R^{10}$,
(p) —$COR^9$, and
(q) —$CO_2R^9$,
$R^6$, $R^7$ and $R^8$ are independently selected from the group consisting of:
(1) hydrogen,
(2) $C_{1-6}$ alkoxy,
(3) halo,
(4) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, (h) —NR$^9$R$^{10}$,
(i) —NR$^9$—COR$^{10}$,
(j) —NR$^9$—CO$_2$R$^{10}$,
(k) —CO—NR$^9$R$^{10}$,
(l) —COR$^9$,
(m) —CO$_2$R$^9$,
(n) heterocycle, wherein heterocycle is selected from the group consisting of:
  (A) benzimidazolyl,
  (B) benzofuranyl,
  (C) benzothiophenyl,
  (D) benzoxazolyl,
  (E) furanyl,
  (F) imidazolyl,
  (G) indolyl,
  (H) isooxazolyl,
  (I) isothiazolyl,
  (J) oxadiazolyl,
  (K) oxazolyl,
  (L) pyrazinyl,
  (M) pyrazolyl,
  (N) pyridyl,
  (O) pyrimidyl,
  (P) pyrrolyl,
  (Q) quinolyl,
  (R) tetrazolyl,
  (S) thiadiazolyl,
  (T) thiazolyl,
  (U) thienyl,
  (V) triazolyl,
  (W) azetidinyl,
  (X) 1,4-dioxanyl,
  (Y) hexahydroazepinyl,
  (Z) piperazinyl,
  (AA) piperidinyl,
  (AB) pyrrolidinyl,
  (AC) morpholinyl,
  (AC) thiomorpholinyl,
  (AD) dihydrobenzimidazolyl,
  (AE) dihydrobenzofuranyl,
  (AF) dihydrobenzothiophenyl,
  (AG) dihydrobenzoxazolyl,
  (AH) dihydrofuranyl
  (AI) dihydroimidazolyl,
  (AJ) dihydroindolyl,
  (AK) dihydroisooxazolyl,
  (AL) dihydroisothiazolyl,
  (AM) dihydrooxadiazolyl,
  (AN) dihydrooxazolyl,
  (AO) dihydropyrazinyl,
  (AP) dihydropyrazolyl,
  (AQ) dihydropyridinyl,
  (AR) dihydropyrimidinyl,
  (AS) dihydropyrrolyl,
  (AT) dihydroquinolinyl,
  (AU) dihydrotetrazolyl,
  (AV) dihydrothiadiazolyl,
  (AW) dihydrothiazolyl,
  (AX) dihydrothienyl,
  (AY) dihydrotriazolyl,
  (AZ) dihydroazetidinyl,
  (BA) dihydro-1,4-dioxanyl,
  (BB) tetrahydrofuranyl, and
  (BC) tetrahydrothienyl,
    and wherein the heterocycle is unsubstituted or substituted with one or more substituent(s) selected from:
    (i) C$_{1-6}$ alkyl, unsubstituted or substituted with halo, —CF$_3$, —OCH$_3$, or phenyl,
    (ii) C$_{1-6}$ alkoxy,
    (iii) oxo,
    (iv) hydroxy,
    (v) thioxo,
    (vi) —SR$^9$,
    (vii) halo,
    (viii) cyano,
    (ix) phenyl,
    (x) trifluoromethyl,
    (xi) —(CH$_2$)$_m$—NR$^9$R$^{10}$,
    (xii) —NR$^9$COR$^{10}$,
    (xiii) —CONR$^9$R$^{10}$,
    (xiv) —CO$_2$R$^9$, and
    (xv) —(CH$_2$)$_m$—OR$^9$,
(5) hydroxy,
(6) —CN,
(7) —CF$_3$,
(8) —NO$_2$,
(9) —SR$^{14}$, wherein R$^{14}$ is hydrogen or C$_{1-6}$alkyl,
(10) —SOR$^{14}$,
(11) —SO$_2$R$^{14}$,
(12) —NR$^9$—COR$^{10}$,
(13) —CO—NR$^9$—COR$^{10}$,
(14) —NR$^9$R$^{10}$,
(15) —NR$^9$—CO$_2$R$^{10}$,
(16) —COR$^9$,
(17) —CO$_2$R$^9$,
(18) heterocycle, wherein heterocycle is as defined above,
(19) —(C$_{1-6}$alkyl)-heterocycle, wherein heterocycle is as defined above,
(20) —N(heterocycle)—SO$_2$R$^{14}$, wherein heterocycle is as defined above;
R$^{11}$, R$^{12}$ and R$^{13}$ are independently selected from:
(1) hydrogen,
(2) C$_{1-6}$ alkyl, unsubstituted or substituted with one or more of the substituents selected from:
  (a) hydroxy,
  (b) oxo,
  (c) C$_{1-6}$ alkoxy,
  (d) phenyl-C$_{1-3}$ alkoxy,
  (e) phenyl,
  (f) —CN,
  (g) halo,
  (h) —NR$^9$R$^{10}$,
  (i) —NR$^9$—COR$^{10}$,
  (j) —NR$^9$—CO$_2$R$^{10}$,
  (k) —CO—NR$^9$R$^{10}$,
  (l) —COR$^9$,
  (m) —CO$_2$R$^9$;
(3) halo,
(4) —CN,
(5) —CF$_3$,
(6) —NO$_2$,
(7) hydroxy,
(8) C$_{1-6}$alkoxy,
(9) —COR$^9$, and
(10) —CO$_2$R$^9$;
with the proviso that if Q is —CH$_3$, W is —O—, X is hydrogen, Y is —CH$_2$—, Z is —CH$_2$—, R$^3$ is —CO$_2$H, R$^5$ is hydrogen, and two of R$^6$, R$^7$ and R$^8$ are 3,5 di—CF$_3$, then none of R$^{11}$, R$^{12}$ or R$^{13}$ are para-fluoro;

and pharmaceutically acceptable salts and individual diasteromers thereof.

2. The compound of claim 1 wherein:
Q is selected from the group consisting of:
   (1) hydrogen,
   (2) —$CH_3$, and
   (3) —$CH_2$—OH;
W is —O—;
X is hydrogen;
Y is selected from the group consisting of:
   (1) a single bond,
   (2) —$CH_2$—, and
   (3) —$CH_2$—OH;
Z is selected from the group consisting of: $C_{1-6}$ alkyl, $C_{3-6}$ cycloalkyl and $C_{1-6}$ alkyl($C_{3-6}$ cycloalkyl);
$R^3$ is —$CO_2H$;
$R^5$ is selected from the group consisting of:
   (1) hydrogen, and
   (2) $C_{1-6}$ alkyl,
or $R^5$ and Z are joined together to form a piperidinyl ring which is substituted with $R^3$ and which is further unsubstituted or substituted with $C_{1-6}$ alkyl;
$R^6$, $R^7$ and $R^8$ are independently selected from the group consisting of:
   (1) hydrogen,
   (2) —$CF_3$,
   (3) $C_{1-6}$alkoxy, and
   (4) 1-, 2- or 5-tetrazolyl, wherein the tetrazolyl is unsubstituted or substituted with a substitutent selected from the group consisting of:
      (a) $C_{1-6}$ alkyl,
      (b) -cyclopropyl,
      (c) $CH_2$-cyclopropyl,
      (d) —S—$C_{1-4}$alkyl,
      (e) —SO—$C_{1-4}$alkyl,
      (f) —$SO_2$—$C_{1-4}$alkyl,
      (g) phenyl,
      (h) —$NR^9R^{10}$,
      (i) —$CH_2$—CO—$CF_3$, and
      (j) —$CF_3$;
$R^{11}$, $R^{12}$ and $R^{13}$ are independently selected from:
   (1) hydrogen, and
   (2) fluoro;
   and pharmaceutically acceptable salts and individual diasteromers thereof.

3. The compound of claim 1 wherein Q is selected from the group consisting of:
   (1) hydrogen,
   (2) —$CH_3$, and
   (3) —$CH_2$—OH.

4. The compound of claim 1 wherein Q is —$CH_3$.

5. The compound of claim 1 wherein W is —O—.

6. The compound of claim 1 wherein Y is selected from the group consisting of:
   (1) a single bond,
   (2) —$CH_2$—, and
   (3) —$CH_2$—OH.

7. The compound of claim 1 wherein Y is —$CH_2$—.

8. The compound of claim 1 wherein $R^3$ is —$CO_2H$.

9. The compound of claim 1 wherein $R^5$ is selected from the group consisting of:
   (1) hydrogen, and
   (2) methyl.

10. The compound of claim 1 wherein Z is selected from the group consisting of:
    (1) —$CH_2$—,
    (2) —$CH_2CH_2$—,
    (3) —$CH_2C(CH_3)_2$—,
    (4) —$CH_2C(CH_2CH_3)_2$—,
    (5) —$CH_2C(CH_3)(CH(CH_3)_2)$—,
    (6) —$CH_2C$(cyclopentyl)-, and
    (7) —$CH_2C$(cyclohexyl)-.

11. The compound of claim 1 wherein $R^5$ and Z are joined together to form a piperidinyl ring which is substituted with $R^5$ and which is further unsubstituted or substituted with methyl.

12. The compound of claim 1 wherein $R^6$, $R^7$ and $R^8$ are independently selected from the group consisting of:
    (1) hydrogen,
    (2) —$CF_3$,
    (3) $C_{1-4}$alkoxy, and
    (4) heterocycle, wherein the heterocycle is selected from the group consisting of:
       (A) tetrazolyl,
       (B) imidazolyl,
       (C) triazolyl,
       (D) pyridyl,
       and wherein the heterocycle is unsubstituted or substituted with one or more substituent(s) selected from:
       (i) $C_{1-4}$ alkyl,
       (ii) -cyclopropyl, and
       (iii) —$CF_3$.

13. The compound of claim 1 wherein the phenyl ring bearing $R^6$, $R^7$ and $R^8$ is selected from:
    3,5-bis(trifluormethyl)phenyl,
    2-methoxy-5-tetrazol-1-yl-phenyl,
    2-methoxy-5-(5-methyl-tetrazol-1-yl)-phenyl,
    2-methoxy-5-(5-ethyl-tetrazol-1-yl)-phenyl,
    2-methoxy-5-(5-propyl-tetrazol-1-yl)-phenyl,
    2-methoxy-5-(5-trifluoromethyl-tetrazol-1-yl)-phenyl,
    2-methoxy-5-(5-cyclopropyl-tetrazol-1-yl)-phenyl, and
    2-methoxy-5-(5-methylsulfanyl-tetrazol-1-yl)-phenyl.

14. The compound of claim 1 wherein $R^{11}$, $R^{12}$ and $R^{13}$ are independently selected from:
    (1) hydrogen, and
    (2) fluoro.

15. The compound of claim 1 wherein the phenyl ring bearing $R^{11}$, $R^{12}$ and $R^{13}$ is unsubstituted phenyl or is para-fluorophenyl.

16. A compound which is selected from the group consisting of:
    1-(S)-(1-(R)-(3,5-Bis(trifluoromethyl)phenyl)ethoxy)-2-(R)-(4-fluorophenyl)-3-(R)-(((R and/or S)-3-carboxylpyrrolidin-1-yl)methyl)cyclopentane;
    1-(S)-(1-(R)-(3,5-Bis(tifluoromethyl)phenyl)ethoxy)-2-(R)-(4-fluorophenyl)-3-(R)-(((2-carboxylethyl)methylamino)methyl)cyclopentane;
    1-(S)-(1-(R)-(3,5-Bis(tifluoromethyl)phenyl)ethoxy)-2-(S)-(4-fluorophenyl)-3-(R)-((2-carboxylethyl)methylamino)cyclopentane;
    1-(S)-(1-(R)-(3,5-Bis(trifluoromethyl)phenyl)ethoxy)-2-(S)-(4-fluorophenyl)-3-(R)-((3-carboxylpropyl)methylamino)cyclopentane;
    1-(S)-(1-(R)-(3,5-Bis(trifluoromethyl)phenyl)ethoxy)-2-(R)-(4-fluorophenyl)-3-(R)-((3-carboxylpropyl)methylamino)methyl)cyclopentane;
    1-(S)-(1-(R)-(3,5-Bis(trifluoromethyl)phenyl)ethoxy)-2-(R)-(4-fluorophenyl)-3-(R)-((4-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-((4-carboxyl-4-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxylpyrrolidin-1-yl)methyl)cyclopentane;

1-(S)-(1-(R)-(3,5-Bis(trifluoromethyl)phenyl)ethoxy)-2-(R)-(4-fluorophenyl)-3-(R)-(((RS)-3-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((2-carboxylethyl)amino)methyl)cyclopentane;

1-(S)-(1-(R)-(3,5-Bis(trifluoromethyl)phenyl)ethoxy)-2-(R)-(4-fluorophenyl)-3-(R)-(((carboxylmethyl)amino)methyl)cyclopentane;

1-(S)-(1-(R)-(3,5-Bis(trifluoromethyl)phenyl)ethoxy)-2-(R)-(4-fluorophenyl)-3-(R)-((((S)-1-carboxylethyl)amino)methyl)cyclopentane;

1-(S)-(1-(R)-(3,5-Bis(trifluoromethyl)phenyl)ethoxy)-2-(R)-(4-fluorophenyl)-3-(R)-((((R)-1-carboxylethyl)amino)methyl)cyclopentane;

1-(S)-(1-(R)-(3,5-Bis(trifluoromethyl)phenyl)ethoxy)-2-(R)-(4-fluorophenyl)-3-(R)-((4-(tetrazol-5-yl)piperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((2-(tetrazol-5-yl)ethyl)methylamino)methyl)cyclopentane;

1-(S)-(1-(R)-(3,5-Bis(trifluoromethyl)phenyl)ethoxy)-2-(R)-(4-fluorophenyl)-3-(S)-((4-carboxylpiperidin-1-yl)methyl)cyclopentane;

1-(S)-(1-(R)-(3-Fluoro-5-trifluoromethyl)phenyl)ethoxy)-2-(R)-(4-fluorophenyl)-3-(R)-((4-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-((4-(methylsulfonylaminocarbonyl)piperidin-1-yl) methyl)cyclopentane;

1-(S)-(1-(3,5-Bis(trifluoromethyl)phenyl)methoxy)-2-(R)-(4-fluorophenyl)-3-(R)-((4-carboxylpiperidin-1-yl)methyl)cyclopentane;

1-(S)-(1-(3,5-Bis(trifluoromethyl)phenyl)methoxy)-2-(R)-(4-fluorophenyl)-3-(R)-(((S)-2-carboxylpyrrolidin-1-yl)methylcyclopentane;

1-(S)-(1-(3,5-Bis(trifluoromethyl)phenyl)methoxy)-2-(R)-(4-fluorophenyl)-3-(R)-(((R,S)-3-carboxylpyrrolidin-1-yl)methyl)cyclopentane;

1-(S)-(1-(3,5-Bis(trifluoromethyl)phenyl)methoxy)-2-(R)-(4-fluorophenyl)-3-(R)-(((2-carboxylethyl)amino)methyl)cyclopentane;

1-(S)-(1-(3,5-Bis(trifluoromethyl)phenyl)methoxy)-2-(R)-(4-fluorophenyl)-3-(R)-(((2-carboxylethyl)methylamino)methyl)cyclopentane;

1-(S)-(1-(S)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane;

1-(S)-(1-(R)-(3,5-Bis(trifluoromethyl)phenyl)-2-hydroxyethoxy)-2-(R)-(4-fluorophenyl)-3-(R)-((4-carboxylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-((((2-carboxylethyl)methyl)amino)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R,S)-3-carboxylpyrrolidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-((4-carboxyl-4-methylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R and S)-3-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((RS)-3-carboxylpiperazin-1-yl)methyl)cyclopentane;

1-(S)-(1-(R)-(3,5-Bis(trifluoromethyl)phenyl)ethoxy)-2-(R)-(4-fluorophenyl)-3-(R)-(((RS)-2-carboxyl-1-methylpiperazin-4-yl)methyl)cyclopentane;

1-(S)-(1-(R)-(3,5-Bis(trifluoromethyl)phenyl)ethoxy)-2-(R)-(4-fluorophenyl)-3-(R)-(((RS)-2-carboxylmorpholin-4-yl)methyl)cyclopentane;

1-(S)-(1-(R)-(3,5-Bis(trifluoromethyl)phenyl)ethoxy)-2-(R)-(4-fluorophenyl)-3-(R)-(((R)-3-carboxyl-3-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxyl-3-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((1-carboxyl-1-methyl)ethyl)aminomethyl)cyclopentane;

1-(S)-(1-(R)-(3,5-Bis(trifluoromethyl)phenyl)ethoxy)-2-(R)-(4-fluorophenyl)-3-(R)-((((R)-1-carboxyl-1,2-dimethylprop-1-yl)amino)methyl)cyclopentane;

1-(S)-(1-(R)-(3,5-bis(trifluoromethyl)phenyl)ethoxy)-2-(R)-(4-fluorophenyl)-3-(R)-((((S)-1-carboxyl-1,2-dimethylprop-1-yl)aminomethyl)cyclopentane;

1-(S)-(1-(R)-(3,5-Bis(trifluoromethyl)phenyl)ethoxy)-2-(R)-(4-fluorophenyl)-3-(R)-(((R)-3-carboxyl-(R)-5-methylpiperidin-1-yl)methyl)cyclopentane;

1-(S)-(1-(R)-(3,5-Bis(tifluoromethyl)phenyl)ethoxy)-2-(R)-(4-fluorophenyl)-3-(R)-(((R)-3-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-3-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((R)-2-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxyl-(R)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-(((S)-2-carboxyl-(S)-5-methylpiperidin-1-yl)methyl)cyclopentane;

1-(S)-(1-(R)-(3,5-Bis(trifluoromethyl)phenyl)ethoxy)-2-(R)-(4-fluorophenyl)-3-(R)-((((S)-1-carboxylethyl)methylamino)methyl)cyclopentane;

1-(S)-(1-(R)-(3,5-Bis(trifluoromethyl)phenyl)ethoxy)-2-(R)-(4-fluorophenyl)-3-(R)-((((R)-1-carboxylethyl)methylamino)methyl)cyclopentane;

1-(S)-(1-(R)-(3,5-Bis(trifluoromethyl)phenyl)ethoxy)-2-(R)-(4-fluorophenyl)-3-(R)-((((RS)-2-carboxylprop-1-yl)methylamino)methyl)cyclopentane;

1-(S)-(1-(S)-(3,5-Bis(trifluoromethyl)phenyl)-2-hydroxyethoxy)-2-(R)-(4-fluorophenyl)-3-(R)-(((R)-3-carboxyl-3-methylpiperidin-1-yl)methyl)cyclopentane;

1-(S)-(1-(S)-(3,5-Bis(trifluoromethyl)phenyl)-2-hydroxyethoxy)-2-(R)-(4-fluorophenyl)-3-(R)-(((S)-3-carboxyl-3-methylpiperidin-1-yl)methyl)cyclopentane;

1-(S)-(1-(R)-(3,5-Bis(tifluoromethyl)phenyl)ethoxy)-2-(S)-(4-fluorophenyl)-3-(R)-((2-carboxyl-2-methylprop-1-yl)methylamino)cyclopentane;

1-(S)-(1-(R)-(3,5-Bis(trifluoromethyl)phenyl)ethoxy)-2-(S)-(4-fluorophenyl)-3-(R)-((2-carboxyl-2-ethylbut-1-yl)methylamino)cyclopentane;

1-(S)-(1-(R)-(3,5-Bis(trifluoromethyl)phenyl)ethoxy)-2-(R)-(4-fluorophenyl)-3-(R)-(((1-carboxylcyclopent-1-yl)methyl)methylamino)cyclopentane;

1-(S)-(1-(R)-(3,5-Bis(trifluoromethyl)phenyl)ethoxy)-2-(R)-(4-fluorophenyl)-3-(R)-((1-carboxylcyclohex-1-ylamino)methyl)cyclopentane;

1-(S)-(1-(R)-(3,5-Bis(trifluoromethyl)phenyl)ethoxy)-2-(R)-(4-fluorophenyl)-3-(R)-((1-carboxylcyclopent-1-ylamino)methyl)cyclopentane;

1-(S)-(1-(R)-(3,5-Bis(trifluoromethyl)phenyl)ethoxy)-2-(R)-(4-fluorophenyl)-3-(R)-(((1-carboxylcyclohex-1-yl)methylamino)methyl)cyclopentane;

1-(S)-(1-(R)-(3,5-Bis(trifluoromethyl)phenyl)ethoxy)-2-(R)-(4-fluorophenyl)-3-(R)-(((1-carboxylcyclopent-1-yl)methylamino)methyl)cyclopentane;

1-(S)-(1-(R)-(3,5-Bis(tifluoromethyl)phenyl)ethoxy)-2-(R)-(4-fluorophenyl)-3-(R)-(((R)-3-carboxylpiperidin-1-yl)methyl)cyclopentane;

and pharmaceutically acceptable salts and individual diasteromers thereof.

17. A pharmaceutical composition comprising a pharmaceutically acceptable carrier and an effective amount of the compound of claim 1.

18. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site in the mammal.

19. A method for antagonizing the effect of neurokinin A at its receptor site or for the blockade of neurokinin-2 receptors in a mammal which comprises the administration to the mammal of the compound of claim 1 in an amount that is effective for antagonizing the effect of neurokinin A at its receptor site in the mammal.

20. A method of treating or preventing depression in a mammal in need thereof which comprises the administration to the mammmal of an effective amount of the compound of claim 1.

21. A method of treating or preventing anxiety in a mammal in need thereof which comprises the administration to the mammmal of an effective amount of the compound of claim 1.

22. A method for the treatment or prevention of emesis in a mammal in need thereof which comprises the administration to the mammal of an effective amount of the compound of claim 1.

23. A compound which is:

1-(S)-(1-(R)-(3,5-Bis(trifluoromethyl)phenyl)ethoxy)-2-(R)-(4-fluorophenyl)-3-(R)-(((R)-3-carboxylpiperidin-1-yl)methyl)cyclopentane or a pharmaceutically acceptable salt thereof.

24. A pharmaceutical composition comprising a pharmaceutically acceptable carrier and an effective amount of a compound which is:

1-(S)-(1-(R)-(3,5-Bis(trifluoromethyl)phenyl)ethoxy)-2-(R)-(4-fluorophenyl)-3-(R)-(((R)-3-carboxylpiperidin-1-yl)methyl)cyclopentane or a pharmaceutically acceptable salt thereof.

25. A method for the treatment or prevention of depression in a human in need thereof which comprises administering to the human an effective amount of a compound which is:

1-(S)-(1-(R)-(3,5-Bis(trifluoromethyl)phenyl)ethoxy)-2-(R)-(4-fluorophenyl)-3-(R)-(((R)-3-carboxylpiperidin-1-yl)methyl)cyclopentane or a pharmaceutically acceptable salt thereof.

* * * * *